US008735444B2

(12) United States Patent (10) Patent No.: US 8,735,444 B2
Hell et al. (45) Date of Patent: May 27, 2014

(54) FLUORINATED RHODAMINES AS PHOTOSTABLE FLUORESCENT DYES FOR LABELLING AND IMAGING TECHNIQUES

(75) Inventors: Stefan W. Hell, Goettingen (DE); Vladimir N. Belov, Goettingen (DE); Gyuzel Mitronova, Goettingen (DE); Mariano Bossi, Buenos Aires (AR); Gael Moneron, Goettingen (DE); Christian A. Wurm, Goettingen (DE); Stefan Jakobs, Goettingen (DE); Christian Eggeling, Goettingen (DE); Jakob Bierwagen, Goettingen (DE); Lars Meyer, Goettingen (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 13/380,148

(22) PCT Filed: Jun. 26, 2009

(86) PCT No.: PCT/EP2009/004650
§ 371 (c)(1),
(2), (4) Date: Jan. 13, 2012

(87) PCT Pub. No.: WO2010/149190
PCT Pub. Date: Dec. 29, 2010

(65) Prior Publication Data
US 2012/0135459 A1 May 31, 2012

(51) Int. Cl.
*A61K 31/352* (2006.01)
*C07D 311/82* (2006.01)
(52) U.S. Cl.
CPC .................................. *C07D 311/82* (2013.01)
USPC .......................................... 514/454; 549/388
(58) Field of Classification Search
CPC .................................................. C07D 311/82
USPC .......................................... 549/388; 514/454
See application file for complete search history.

(56) References Cited

U.S. PATENT DOCUMENTS

| 4,945,176 | A | 7/1990 | Hammond et al. |
| 5,047,559 | A | 9/1991 | Hammond et al. |
| 5,111,472 | A | 5/1992 | Hammond et al. |
| 5,283,336 | A | 2/1994 | Field et al. |
| 6,130,101 | A | 10/2000 | Mao et al. |
| 2007/0249014 | A1 | 10/2007 | Agnew et al. |

FOREIGN PATENT DOCUMENTS

| EP | 1441010 A1 | 7/2004 |
| EP | 1670789 A2 | 6/2006 |
| EP | 2036897 A1 | 3/2009 |
| WO | 9739064 A1 | 10/1997 |
| WO | 2005003330 A2 | 1/2005 |

OTHER PUBLICATIONS

Bates et al., "Multicolor Super-Resolution Imaging with Photo-Switchable Fluorescent Probes", Science, vol. 317, pp. 1749-1753 (2007).
Bigotti et al., "The Influence of Fluoroalkyl-Group Electronegativity on Stereocontrol in the Synthesis of ψ[CH(RF) NH]Gly Peptides", SYNLETT, No. 7, pp. 958-962 (2008).
Bossi et al., "Reversible rot fluoreszierende molekulare Schalter", Angew. Chem., vol. 118, pp. 7623-7267 (2006).
Bossi et al., "Reversible Red Fluorescent Molecular Switches", Angew. Chem. Int. Ed., vol. 45, pp. 7462-7465 (2006).
Bossi et al., Multicolor Far-Field Fluorescence Nanoscopy through Isolated Detection of Distinct Molecular Species, Nano Letters, vol. 8, No. 8, pp. 2463-2468 (2008).
Boyarskiy et al., "Photostable, Amino Reactive and Water-Soluble Fluorescent Labels Based on Sulfonated Rhodamine with a Rigidized Xanthene Fragment", Chem. Eur. J., vol. 14, pp. 1784-1792 (2008).
Cohen et al., "A Simple Preparation of Phenols from Diazonium Ions via the Generation and Oxidation of Aryl Radicals by Copper Salts", J. Org. Chem., vol. 42, No. 12, pp. 2053-2058 (1977).
Eggeling et al., "Photobleaching of Fluorescent Dyes under Conditions Used for Single-Molecule Detection: Evidence of Two-Step Photolysis", Anal. Chem., vol. 70, pp. 2651-2659 (1998).
Foelling et al., "Fluorescence nanoscopy by ground-state depletion and single-molecule return", Nature Methods, vol. 5, No. 11, pp. 943-945 (2008).
Hammond, "Spectroscopic and Laser Properties of the Dye Chromogen Red B", Journal of Photochemistry, vol. 10, pp. 467-471 (1979).
Haugland, "A Guide to Fluorescent Probes and Labeling Technologies", Invitrogen, Carlsbad, pp. 11-37, 38, 53 (2005).
Hell, "Microscopy and its focal switch", Nature Methods, vol. 6, No. 1, pp. 24-32.
Hermanson, "Bioconjugate Techniques", Academic Press, San Diego, pp. 316-331 (1996).
Karstens et al., "Rhodamine B and Rhodamine 101 as Reference Substances for Fluorescence Quantum Yield Measurements", J. Phy. Chem., vol. 84, pp. 1871-1872 (1980).
Kubin et al., "Fluorescence Quantum Yields of Some Rhodamine Dyes", Journal of Luminescence, vol. 27, pp. 455-462 (1982).
O'Hare et al., "Chemical probes shed light on protein function", Current Opinion in Structural Biology, vol. 17, pp. 488-494 (2007).
Panchuk-Voloshina et al., "Alexa Dyes, a Series of New Fluorescent Dyes that Yield Exceptionally Bright, Photostable Conjugates", J. Histochem. Cytochem., vol. 47, No. 9, pp. 1179-1188 (1999).
Ulrich et al., "The Chemistry of Fluorescent Bodipy Dyes: Versatility Unsurpassed", Angew. Chem. Int. Ed., vol. 47, pp. 1184-1201 (2008).
Westphal et al., "Video-Rate Far-Field Optical Nanoscopy Dissects Synaptic Vesicle Movement", Science, vol. 320, pp. 246-249 (2008).
International Search Report for PCT/EP2009/004650 dated Feb. 12, 2010.

*Primary Examiner* — Rebecca Anderson
*Assistant Examiner* — Karen Cheng
(74) *Attorney, Agent, or Firm* — Caesar, Rivise, Bernstein, Cohen & Pokotilow, Ltd.

(57) ABSTRACT

The present invention relates to novel fluorinated 3,6-diaminoxanthene compounds derived from the basic structural formula (I) and to their uses as photostable fluorescent dyes, e.g. for immunostainings and spectroscopic and microscopic applications, in particular in conventional microscopy, stimulated emission depletion (STED) reversible saturable optically linear fluorescent transitions (RESOLFT) microscopy, and fluorescence correlation spectroscopy. The claimed compounds are also useful as molecular probes in various spectroscopic applications.

4 Claims, 7 Drawing Sheets

Figure 1A:
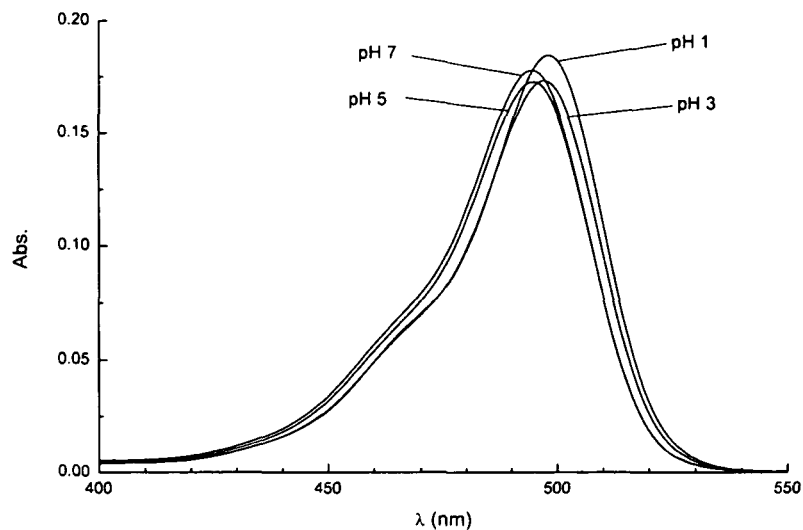

FLUORINATED RHODAMINES AS PHOTOSTABLE FLUORESCENT DYES FOR LABELLING AND IMAGING TECHNIQUES

BACKGROUND OF THE INVENTION

New physical concepts that overcome the diffraction limit by using the dark and bright states of the fluorescent marker emerged in the last decade [a) S. W. Hell, *Science* 2007, 317, 1749-1753; b). S. W. Hell, *Nature Meth.* 2009, 6, 24-32; c) J. Fölling, M. Bossi, H. Bock, R. Medda, C. A. Wurm, B. Hein, S. Jakobs, C. Eggeling, S. W. Hell, *Nature Meth.* 2008, 5, 943-945]. One of them is based on the reversible saturable optically linear fluorescence transitions (RESOLFT) and operates with molecular ensembles of fluorophores. For example, stimulated emission depletion (STED) microscopy—the first concept of the RESOLFT type—uses the ground (singlet) state of the fluorophore ($S_0$) as a dark state, and the first excited state ($S_1$) as a bright one.

In practical applications of the STED method, a focused pulse excites fluorescence in a small spot (with dimensions limited by diffraction), and immediately after that a redshifted doughnut-shaped STED beam quenches the fluorescence of excited molecules by stimulated emission ($S_1 \rightarrow S_0$) everywhere, except the very centre of the doughnut. For squeezing the fluorescence to a very small central spot, the quenching rate should exceed the rate of the spontaneous transition to a ground state $S_0$. Fluorescent lifetimes of organic fluorophores ($\tau_{fl} \sim 10^{-9}$ s) and their optical cross-sections of the $S_1 \rightarrow S_0$ transitions ($\sigma \sim 10^{-16}$ cm$^2$) imply that the STED-pulse should have a very high power of ca. 10 MW/cm$^2$ [$I_{STED} > I_S \approx (\sigma \tau_{fl})^{-1} \sim 10^{25}$ photons/(cm$^2 \times$s)]. Quite recently first STED images of the living cells were recorded at a rate of 28 frames per seconds. In the course of this study, the movements of synaptic vesicles inside the axons of cultured neurons were resolved with a precision of ca. 60 nm [V. Westphal, S. O. Rizzoli, M. A. Lauterbach, D. Kamin, R. Jahn, S. W. Hell, *Science* 2008, 320, 246-249].

The huge light intensities cause photobleaching of fluorophores, and therefore STED microscopy ultimately requires most photostable fluorescent dyes. For example, fluorescein derivatives are not photostable enough under severe irradiation conditions. Other important qualities of the STED dyes include high fluorescent quantum yields and oscillator strengths (high absorption coefficients), low rate of the triplet state formation, high solubility in water or aqueous buffers and a reactive group (with a linker) for attaching a dye to a biological object. Another valuable feature of a fluorescent dye is the ability to cross the cell membrane. For that, its molecule should not be too big; however a priori it is difficult to predict, if any particular dye will penetrate through the cell membrane.

If an imaging procedure provides an optical resolution on the molecular scale, or if only single molecules remain in the effective detection volume, the dye should be suitable for single molecule detection (e.g. in the method of fluorescence correlation spectroscopy—FCS).

Multicolor RESOLFT techniques and colocalization studies in biology demand improved water-soluble, exceptionally photostable and highly fluorescent dyes, which may be optically separated from each other.

Recently, a far-field fluorescence "nanoscopy" based on switching the majority of the fluorescent molecules to a metastable dark state, such as the triplet, and calculating the position of those left or those that spontaneously returned to the ground state, has been introduced (J. Fölling et. al, *Nature Meth.* 2008, 5, 943-945). This superresolution imaging method of the ground state depletion and single molecule return (GSDIM) requires photostable fluorescent dyes with recovery times from several tens to several hundreds of milliseconds, minimal content of the dye in the ground state after the pump pulse and the possibility to enhance the recovery by the irradiation with the UV laser (375 nm).

In the prior art, several classes of organic substances are known as fluorescent dyes: e.g. pyrenes and other condensed polycyclic aromatic compounds, rhodols, rhodamines, BODIPY derivatives, coumarines, etc.

Coumarine dyes, in particular 7-amino-4-methylcoumarines, have found a limited use as fluorescent labels, because their spectral properties cannot be easily tuned or tailor-made. Simple coumarines absorb in the near-UV region and strongly emit the violet or blue light.

Pyrenes and other condensed aromatic hydrocarbons are highly lipophilic crystalline materials, and it is difficult to increase their solubility in water in order to prevent aggregation and quenching the fluorescence in aqueous medium. However, their excitation/-emission bands can easily be shifted within the whole visible spectral range by changing the number of condensed aromatic rings.

The zwitterionic rhodols, rhodamines and carbopyronines are intrinsically rather hydrophilic. Their spectra can easily be modified by changing the substituents at the xanthene (carbopyronine) fragment and/or in the o-substituted benzoic acid residue. The same is true for the BODIPY dyes (the simplest one absorbs at about 500 nm and emits at ca. 510 nm), though they have one substantial drawback: sometimes, the fluorescence intensity of their bioconjugates is not directly proportional to a number of labelled sites [R. P. Haugland, *A Guide to Fluorescent Probes and Labelling Technologies*, Invitrogen Corp., Carlsbad, 2005, p. 53; for a recent review on the chemistry of fluorescent BODIPY dyes, see: G. Ulrich, R. Ziessel, A. Harrimann, *Angew. Chem. Int. Ed.* 2008, 47, 1184-1201]. Moreover, it is relatively difficult to chemically modify the BODIPY residue in such a way, that it becomes water-soluble. For that, many rhodols or rhodamines may easily be decorated with two sulfonic acid groups simply by sulfonation with $SO_3$ in $H_2SO_4$. Sulfonation is known not only to improve solubility in aqueous media, but it also considerably reduces aggregation and quenching of fluorescence in water or aqueous buffers. It often increases photostability and fluorescence quantum yield of a free dye in solution and after attaching it to a biological macromolecule.

In the following, the properties of a number of commercially available organic fluorescent dyes, in particular rhodamine dyes and fluorescein derivatives, are discussed in more detail [a) G. T. Hermanson, *Bioconjugate Techniques*, Academic Press, San Diego, 1996, pp. 316-331; b) T. Karstens, K. Kobs, *J. Phys. Chem.* 1980, 84, 1871-1872; c) R. P. Haugland, *A Guide to Fluorescent Probes and Labelling Technologies*, Invitrogen Corp., Carlsbad, 2005, pp. 11-37; d) N. Panchuk-Voloshina, R. P. Haugland, J. Bishop-Stewart, M. K. Bhalgat, P. J. Millard, F. Mao, W.-Y. Leung, R. P. Haugland, *J. Histochem. Cytochem.* 1999, 47, 1179-1188].

One of them is rhodamine 110 (Scheme 1), which exhibits a bright green fluorescence ($\phi_{fl}$=0.92 in basic ethanol) [R. F. Kubin, A. N. Fletcher, *J. Luminescence* 1982, 27, 455-462]. Positions and intensities of the absorption and fluorescent maxima of rhodamine 110 depend on the solvent and, to some extent, on pH. Structurally similar 5(6)-carboxyrhodamine 110 (known as Rhodamine Green®) possesses the second carboxylic group in the benzene ring, which may occupy either the p-position to the xanthene fragment (C-5) or to the first carboxylic group. In the latter case the second carboxylate is attached to C-6 (Scheme 1). Fluorescence of Rhodamine Green® is insensitive to pH in the range between 4 and 9. However, conjugation with proteins often quenches the fluorescence of this dye, and its conjugates may precipitate from solutions.

Scheme 1. Commercially available rhodamine dyes: rhodamine 110 (1), NHS ester of Rhodamine Green® 5(6)-carboxylate (2), 5(6)-carboxylate of Alexa Fluor® 488 (3) and its amino reactive esters (4a,b), as well as Alexa Fluor® 500 (5) and Alexa Fluor® 514 (6) NHS esters.

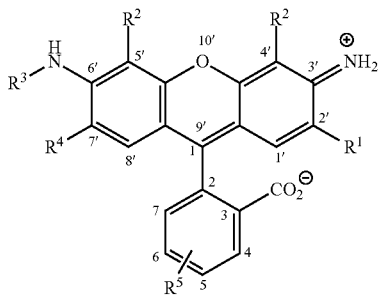

1: $R^1 = R^2 = R^3 = R^4 = R^5 = H$ (Rh110)
2: $R^1 = R^2 = R^3 = R^4 = H$, $R^5 = $ COO(N-succinimidyl)
3: $R^1 = R^3 = R^4 = H$, $R^2 = SO_3H$, $R^5 = $ COOH
4: $R^1 = R^3 = R^4 = H$, $R^2 = SO_3H$,
   $R^5 = $ COO-$C_6F_4$-H-p (a) or
   COO-$C_6H_2$-$Cl_2$-o,o-$SO_3$H-p (b)
5: $R^1 = R^4 = $ Cl, $R^2 = SO_3H$, $R^3 = H$,
   $R^5 = $ COO(N-succinimidyl)
6: $R^1 = H$, $R^2 = SO_3H$,
   $R^3$, $R^4 = $ -$C(CH_3)_2CH_2CH(CH_3)$-,
   $R^5 = $ COO(N-succinimidyl)

To make the fluorescence independent from the pH in a wider range and to reduce the fluorescence quenching after conjugation with proteins, the sulfonated version of Rhodamine Green® (3) and its amino reactive esters (4a,b) were introduced (U.S. Pat. No. 6,130,101). The second, remote carboxy group was activated in the latter compounds. It is much less sterically hindered than the carboxylate in the ortho-position to the bulky heterocyclic residue, and therefore, it may be easily and selectively activated by the formation of N-hydroxysuccinimidyl or substituted phenyl esters (4-6).

Scheme 2. Commerically available fluorescein dyes: fluorescein 5(6)-carboxylate (7), Orgeon Green® 488 5(6)-carboxylate (8) and Oregon Green® 514 5(6)- carboxylate (9).

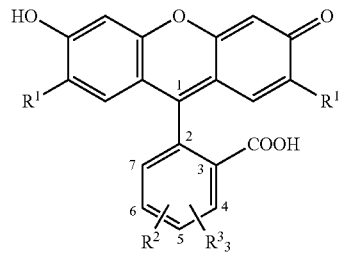

7: $R^1 = R^3 = H$, $R^2 = $ COOH
8: $R^1 = F$, $R^2 = $ COOH, $R^3 = H$
9: $R^1 = R^3 = F$, $R^2 = SCH_2COOH$

Optical properties of the commercially available derivatives of rhodamine 110 (1-6) and fluorescein (7-9, Scheme 2) are given in Table 1. Compound 5 and 6 have additional substituents in the xanthene residue—two chlorine atoms at the positions 2' and 7', or the condensed alkyl ring, which also incorporates one of the nitrogen atoms. These substituents shift the absorption and emission curves to the red (up to ca. 10 and 20 nm for substances 5 and 6, respectively; compared with compounds 1, 3 and 4). Interestingly, introduction of the two fluorine atoms into the positions 2' and 7' of fluorescein 5(6)-carboxylate (7) does not produce any spectral changes (compare the compounds 7 and 8). In order to get the bathochromic shift of ca. 10 nm (compound 9), it was necessary first to introduce 4 fluorine atoms into the o-disubstituted benzene ring of Oregon Green®, and then substitute one of them with thiol group of the mercaptoacetic acid. At the first glance, these small spectral shifts seem to be unimportant. However, there are optical devices (e.g. Zeiss META system) capable to differentiate between the fluorescence maxima, which are only 5-10 nm apart. These systems greatly enlarge the tool-box of available fluorescent colours for multicolour labelling (provided that the excitation laser is the same).

TABLE 1

Optical properties of the commercially available derivatives of rhodamine 110 (1-6) and fluorescein (7-9, Schemes 1 and 2).

| | Compound | | | | | | | | |
|---|---|---|---|---|---|---|---|---|---|
| | 1* | 2*** | 3* | 4a* | 5* | 6* | 7[5]* | 8[6]*,[7]* | 9[6]* |
| $\lambda_{max}$, nm | 496 | 504 | 491 | 494 | 502 | 517 | 492[4]* | 492[4]* | 506 |
| $\lambda_{em}$, nm | 520** | 532 | 515 | 520 | 525 | 542 | 517[4]* | 518[4]* | 526 |
| $\epsilon \times 10^{-4}$ | 8.3 | 7.8 | | 7.2 | 7.1 | 8.0 | 7.8[4]* | 8.5[4]* | 8.6 |

Notes:
*water, pH = 7;
**524 nm in basic EtOH, $\Phi_{fl} = 0.92$;
***MeOH;
[4]*$H_2O$, pH = 9;
[5]*fluorescence is quenched at pH < 7;
[6]*spectra are pH-dependent at pH < 5;
[7]*$\tau$ = 4.1 ns (20° C.).

Derivatives of rhodamine 110 (2-6) are much better fluorophores than spectrally similar fluoresceins (7-9). The parent dye—5(6)-carboxyfluorescein (7)—has relatively high rate of photobleaching, compared with Alexa Fluor® 488. Its fluorescence is highly pH-dependent and significantly reduced at pH<7. High degree of conjugation with biopolymers may quench the fluorescence, so that it will not be directly proportional to the number of fluorescein residues per protein molecule. These drawbacks are no more present in Oregon Green® 488 and Oregon Green® 514, the derivatives of fluorescein with one common feature—two fluorine atoms in the positions 2' and 7' of the xanthene ring (compounds 8 and 9). They are more photostable than fluorescein 7, but still bleach faster than Alexa Fluor® 488 derivatives. Moreover, higher degree of labelling proportionally increases the fluorescence of conjugates, especially in the case of Oregon Green® 514. The latter dye has approximately the same photostability as Rhodamine Green® (2).

However, all of these fluorescent dyes of the prior art have still some drawbacks with respect to photostability and other properties required for application in the most recent microscopic and spectroscopic techniques such as STED, GSDIM etc, where very high light intensities are used, as outlined above.

Consequently, the main object of the present invention was to provide novel fluorescent photostable dyes which would exhibit improved properties, namely in particular resistance against phobleaching in the presence of air-oxygen, hydrophilicity, high values for adsorption and emission maxima, recovery times of several tens—several hundreds of milliseconds, low content of the dye in the ground state after the pump pulse, the possibility of the enhanced recovery caused by the irradiation with the UV light, and which would be particularly suitable for microscopy applications with very high light intensities such as STED, FCS and GSDIM.

This object has been achieved by providing the novel fluorinated rhodamines according to claims 1-3, the methods according to claims 4-6 and the uses of claims 7-13.

DESCRIPTION OF THE INVENTION

The novel rhodamines of the invention are represented by the general structural formulae Ia-Ij below which all comprise the same scaffold of the basic structural formula I.

These novel fluorinated rhodamine compounds of the present invention exhibit a number of favourable characteristics:

a) excitability by an argon ion laser (at 488 and 514 nm) or by the doubled frequency of the Nd:YAG laser;
b) emission of light at about 520 nm or longer wavelengths;
c) providing high fluorescence quantum yields in solution (in a free state and after bioconjugation);
d) low intersystem crossing rates;
e) relatively long (>3 ns) excited state lifetimes;
f) high photostability if excited in solution, under single molecule and STED conditions (by depletion with very strong light at about 600 nm), particularly in the presence of air-oxygen;
g) availability in a hydrophilic (soluble in water and aqueous buffers) and a hydrophobic (insoluble in water or aqueous buffers) form (with the same chromophore) for binding with hydrophilic and lipophilic substrates, respectively;
h) various reactive sites for attaching to various functional groups may easily be introduced;
i) convenient recovery times of ca. 150-450 ms, a moderate to low content of the dye in the ground state after the pump pulse and the possibility to enhance the recovery by irradiation with the UV laser (375 nm).

The novel rhodamines of the present invention are fluorinated 3,6-diaminoxanthene compounds derived from the basic structural formula I

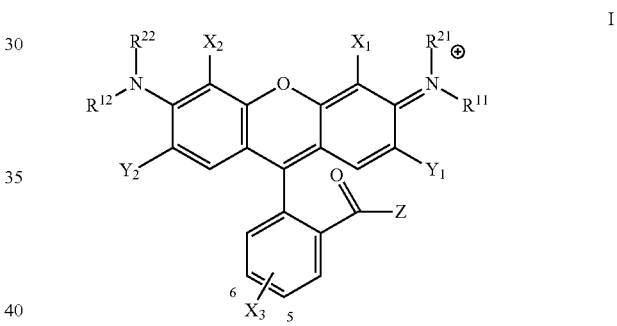

I

These compounds may exist in the "open" form [I-OF] and/or in the "closed" form [I-CF] (if at least one proton is attached to the group denoted as Z, this equilibrium is possible; if not—only the "open" form is present) as depicted below for the basic formula I

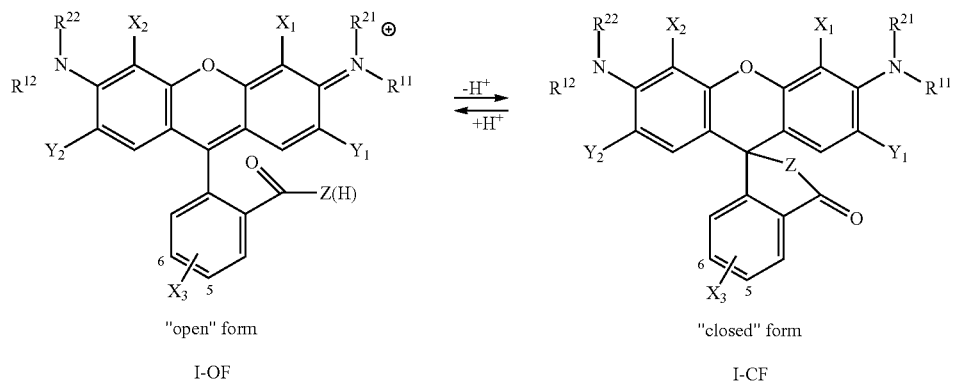

"open" form                    "closed" form

I-OF                           I-CF and the inventive rhodamines have one of the following structural formulae Ia-Ij (only "open" forms are shown in all the following formulae but the respective formulae are meant to include the closed forms where possible as well):

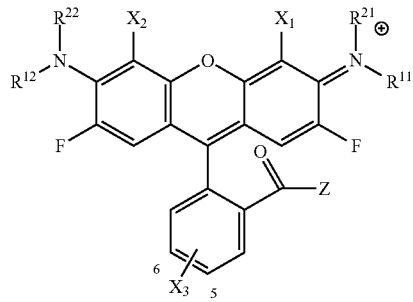

Ia wherein $Y_1=Y_2=F$;

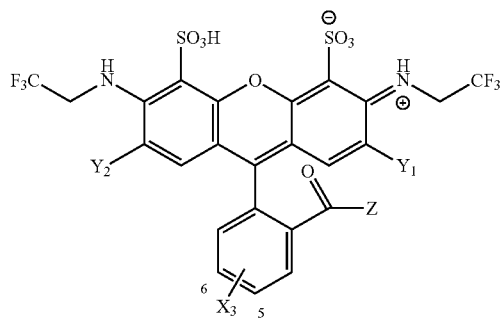

Ib wherein $R^{11}=R^{12}=CH_2CF_3$, $X_1=X_2=SO_3H$, and $R^{21}=R^{22}=H$;

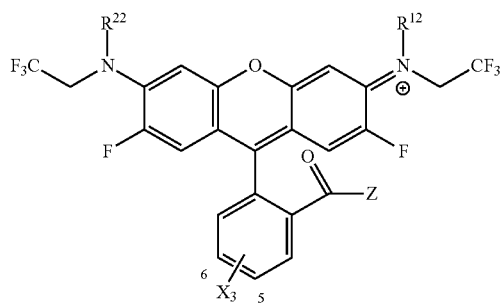

Ic wherein $R^{11}=R^{12}=CH_2CF_3$, $Y_1=Y_2=F$, and $X_1=X_2=H$;

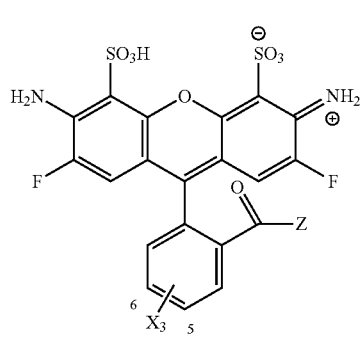

Id wherein $X_1=X_2=SO_3H$, $Y_1=Y_2=F$, and $R^{11}=R^{12}=R=R^{22}=H$;

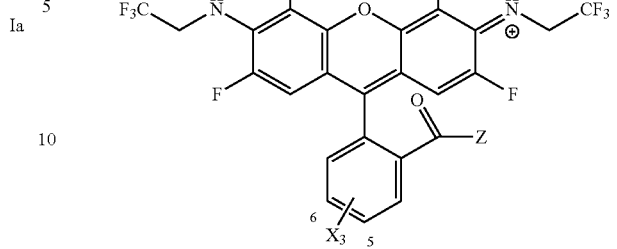

Ie wherein $R^{11}=R^{12}=CH_2CF_3$, $X_1=X_2=SO_3H$, $Y_1=Y_2=F$, and $R^{21}=R^{22}=H$;

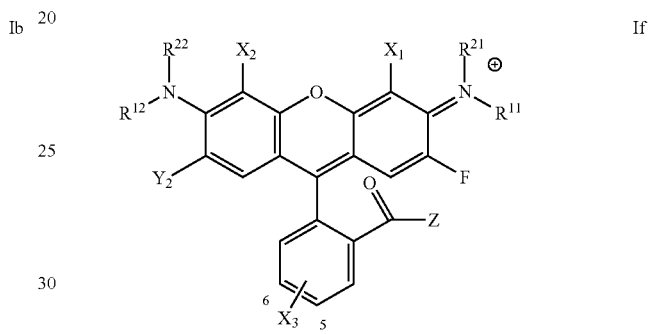

If wherein $Y_1=F$;

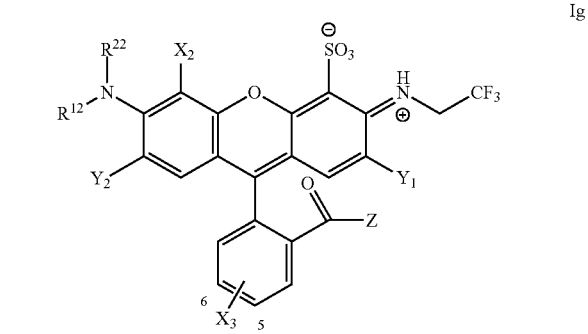

Ig wherein $R^{11}=CH_2CF_3$, $X_1=SO_3H$, and $R^{21}=H$;
wherein $R^{11}=CH_2CF_3$, $Y_1=F$ and $X_1=H$;

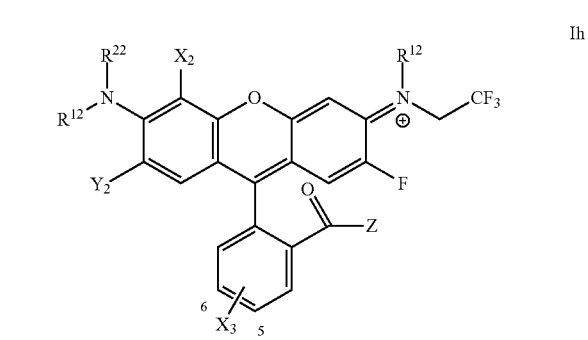

Ih wherein $X_1=SO_3H$; $Y_1=F$ and $R^{11}=R^{12}=H$;

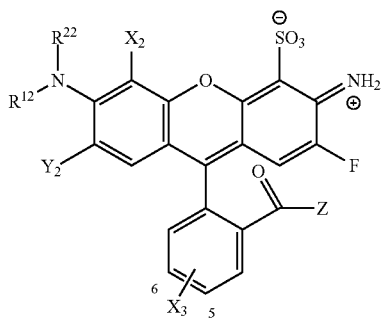

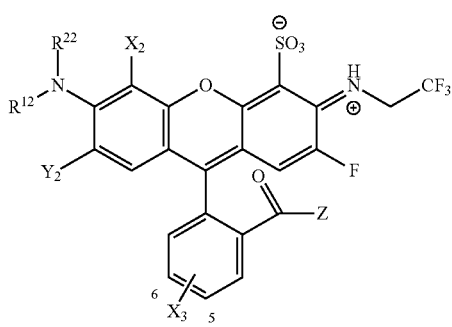

wherein R$^{11}$=CH$_2$CF$_3$, X$_1$=SO$_3$H, Y$_1$=F, and R$^{21}$=H;
and wherein in each of formulae Ia-Ij X$_3$=H, 5-COOH or 6-COOH or an ester thereof, and the undefined substituents from the set R$^{11}$, R$^{12}$, R$^{21}$, R$^{22}$, X$_1$, X$_2$, Y$_1$, Y$_2$, alone or taken together in pairs (e.g. X$_1$, R$^{21}$=—(CH$_2$)$_3$—), may be hydrogen atoms or any alkyl, cycloalkyl, heterocycloalkyl, aryl, heterocyclic aryl groups, or any functionally substituted alkyl, cycloalkyl, aryl, heterocyclic aryl groups, or any combination of said groups; and wherein in each of formulae Ia-Ij Z=OR$^3$ or NR$^4$R$^5$, where R$^3$, R$^4$ and R$^5$ is (are) hydrogen atom(s), any alkyl, cycloalkyl, heterocycloalkyl, aryl, heterocyclic aryl group, or any functionally substituted alkyl, cycloalkyl, heterocycloalkyl, aryl, heterocyclic aryl group, or any combination of said groups.

The term "aryl", as used herein, refers to an unsubstituted or substituted mono-, bi- or tricyclic carbocyclic ring system having one, two or three aromatic rings including but not limited to phenyl, naphthyl, anthryl, azulyl, tetrahydronaphthyl, indanyl and indenyl.

The term "heterocyclic aryl", as used herein, refers to an unsubstituted or substituted cyclic aromatic radical having from 5 to 10 ring atoms of which at least one ring atom is selected from S, O and N; the radical being joined to the rest of the molecule via any of the ring atoms. Representative, but not limiting examples are pyridinyl, pyrazinyl, pyrimidinyl, pyrrolyl, imidazolyl, thiazolyl, oxazolyl, isooxazolyl, thiadiazolyl, oxadiazolyl, thiophenyl, furanyl, quinolinyl and isoquinolinyl.

The terms "alkyl" or "cycloalkyl", as used herein, comprise any unsubstituted or substituted (cyclo)alkyl groups. Specific, but not limiting examples are an unsubstituted or substituted methyl group, ethyl group, lower (cyclo)alkyl group with 3-10 C atoms, or (cyclo)alkyl group with 11-30 or more C atoms.

The term "heterocycloalkyl" as used herein, refers to a non-aromatic 3-, 4-, 5-, 6- or 7-membered ring or a bi- or tricyclic group comprising fused 6-membered rings having between 1 and 3 heteroatoms independently selected from S, O and N, including but not limited to pyrrolidinyl, pyrazolinyl, pyrazolidinyl, imidazolidinyl, piperidinyl, piperazinyl, oxazolidinyl, isoxazolidinyl, isooxazolidinyl, morpholinyl, thiazolidinyl, isothoazolidinyl, and tetrahydrofuryl.

In a more specific embodiment of the invention, the novel compounds according to claim 1 have the basic formula II

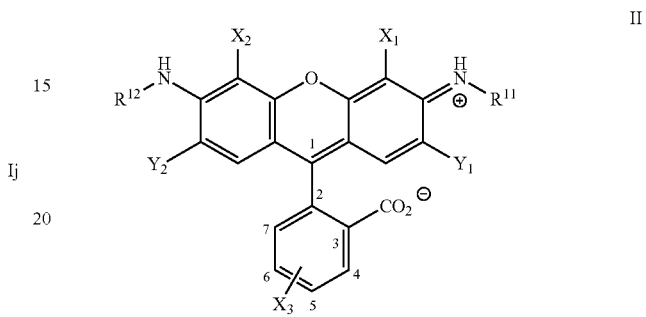

and are selected from the group of compounds 10-21 with the following substitution patterns:
10: Y$_1$=Y$_2$=F; R$_{11}$=R$_{12}$=X$_1$=X$_2$=X$_3$=H
11: Y$_1$=Y$_2$=F; R$_{11}$=R$_{12}$=X$_1$=X$_2$=H; X$_3$=COOH
12: Y$_1$=Y$_2$=F; R$_{11}$=R$_{12}$=X$_3$=H; X$_1$=X$_2$=SO$_3$H
13: Y$_1$=Y$_2$=F; R$_{11}$=R$_{12}$=H; X$_1$=X$_2$=SO$_3$H; X$_3$=COOH
14: Y$_1$=Y$_2$=X$_1$=X$_2$=X$_3$=H; R$_{11}$=R$_{12}$=CH$_2$CF$_3$
15: Y$_1$=Y$_2$=X$_1$=X$_2$=H; R$_{11}$=R$_{12}$=CH$_2$CF$_3$; X$_3$=COOH
16: Y$_1$=Y$_2$=X$_3$=H; X$_1$=X$_2$=SO$_3$H; R$_{11}$=R$_{12}$=CH$_2$CF$_3$
17: Y$_1$=Y$_2$=H; X$_1$=X$_2$=SO$_3$H; R$_{11}$=R$_{12}$=CH$_2$CF$_3$; X$_3$=COOH
18: Y$_1$=Y$_2$=F; X$_1$=X$_2$=X$_3$=H; R$_{11}$=R$_{12}$=CH$_2$CF$_3$
19: Y$_1$=Y$_2$=F; X$_1$=X$_2$=H; R$_{11}$=R$_{12}$=CH$_2$CF$_3$; X$_3$=COOH
20: Y$_1$=Y$_2$=F; X$_1$=X$_2$=SO$_3$H; R$_{11}$=R$_{12}$=CH$_2$CF$_3$; X$_3$=H
21: Y$_1$=Y$_2$=F; X$_1$=X$_2$=SO$_3$H; R$_{11}$=R$_{12}$=CH$_2$CF$_3$; X$_3$=COOH
22: Y$_1$=Y$_2$=X$_1$=X$_2$=H; R$_{11}$=R$_{12}$=CH$_2$CF$_3$; X$_3$=COOMe In another specific embodiment, the novel compounds according to claim 1 have the basic structural formula III

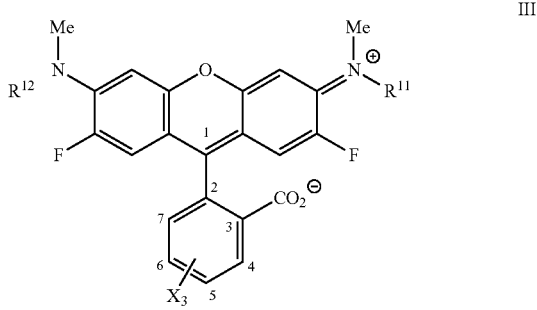

and are selected from the group of compounds 23-28 with the following substitution patterns:
23: R$_{11}$=R$_{12}$=X$_3$=H
24: R$_{11}$=R$_{12}$=H; X$_3$=COOH
25: R$_{11}$=R$_{12}$=CH$_2$CF$_3$; X$_3$=H
26: R$_{11}$=R$_{12}$=CH$_2$CF$_3$; X$_3$=COOH
27: R$_{11}$=R$_{12}$=Me; X$_3$=H
28: R$_{11}$=R$_{12}$=H; X$_3$=COOH A further aspect of the invention relates to various advantageous uses of the present compounds of the structural formulae Ia-Ij. Due to their favourable characteristics, these compounds represent efficient fluorescent dyes and markers.

The new fluorescent dyes emit light at about 520 nm or longer wave lengths, possess high values of the fluorescence quantum yields in solution, relatively long excited state lifetimes (>3 ns), are very resistant against photobleaching under STED conditions (by depletion with very strong light at about 600 nm) in the presence of air-oxygen and exhibit relatively low rates of intersystem crossing. In particular, they perform very well in conventional and stimulated emission depletion (STED) microscopy and fluorescence correlation spectroscopy, especially with very high light intensities. They possess advantageous GSDIM parameters, such as recovery times of ca. 150-450 ms, low content of the dye in the ground state after the pump pulse, and their recovery to the fluorescent ground state may be enhanced by the irradiation with the UV laser (375 nm). Moreover, these compounds as such or after introduction of reactive sites such as amino or thio functional groups or other suitable groups known in the art can be readily coupled to other molecules, in particular biomolecules such as peptides, proteins, lipids, carbohydrates, nucleic acids, or toxins, and the resulting bioconjugates can be used as fluorescent dyes or markers as well.

Thus, the present invention provides the use of compounds according to any one of claims 1-3 or any of their stable conjugates with biomolecules or any other chemical substances such as peptides, proteins, lipids, carbohydrates, nucleic acids, toxins, etc. as fluorescent dyes. More specifically, the present invention provides the use thereof in the fields of spectroscopy or microscopy, such as reversible saturable optically linear fluorescent transitions (RESOLFT) microscopy, in particular stimulated emission depletion (STED) microscopy, fluorescence correlation spectroscopy (FCS), ground state depletion with individual molecular return (GSDIM) imaging, fluorescence recovery after photobleaching (FRAP) technique, fluorescence life-time imaging (FLIM), resonance energy transfer (RET) studies [Förster resonance energy transfer (FRET) method], or conventional microscopy, e.g. as fluorescent dyes penetrating through cell membranes of living cells.

The present invention also provides the use of hydrophilic compounds of any one of claims 1-3 in free form or attached to antibodies or other biomolecules for microinjections into cells and for immunostaining applications. As demonstrated with the exemplary compounds 15 and 17, respectively, in Example 10, their conjugates with antibodies produce a very low background in immunostaining experiments due to the low affinity of the dyes to intracellular components.

In a further aspect, the present invention also provides improved methods for producing compounds of the general formula I. One specific embodiment provides a method for the synthesis of 4,5-disulfono-3,6-bis[N,N'-(2,2,2-trifluoroethyl)amino]xanthenes Ib,e or 4-sulfono-6-amino-3-[N'-(2,2,2-trifluoroethyl)amino]xanthene derivatives Ig,j by direct sulfonation of the corresponding unsulfonated N[,N'-bis](2,2,2-trifluoroethyl)-substituted 3,6-diaminoxanthene derivative at positions 4 and 5 in the course of a one-step procedure by reacting with a sulfonating agent, e.g. $SO_3$, $SO_2Cl_2$, etc.

In another specific embodiment, the present invention provides a method for preparing rhodamine amides bearing two sulfonic acid residues in the positions 4 and 5 of the xanthene fragment according to formulae Ib,d,e,g,i,j above or formula IV below

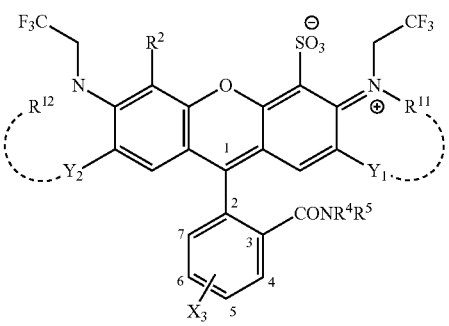

wherein in the formula IV $R^2$=H or $SO_3H$, the pairs of substituents $R^{11}$—$Y_1$, $R^{12}$—$Y_2$ independently denote any branched or unbranched alkyl or alkenyl chain or any combination of the said chains with a cycloalkyl, heterocycloalkyl, aryl, heterocyclic aryl group, or any functionally substituted alkyl, cycloalkyl, aryl, heterocyclic aryl group; $X_3$=H, 5-COOH or 6-COOH or an ester thereof, and wherein $R^4$ and $R^5$ is (are) hydrogen atom(s), any alkyl, cycloalkyl, heterocycloalkyl, aryl, heterocyclic aryl group, or any functionally substituted alkyl, cycloalkyl, aryl, heterocyclic aryl group, or any combination of the said groups, by reacting of the corresponding unsulfonated rhodamine amides having hydrogen atoms in the said positions with oleum in the course of a one-step procedure under temperature conditions which leave the amide bond intact.

Preferably, the reaction is conducted at a temperature in the range from −5 to +20° C., more preferably from 0 to +4° C.

In one specific example of this reaction, compound 14a has been converted into compound 16a.

Moreover, the compounds disclosed in the present invention or any of their conjugates with biomolecules, e.g. amino acids, peptides, proteins, lipids, carbohydrates, nucleic acids, toxins, etc., or any other chemical substances may be advantageously used as molecular probes, since the absorption and/or emission spectra and/or fluorescence quantum yields or lifetimes of these compounds are changed in response to a change in the polarity of a medium or microenvironment (e.g. solvent, protein or protein domain, (lipid) membrane, ion-channel, etc.). The data in table 2 show that detectable spectral changes occur already by changing the solvent from methanol to water.

The change of the absorption and/or emission spectra of the molecular probes may for example involve a change in the positions, shape and/or relative intensity of the bands of the absorption and/or emission spectra of the compounds used as the molecular probes.

Structures of the New Fluorinated Rhodamines, General Features and Principles of their Assembly Scheme 3. Numbering of the carbon atoms in the xanthene fragment

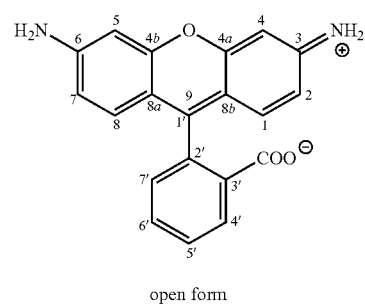

open form

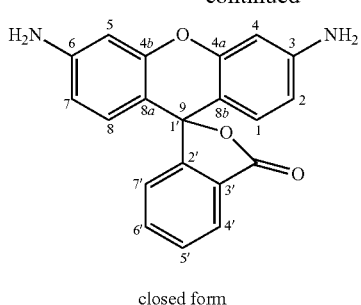

closed form

Many of the claimed rhodamine dyes and most of the exemplary compounds synthesized so far (10-13 and 18-28) have two fluorine atoms at the positions 2' and 7' of the xanthene fragment. This is a quite new structural element in rhodamines and no data on 2,7-difluorosubstituted 3',6'-diaminoxanthenes have been reported in the literature. However, fluorinated rhodol derivatives have been disclosed (WO 97/39064). Rhodols-3'-amino-6'-hydroxy-xanthenes—have lower absorption coefficients than the corresponding fluoresceins or rhodamins and their fluorescent quantum yields are lower than these of fluoresceins (P. R. Hammond, *J. Photochem.* 1979, 10, 467-471). Rhodol derivatives found some use only as sensor for metal ions, but not as bright and photostable fluorescent dyes.

Another new and important feature is a combination of the two 2,2,2-trifluoroethyl substituted amino groups at the positions 3' and 6' together with the two sulfonic acid residues at the positions 4' and 5' of the xanthene ring (compounds 16 and 17). In 1989 and 1991 a very limited number of N,N'-bis(2, 2,2-trifluoroethyl)-3',6'-diaminoxanthenes have already been disclosed as photostable analogues of Rhodamine 6G (U.S. Pat. Nos. 4,945,176, 5,047,559, 5,111,472), but these compounds do not anticipate any of the compounds presented here.

The 2,2,2-trifluoroethyl residue was chosen as a substituent for the amino group for the following reasons. In some respects, it behaves like a hydrogen atom. For example, 2,2, 2-trifluoropropionic acid ($CF_3 CH_2 COOH$) is as strong as formic acid (HCOOH). This means that the electronic inductive effect of the $CF_3 CH_2$-group is equal to the inductive effect of the hydrogen atom. Therefore, all derivatives of rhodamine 110 encompassed by formula II (compounds 10-21) are expected to have the same absorption and emission spectra as the parent dye. Fluorination is known to increase lipophilicity and reduce the solubility in water. Sulfonation compensates this effect and restores the hydrophilic properties of the dyes, providing a fairly good solubility in water. Sulfonation is known to shift very slightly both the absorption and the emission bands to the blue (up to ca. 5 nm), so it does not alter the spectral properties considerably. It was found that the presence of one $CH_2 CF_3$ group at the nitrogen atom in rhodamine does not inhibit the sulfonation with $SO_3$ in $H_2 SO_4$. On the other hand, the $NHCH_2 CF_3$-groups in the derivatives of amino acid are resistant to acylation (in the presence of "normal" primary amines) [S. Bigotti, A. Volonterio, M. Zanda, Synlett 2008, 958-962]. Thus, this group provides sufficient chemical protection for the amino group, and it also reduces the number of NH-atoms prone to photobleaching reactions. It was already mentioned that the photostability of rhodamines depend on the substitution pattern of the nitrogen atoms.

Comparison of rhodamine 6G (with disubstituted nitrogens), tetramethyl rhodamine (TMR; with trisubstituded nitrogen atoms) and methyl ester of rhodamine 110 (with monosubstituted nitrogens) showed that at low light intensities (up to $10^3$ W/cm$^2$) TMR was the most stable dye. Photobleaching quantum yields in water were found to be 12, 3.3 and $6.6 \times 10^{-7}$, respectively [C. Eggeling, J. Nidengren, R. Rigler, C. A. M. Seidel, *Anal. Chem.* 1998, 70, 2651-2659]. It is interesting that under these conditions, methyl ester of rhodamine 110 bleached slower than rhodamine 6G, though the degree of substitution at the nitrogen atoms of latter compound is higher. This fact may be explained by the presence of two methyl groups at the positions 2' and 7' of rhodamine 6G: they block the carbon atoms of the xanthene heterocycle, but, at the same time, these methyl groups may give rise to the relative stable benzylic radicals—good carriers in the chain radical processes during photobleaching. At high light intensities (up to $10^7$ W/cm$^2$) TMR was invariably 4-5 times more stable than rhodamine 6G.

Scheme 4. Equilibrium between fluorescent (open) and non-fluorescent (closed) forms in rhodamines depends on pH.

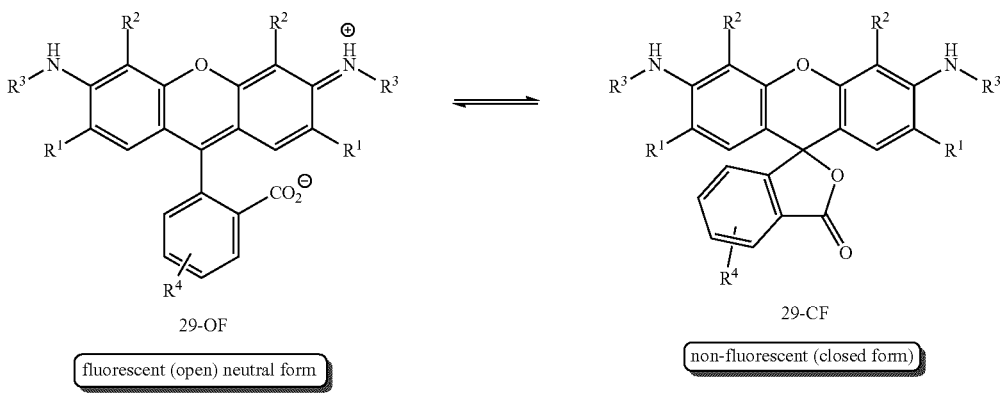

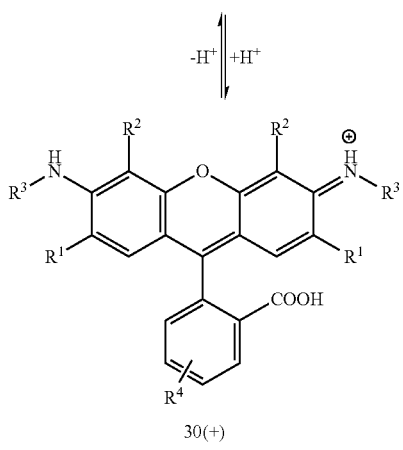

$R^1 = H, F; R^2 = H, SO_3H;$
$R^3 = H, CF_2CH_2;$
$R^4 = H, COOH$

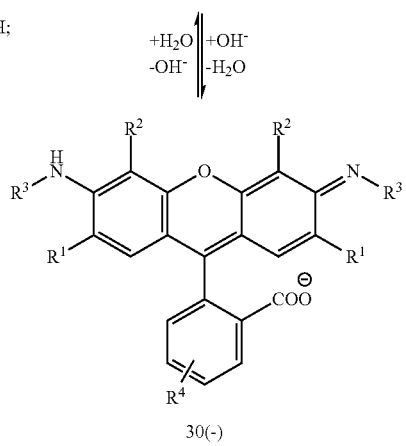

30(+)

fluorescent (open) acidic form

30(−)

fluorescent (open) basic form

An equilibrium between the "open" fluorescent (29-OF) and the "closed" non-fluorescent (29-CF) forms in rhodamines is shown in Scheme 4. In the case of fluorinated rhodamines introduced in the present research proposal the non-fluorescent closed form (29-CF) may prevail, due to the strong-I-effect of the fluorine atoms, which destabilize the positively charged xanthene fragment of the zwitter-ionic open form. However, in the strongly acidic and basic media, the equilibria shift to the acidic and basic open forms 30(+) and 30(−), respectively (Scheme 4). Sulfonation ensures the presence of only one fluorescent form, because the strongly acidic sulfonic acid group easily protonates the carboxylate anion. Therefore, sulfonation is highly desirable to avoid the closed non-fluorescent form. To generate the open acidic fluorescent form, it is necessary to filter the aqueous solutions of sulfonated rhodamines through the $H^+$-form of the strongly acidic ion-exchange resin and then lyophilize the solutions.

It was already mentioned that the modern optical filters allow to distinguish between two spectral bands which are only 10 nm apart. This shift may easily be realized within the subsetset (10-21) of the proposed fluorescent dyes simply by changing the position of the (amino) reactive group. Higher sterical availability and therefore, higher reactivity of the "remote" carboxylic group at the position 5 or 6 of the benzoic acid residue enables to selectively activate this group, keeping the sterically hindered carboxylate intact (formula II, $R^4$=amino reactive (activated) ester group). In this case the absorption and emission maxima do not change. On the other hand, fluorophores without the second carboxylate require an additional linker for connecting the sole carboxylic group with a reactive site (Scheme 5).

Scheme 5. Amidation of the sole carboxylate in rhodamines. Coupling reagents: O-(7-azabenzotriazol-1-yl)-N,N,N′,N′-tetramethyluronium*$PF_6^-$ (HATU), N,N,N′,N′-tetramethyl-O-(N-succinimidyl) uronium*$BF_4^-$ (TSTU), N,N′-dicyclohexylcarbodiimide (DCC).

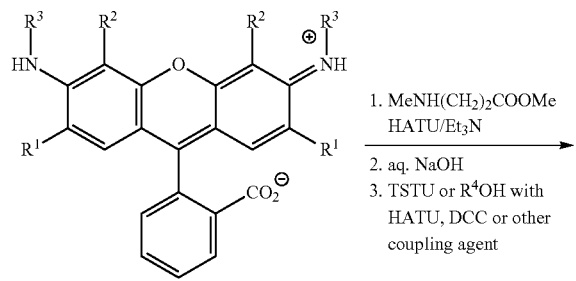

10, 12, 14, 16, 18, 20

1. MeNH(CH$_2$)$_2$COOMe HATU/Et$_3$N
2. aq. NaOH
3. TSTU or $R^4$OH with HATU, DCC or other coupling agent

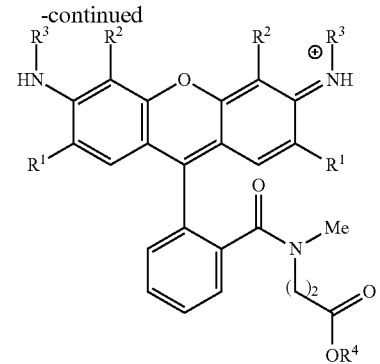

10a, 12a, 14a, 16a, 18a, 20a $R^1 = H, F; R^2 = H, SO_3H; R^3 = H, CF_2CH_2;$

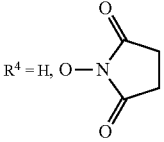

or another active ester group
$n = 2, 3$

Amidation of the sole carboxylate in rhodamines with methyl esters of the ω-(N-methylamino) carboxylic acids provides the corresponding secondary amides with a required red shift of 10 nm in both absorption and emission bands, and based on previous works of the group of the present inventors (M. Bossi, V. Belov, S. Polyakova, S. W. Hell, *Angew. Chemie* 2006, 118, 7623-7627; *Angew. Chem. Int. Ed.* 2006, 45 (44), 7462-7465) it is not expected that the $\Phi_{fl}$-values will decrease drastically. Interestingly, the corresponding pairs of dyes (e.g. 10 and 10a) represent the ideal FRET-pairs, because the emission band of the starting material (10) overlap with the absorption band of the product (10a), the secondary amide. This spectral shift achieved without changing the fluorophore structure (as mentioned above, in the case of Alexa Fluor® and Oregon Green® dyes structural changes were necessary for shifting the absorption bands from 488 to 514 nm) may enable to resolve the fluorescence bands of bioconjugates, obtained from the active esters 10a-20a, and the active esters, prepared from the corresponding dicarboxylic acids 11, 13, 15, 17, 19 or 21 (formula II). Certain spectral imaging instruments (e.g. Zeiss META® system) with linear unmixing software resolve the strongly overlapped emission bands.

Additional methylation of the amino groups in compounds 23-28 (formula III) provides a strong red shift of 25-30 nm in the absorption and emission maxima. Unfortunately, rhodamines 23-28 cannot be directly sulfonated.

The secondary amide group in compounds 10a-20a prevents the spontaneous cyclization into a colourless closed form. Methyl esters of ω-(N-methylamino)carboxylic acids [MeNH(CH$_2$)$_n$COOMe] are readily available. For example, the preparation of methyl 3-(N-methylamino)propionate and its typical transformations, similar to those depicted in Scheme 5, have been reported (V. P. Boyarskiy, V. N. Belov, R. Medda, B. Hein, M. Bossi, S. W. Hell, *Chem. Eur. J.* 2008, 14, 1784-1792). Protection of the aromatic amino groups with 2,2,2-trifluoroethyl substituents enables using much more stronger activators of the carboxylic group than HATU, TSTU or carbodiimide. Phosphorous oxychloride (POCl$_3$) at ca. 90° C. or oxalyl chloride [(COCl)$_2$] at room temperature transform carboxylic groups into the corresponding acid chlorides, and during this procedure the protonated and positively charged CF$_3$ CH$_2$ NH-groups are not prone to acylation. After evaporation of the excess of the activating agents in vacuo, the corresponding acid chlorides have to be dissolved in an appropriate solvent and react with secondary amine. At this point and under basic conditions, the protection of the amino groups starts to be essential. Sulfonic acid residues also react with POCl$_3$ by heating and give sulfonyl chlorides. For that reason conversion into the acid chlorides should not be carried out for the substrates 12, 16 and 20 (formula II). However, after coupling with MeNHCH$_2$ CH$_2$OOMe, rhodamines 10, 14 and 16 may be sulfonated with 30% SO$_3$ in H$_2$ SO$_4$ at 0° C.: under these conditions the secondary amide group was found to be quite stable, though the methyl ester is partially cleaved off.

General Synthesis of the Novel Fluorinated Rhodamines of the Invention

Synthetic routes to the new fluorinated rhodamines are given in Schemes 6-10. Commercially available 2-fluoro-5-nitroaniline was used as a starting material (Scheme 6).

First it was transformed to N-methyl-(32-NO$_2$-Me) and N,N-dimethylaniline 31-NO$_2$, and then the nitro group in these compounds and in the intermediate 32-NO$_2$—H was reduced (Schemes 7 and 8).

Scheme 6: Preparation of 2-fluoro-5-nitroanilines 31-NO$_2$ and 32-NO$_2$: a) 35% aq. H$_2$CO, NaBH$_4$, THF, 3 M aq. H$_2$SO$_4$, room temp.; b) (CF$_3$CO)$_2$O, CH$_2$Cl$_2$, Et$_3$N, 0° C. → room temp., overnight; c) MeI, K$_2$CO$_3$, DMF, 90° C., 24 h.

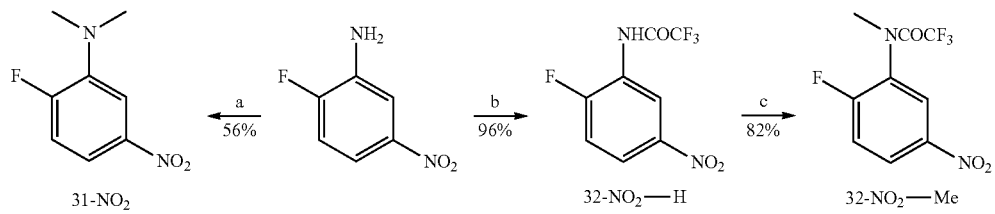

The next important step included the diazotation of the anilines —NH$_2$—R (Scheme 7) and 31-NH$_2$ (Scheme 8) followed by the transformation of diazonium salts into phenols 32-OH—R and 31-OH under very mild conditions (Th. Cohen, A. G. Dietz Jr., J. Miser, *J. Org. Chem.* 1977, 42, 2053-2058). Compound 31-OH was used directly in the synthesis of rhodamine 37-Me-Me-H (with one carboxylic acid group) and the mixture of regioisomers-rhodamines 37-Me-Me-COOH and 38-Me-Me-COOH with two carboxylic acid groups (Scheme 8).

Scheme 7. Synthesis of 2,7-difluoro-N, N'-bis (2,2,2-trifluoro-ethyl) rhodamines 33 and 35: a) 10% Pd/C, H$_2$, EtOAc, room temp., 7 h; b) aq. NaNO$_2$, 35% aq. H$_2$SO$_4$, 0° C., then aq. Cu(NO$_3$)$_2$×3H$_2$O, Cu$_2$O, room temp.; c) 1 M BH$_3$*THF, THF, 0→90° C., 24 h; d) fused ZnCl$_2$, 180-200° C., 3-4 h.

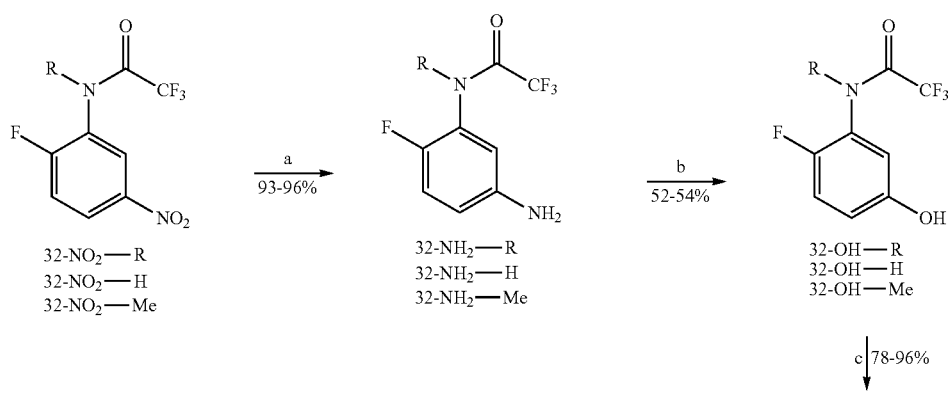

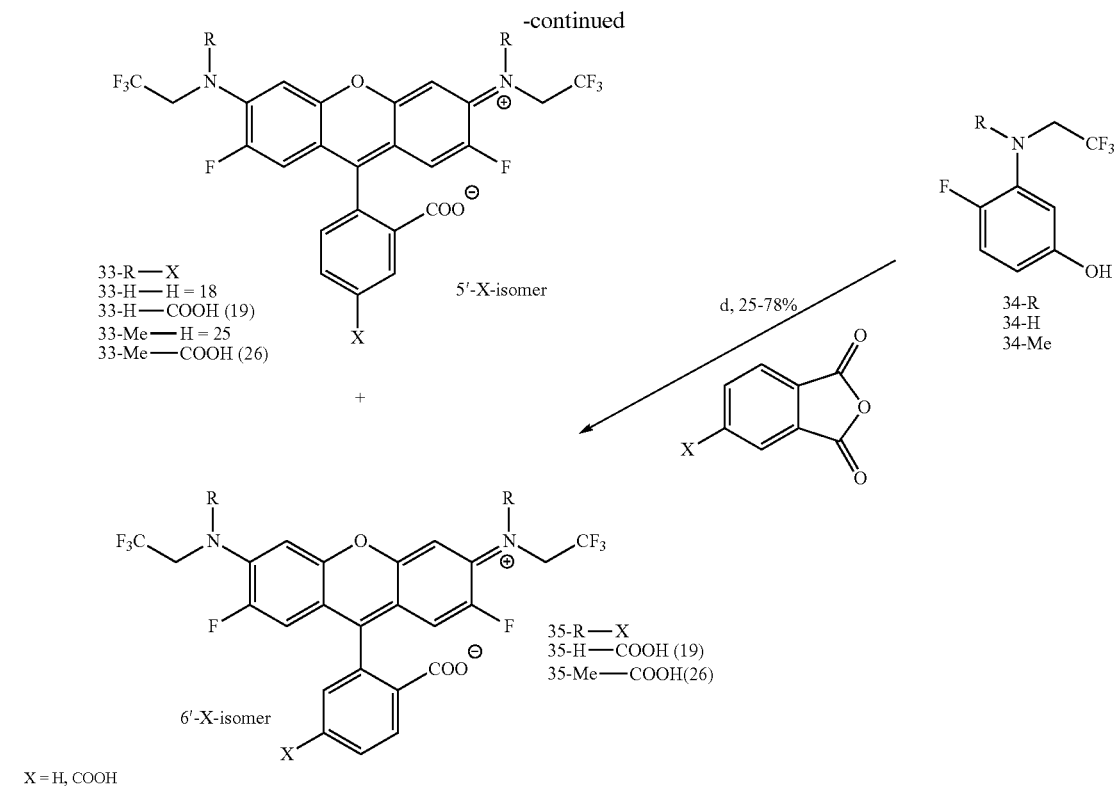

N-Trifluoroacetylated m-aminophenols 32-OH—R (Schemes 7 and 8) were the key intermediates for the following transformations. They were either reduced to 3-hydroxy-N-(2,2,2-trifluoroethyl)anilines 34-R (Scheme 7), or deprotected to anilines 36-R¹ (Scheme 8). m-Aminophenols 34-R and 36-R¹ were condensed with phthalic or trimellitic anhydrides, and rhodamines 33-H—H, 33/35-H—COOH, 33-Me-H, 33/35-Me-COOH, 37-H—H—H, 37/38-H—H—COOH, 37-Me-H—H and 37/38-Me-H—COOH were obtained. All rhodamines mentioned above were obtained in the course of the condensation reaction in the presence of fused anhydrous ZnCl$_2$ and isolated from the reaction mixtures by column chromatography on silica gel. Yields were moderate. Other condensation agents were found to give inferior results.

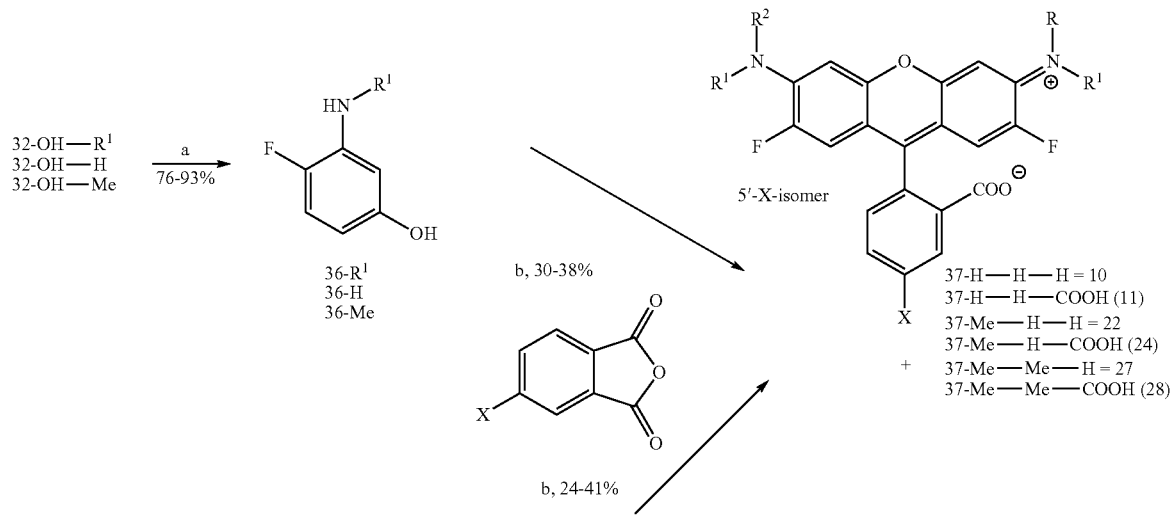

Scheme 8. Synthesis of 2, 7-difluororhodamines 37 and 38: a) 30% aq. NaOH, MeOH, 90° C., 24 h; b) fused ZnCl$_2$, 180-200° C., 3-4 h; c) 10% Pd/C, H$_2$, EtOAc, room temp., 7 h; d) aq. NaNO$_2$, 35% aq. H$_2$SO$_4$, 0° C., then aq. Cu(NO$_3$)$_2$×3H$_2$O, room temp.

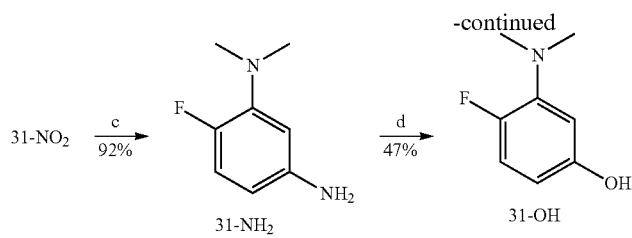
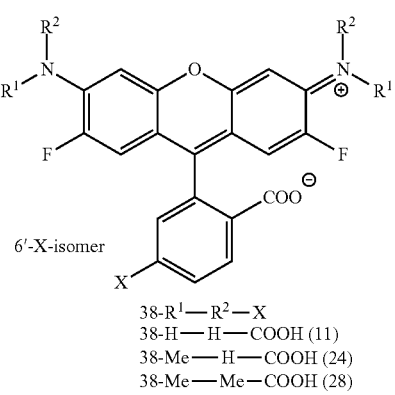

X = H, COOH

Similarly, m-methoxyaniline was transformed N-(2,2,2-trifluoroethyl)-3-methoxyaniline (40) (Scheme 9). O-Demethylation with 48% aq. HBr in acetic acid afforded N-(2,2,2-trifluoroethyl)-3-hydroxyaniline (41) which after condensation with phthalic or trimellitic anhydrides yielded rhodamines 42-H or the mixture of rhodamines 42-COOH and 43-COOH, respectively. In this case the first step of the condensation procedure was performed by heating the finely grounded mixture of the anhydride with the corresponding 3-hydroxyaniline without any additional reagent. Under these conditions, phthalic or trimellitic anhydride acylates 3-hydroxyaniline at the position 4 (C-4). Then the "second half" of the amine 41 was added, together with 85% aq. $H_3PO_4$, and heating was continued. Rhodamine 42-H precipitated from the reaction mixture, after it was cooled down and diluted with aq. MeOH. Pure product may easily be obtained by additional recrystallization from aq. MeOH. Repeated recrystallization of the mixture 42/43-COOH from aq. iPrOH affords the regioisomer 42-COOH (with content of 43-COOH less than 4%). Evaporation of the combined mother liquids followed by RP-chromatography with MeOH/$H_2O$ mixture (1:4) gave the second pure isomer (43-COOH).

Scheme 9. Synthesis of N,N'-bis(2,2,2-trifluoroethyl)-rhodamines 42, 43 and their esters 44, 45 and 46:

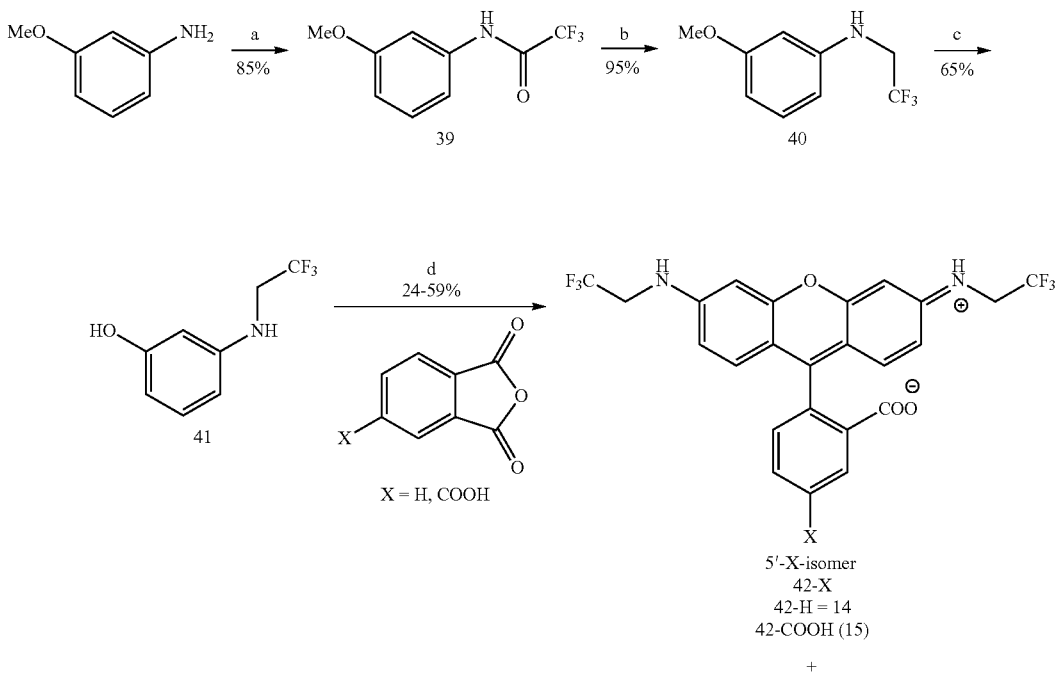

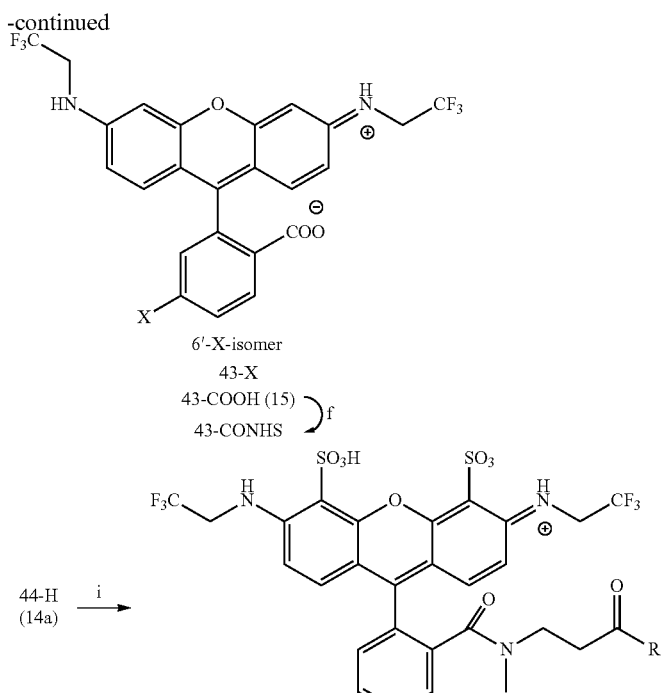
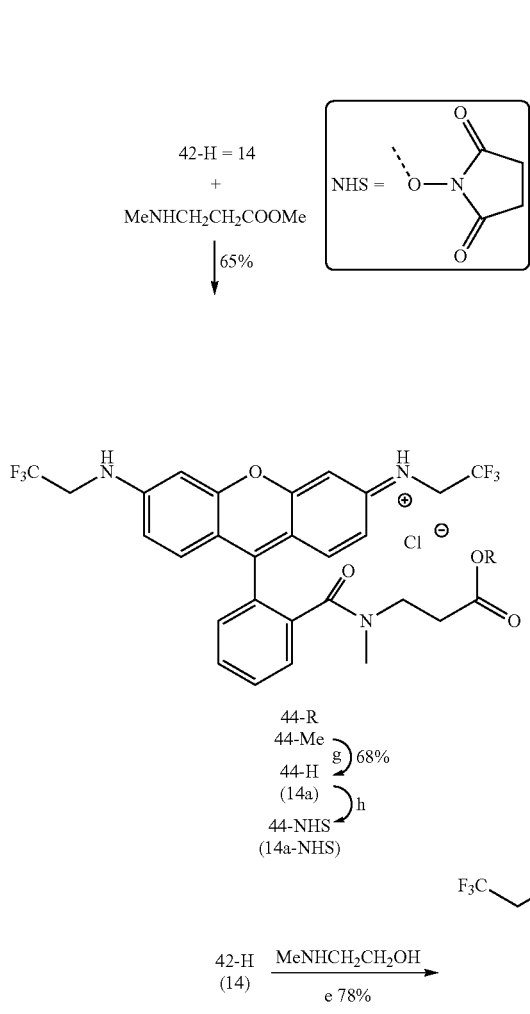

a) (CF₃CO)₂O, CH₂Cl₂, Et₃N, 0° C. → room temp., overnight; b) 1M BH₃*THF, THF, 0 → 90° C., 24 h; c) 48% aq. HBr, AcOH, reflux, 6 h; d) 160° C., 3 h, then 2$^{nd}$ half of 41, 85% aq. H₃PO₄, 160° C., 3 h; e) POCl₃, 1,2-dichloroethane, reflux, 4 h; HCl*H₂NCH₂COOMe, Et₃N, MeCN, room temp., 20 h; f) N-hydroxysuccinimide, O-(7-azabenzotriazol-1-yl)-N,N,N',N'-tetramethyluronium*PF₆⁻ (HATU), DMF, room temp., overnight; g) 1M aq. NaOH, MeOH, THF, 0° C., → temp., 2 h; h) N,N,N',N'-tetramethyl-O-(N-succinimidyl)uronium*BF₄⁻ (TSTU), Et₃N, DMF, room temp., 24 h; i) 30% SO₃ in H₂SO₄, 0° C., 2-3 days.

Further methods for derivatizing the monocarboxy rhodamines 33-H—H, 37-H—H—H, 37-Me-H—H, 37-Me-Me-H and 42-H were used. For that, rhodamine 42-H was converted into the corresponding acid chloride, and the latter reacted with methyl 3-[(N-methyl)amino]propionate or 2-[N-(methylamino)]ethanol (Scheme 9). Saponification of the methyl ester 44-Me smoothly gave the acid 44-H which was transformed into the NHS-ester 44-NHS. (N,N'-Disuccinimidylcarbonate in the presence of a base transforms alcohol 46 into the corresponding NHS-carbonate.) Rhodamines with two carboxylic groups (e.g. 43-COOH) react with one equivalent of N-hydroxysuccinimide and HATU, or with 1 equivalent of N,N,N',N'-tetramethyl-O—(N-succinimidyl)-uronium*BF₄⁻ (TSTU) in the presence of a base (Scheme 5) and yield mono NHS-esters with the sterically less hindered carboxylic group activated by the formation of an ester with a good leaving group (e.g. 43-CONHS).

It was observed that the secondary amide group in rhodamines is quite stable under sulfonation conditions (30% SO₃ in H₂ SO₄, 0° C.) for several days. Thus, sulfonation of the acid 44-H affords disulfonic acid 45-OH with intact amide bond (Scheme 9). It was found to be easier first to obtain the corresponding amide and then to sulfonate it than to perform the reversed procedure, which requires two tedious reversed phase chromatographic separations instead of one and by which the yield at the amidation step is lower. Luckily, N-(2, 2,2-trifluoroethyl) substituents did not prevent the sulfonation reaction, and the corresponding disulfonic acids (46-H-CH₂ CF₃—H—H, 46-H—CH₂ CF₃—F—H, 46-H—CH₂ CF₃—H-5'-COOH, 46-H—CH₂ CF₃—F-5'/6'-COOH) were obtained (Scheme 10).

Activation of the carboxylic groups in rhodamines may be achieved by the formation of the active esters (e.g. NHS-esters 44-NHS, 45-NHS, 46-H—CH₂ CF₃—H-5'-CONHS). Together with compound 43-CONHS, these esters were used in bioconjugation reactions (see below).

Stepwise condensation reaction exemplified in Scheme 9 enables the synthesis of the unsymmetrical rhodamines (3', 6'-diaminoxanthenes) with an unprecedented combination of two substituents in the same "xanthene half": either one fluorine atom at the position 2' (7') and one N'-(2,2,2-trifluoroethyl) group, or one N'-(2,2,2-trifluoroethyl) group with one sulfonic acid residue at C-4' (5'), or one fluorine atom at the position 2'(7') and one sulfonic acid residue at C-4'(5').

(e.g. 37-Me-Me-H (27), 46-H—H—F—H (12), 46-H—H—F—COOH (13), 46-H—CH$_2$CF$_3$—F—COOH (21), 37/38-Me-Me-COOH (28)) the detectable spectral changes (>5 nm) in the positions of the absorption and/or emission maxima occur by changing the solvent from methanol to water. These changes are very pronounced for compound 37/38-Me-Me-

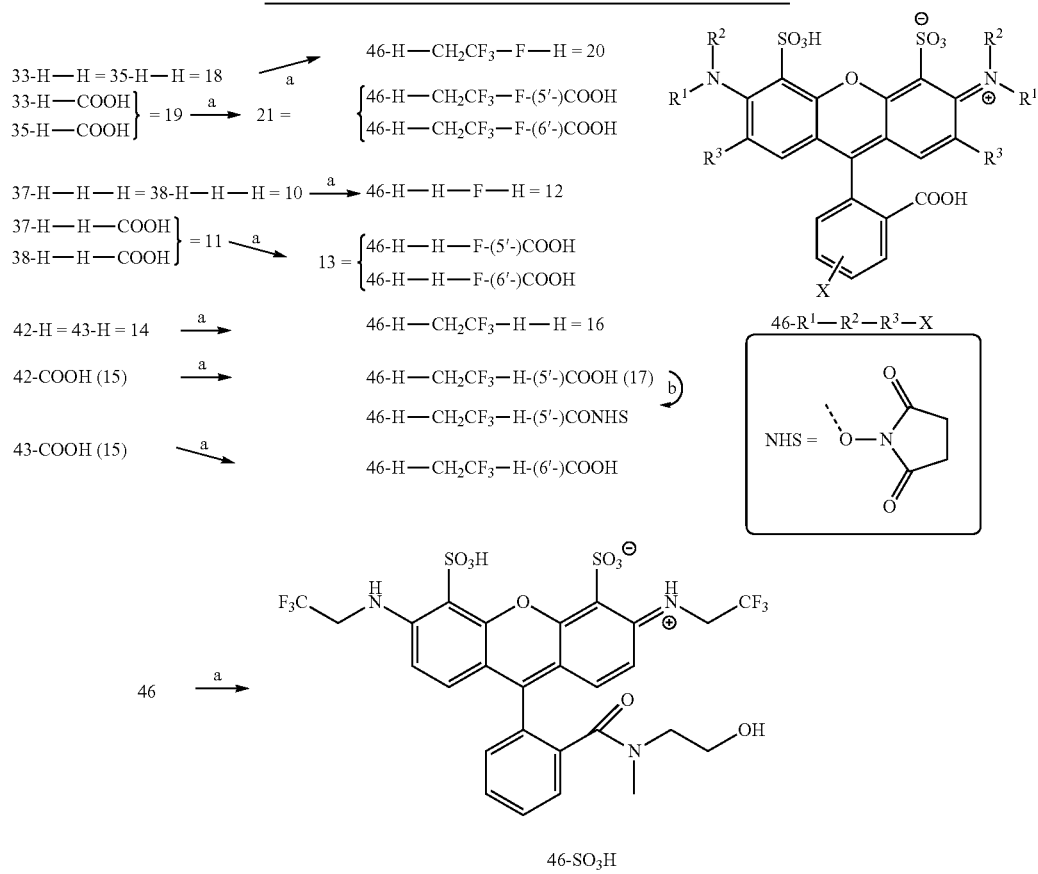

Figure 1B:
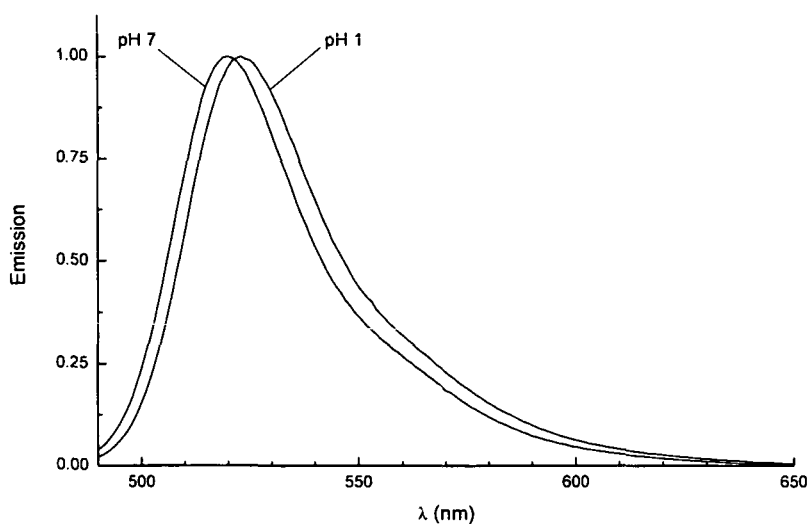

Spectral Properties and Photostability of the Fluorinated and Sulfonated Rhodaminic Dyes Most of dyes of the present invention are highly fluorescent and all of them are photostable compounds in water, aqueous buffers, alcohols and typical mounting media used in standard fluorescence microscopy techniques, such as polyvinyl alcohol (PVA), or its mixtures with water and glycerol. The majority of the compounds has absorption maxima between 480 and 515 nm and emit in the 510-535 nm region. Their solutions are yellow or light orange in daylight and have a yellow-greenish or yellow emission when excited with blue light. Compounds 33-Me-H (25), 37-Me-Me-H (27) and 37/38-Me-Me-COOH (28) absorb and emit at 525-560 nm and 555-580 nm, respectively. Their solutions have a pink or red color. Absorption coefficients of the main, long wavelength maximum for all compounds are in the order of 2×10$^4$ to 9×10$^4$ M$^{-1}$ cm$^{-1}$. An example of the absorption and emission spectra for compound 37-H—H—H (10) is shown in FIG. 1. The data in table 2 show that for some compounds COOH (28): adding methanol to an aqueous buffer causes the bathochromic shift of 23 and 35 nm in absorption and emission maxima, respectively. Therefore, the said fluorescent dyes may be used as molecular probes changing their absorption and/or emission spectra (positions, shape and (relative) intensity of the bands), or even fluorescence quantum yields and lifetimes by changing the polarity of a medium or microenvironment. For example, rhodamine 37-Me-Me-H (27) was found to be nearly non-fluorescent in aqueous buffer, but inside the living cells the fluorescence signal became considerably stronger (Example 12, FIG. 9D).

Most of the fluorinated rhodamines presented here have high emission efficiencies with values up to 0.95, and typical fluorescent lifetimes of rhodaminic dyes of 3-4 nanoseconds. The only exception is compound 33-Me-H (25) that gives colorless solutions in methanol, water and neutral buffers, due to the presence of the non-fluorescent closed form (Scheme 1) under these conditions. In acidic solutions, this substance is present in an open acidic form (30(+) in Scheme 1) with a relatively low fluorescence efficiency. The properties of the fluorinated rhodamines are summarized in Table 2.

TABLE 2

Spectral properties of the fluorinated rhodamines in an aqueous buffer at pH 7 ([a]) and in methanol ([b]).

| COMPOUND | ABSORPTION | | EMISSION | | |
|---|---|---|---|---|---|
| | $\lambda_{MAX}$ (nm) | $\epsilon$ (M$^{-1}$ cm$^{-1}$) × 10$^{-4}$ | $\lambda_{MAX}$ (nm) | $\Phi_{FL}{}^a$ | $\tau_{FL}$ (ns)$^a$ |
| 22 (37-Me—H—H) | 513$^a$, 511$^b$ | 5.6$^b$ | 539$^a$, 537$^b$ | 0.87 | 4.0 |
| 27 (37-Me—Me—H) | 554$^a$, 546$^b$ | 5.0$^a$ | 586$^a$, 576$^b$ | 0.02 | 3.3 |
| 18 (33-H—H) | 494$^a$, 500$^b$ (292)$^{2b}$ | 4.1$^b$ | 521$^a$, 519$^b$ | 1.00 | 3.8 |
| 20 (46-H—CH$_2$CF$_3$—F—H) | 506$^a$ | 5.4$^a$ | 531$^a$ | 0.66 | 3.2 |
| 12 (46-H—H—F—H) | 488$^a$, 498$^b$ | 4.2$^b$ | 512$^a$, 514$^b$ | 0.89 | 4.0 |
| 10 (37/38-H—H—H) | 494$^a$, 498$^b$ | 4.1$^b$ | 520$^a$, 522$^b$ | 0.87 | 3.9 |
| 25 (33-Me—H) | (528)$^{1a}$ (300)$^{2b}$ | (3.2)$^{1a}$ | (557)$^{1a}$ | (0.20)$^1$ | (1.2)$^1$ |
| 26 (33/35-Me—COOH) | (523)$^{a+b}$ (291)$^{2b}$ | | | | |
| 24 (37-Me—H—COOH) | 515$^a$, 515$^b$ | 5.6$^b$ | 543$^a$, 538$^b$ | 0.86 | 4.1 |
| 19 (33-H—COOH) | 496$^a$, 498$^b$ | 5.3$^a$ | 522$^a$, 520$^b$ | 0.89 | 3.8 |
| 21 (46-H—CH$_2$CF$_3$—F—COOH) | 509$^a$, 517$^b$ | 4.2$^b$ | 533$^a$, 541$^b$ | 0.86 | 3.3 |
| 28 (37/38-Me—Me—COOH) | 525$^a$, 558$^{a+b}$ | 3.1$^a$ | 554$^a$, 589$^b$ | 0.28 | 1.6 |
| 13 (46-H—H—F—COOH) | 490$^a$, 502$^b$ | 3.2$^b$ | 514$^a$, 517$^b$ | 0.97 | 4.1 |
| 11 (37/38-H—H—COOH) | 496$^a$, 498$^b$ | 5.0$^b$ | 522$^a$, 523$^b$ | 0.92 | 4.0 |
| 16 (46-H—CH$_2$CF$_3$—H—H) | 499$^a$, 507$^b$ | 8.7$^b$ | 520$^a$, 524$^b$ | 0.88 | 3.8 |
| 14 (42/43-H) | 499$^a$ | 8.1$^a$ | 522 | 0.88 | 3.9 |
| 16a (45-OH) | 512$^a$, 517$^b$ | 7.4$^b$ | 530$^a$, 536$^b$ | 0.86 | 4.1 |
| 44-Me | 512$^b$ | 8.7$^b$ | 534$^b$ | | |
| 14a (44-H) | 510$^a$, 512$^b$ | 5.7$^a$ | 531$^a$, 534$^b$ | 0.86 | 4.2 |
| 15 (42-COOH) | 501$^a$, 500$^b$ | 8.5$^a$ | 525$^a$, 524$^b$ | 0.95 | 4.1 |
| 15 (43-COOH) | 501$^a$, 497$^b$ | 8.8$^a$ | 523$^a$, 522$^b$ | 0.93 | |
| 17 (46-H—CH$_2$CF$_3$—H-5'-COOH) | 501$^a$, 511$^b$ | 8.6$^b$ | 524$^a$, 524$^b$ | 0.96 | 3.9 |

[1]Values measured at pH 1;
[2]value for the closed form

Extinction coefficients (of the long wavelength maximum) which are lower than ca. 8×10$^4$ M$^{-1}$ cm$^{-1}$ indicate the presence of the closed non-fluorescent form. The latter has an absorption maximum at 290-300 nm, characteristic for the compounds 25 and 26. The acid-base equilibrium shown in Scheme 4, which is responsible for the absence of color and fluorescence of compound 25 in neutral solutions, was not observed for the other compounds. All other dyes presented here form colored and fluorescent solutions in a wide pH range, e.g. from 1 to 12. In acidic solutions (pH≤5), a small bathochromic shift in absorption and emission maxima (typical 5 nm) was commonly observed (FIG. 1). It may be caused by the protonation of the benzoic acid moiety. Despite this small shift, the dyes are brightly fluorescent, photostable, excitable with readily available light sources (e.g. at 488 nm or 514 nm) and detectable with high efficiency. For all the presented compounds, none or only minor changes in the spectra are observed in the biologically relevant pH region of 6-9.

Figure 2:
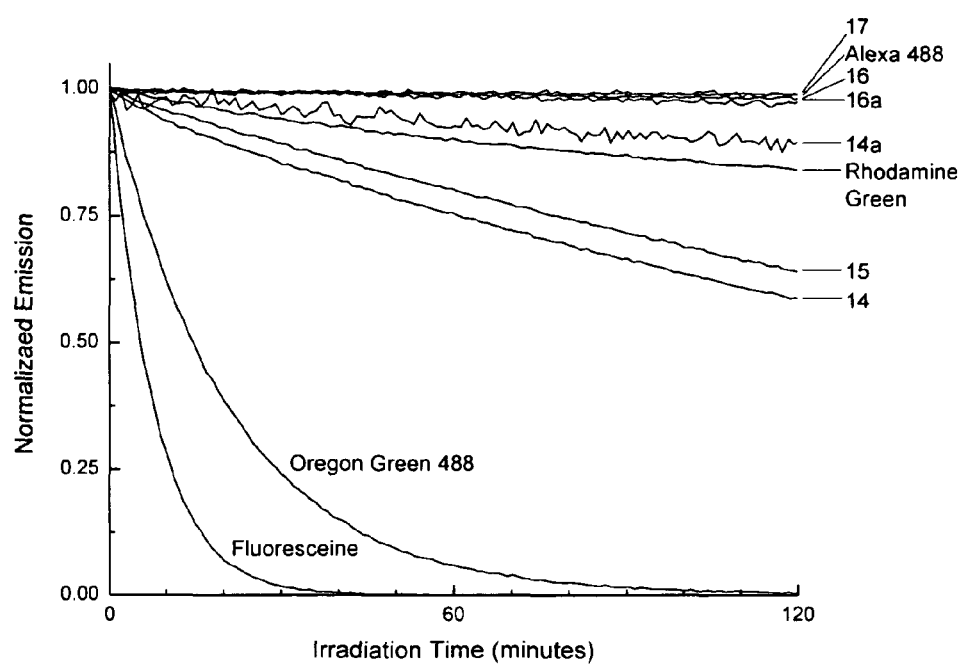

The compounds also display an outstanding photostability when irradiated for a prolonged time. FIG. 2 shows the emission intensity of the stirred solutions with micromolar concentrations of some exemplary compounds, when irradiated with 488 nm light in a 1 cm-path quartz cuvette, at an intensity of 3 W/cm$^2$. The initial absorption at the irradiation wavelength was the same for all solutions. The compounds are far more stable than the common dyes excitable at 488 nm, such as Fluorescein and Oregon Green 488®, and have similar or better performance than Rhodamine Green® or Alexa Fluor 488®. For example, colored water solutions of compounds 16, 16a, and 17 can be irradiated for several hours with the 488 nm line of an Argon laser without any significant changes in their emission. After two hours of irradiation, compounds 14 and 15 retain more than 50% of the initial emission intensity and compound 14a has about 90% of the initial signal left.

In common microscopy techniques, such as wide-field and confocal microscopy, fluorescent markers are subjected to excitation intensities that are much higher, in the range of a few kW/cm$^2$. Compounds presented here also perform outstandingly under these irradiations conditions (see, e.g. Example 11 below), proving to be useful markers for the standard fluorescence microscopy.

The invention is further illustrated by the following non-limiting Examples and Figures.

FIGURES

FIG. 1. A: absorption spectra of compound 37-H—H—H (10) in the pH range 1-7. B: excitation and emission spectra of the same compound at pH 1 and 7

FIG. 2. Photoresistance of selected compounds (14-17, 14a, and 16a in Table 2), and some commercially available fluorophores with the similar spectral properties (Alexa Fluor 488®, Rhodamine Green®, Oregon Green 488®, and Fluorescein) in aqueous solutions irradiated with 488 nm light (3 W/cm$^2$)

Figure 3:
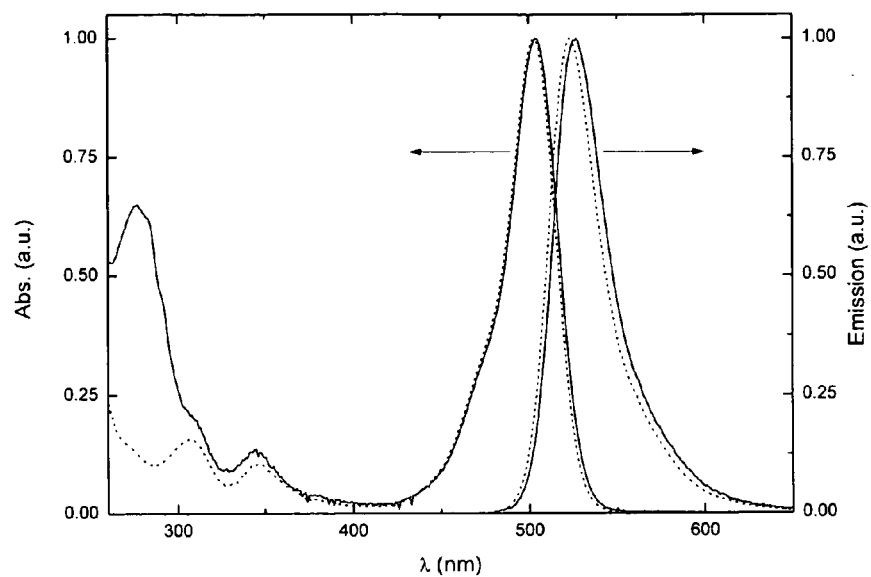

FIG. 3. Absorption and emission of compound 17 and an adduct 17-AB in PBS buffer solution FIG. 4. Depletion curves for compounds 12, 14a, 15-17, obtained in Mowiol solutions, in a STED microscope FIG. 5. STED-depletion curves of compounds 42-COOH, 43-COOH and 46-H—CH$_2$CF$_3$—H-5'/6'-COOH (A), as well as 42-H, 46 and 46-SO$_3$H (B). For comparison the depletion curves of Alexa Fluor 488® and Fluorescein are also shown.

Figure 6:
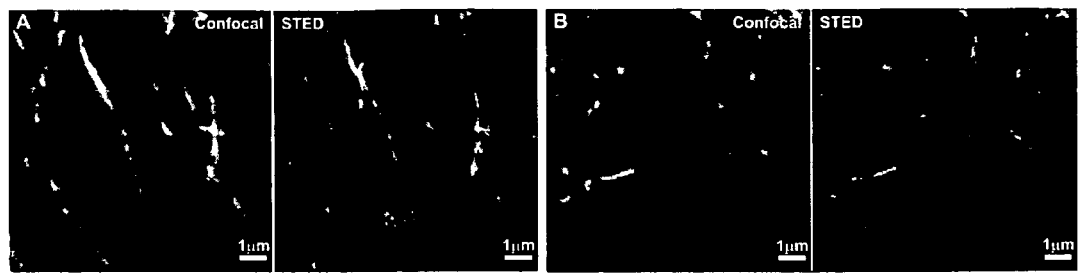

FIG. 6. Confocal and STED images of PtK2 cells immunostained with the novel fluorescent probes. A) Tubulin was bound with Anti-beta-Tubulin mouse IgG as a primary antibody and then stained with sheep anti-mouse IgG conjugated with compound 15 (as a secondary antibody); RB) Vimentin was bound with Anti-Vimentin [V9] mouse IgG and then stained with sheep anti-mouse IgG conjugated with compound 17 (as a secondary antibody)

Figure 7:
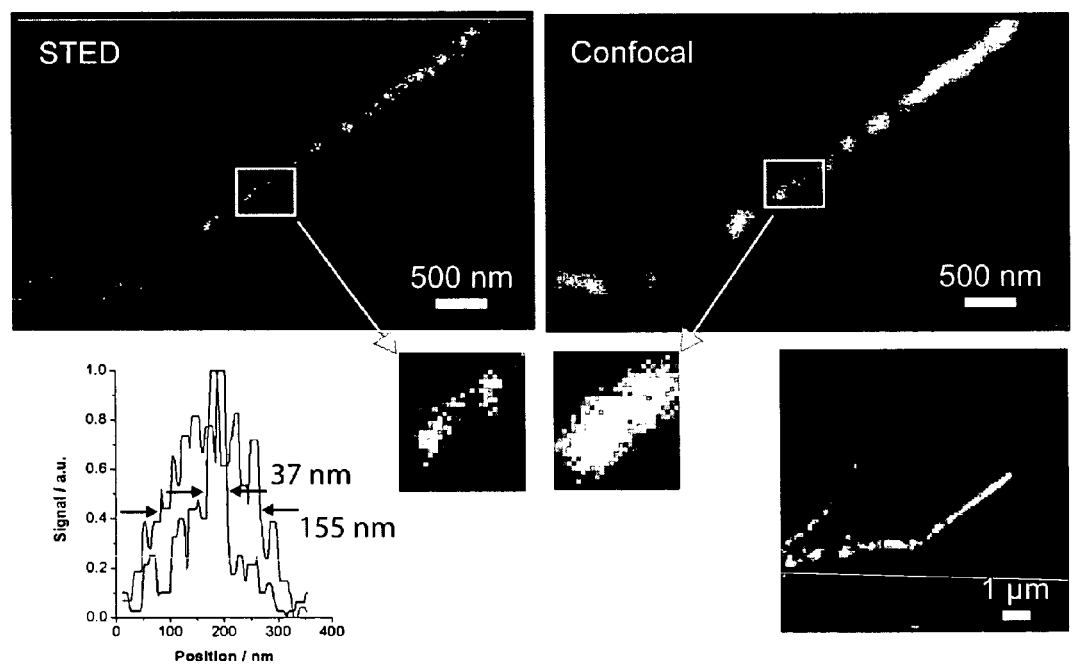

FIG. 7. STED and confocal images of Doublecortin in neurons immunostained with anti-Doublecortin rabbit IgG conjugated with the compound 46-H—CH$_2$ CF$_3$—H-5'-CONHS. Bottom right: Confocal overview image. The outtakes display the structure's Full-width-half-maximum (FWHM) within a fraction of the axon. In STED-mode the FWHM is only approx. 37 nm whereas in confocal-mode it is broadened to ca. 155 nm.

Figure 8:
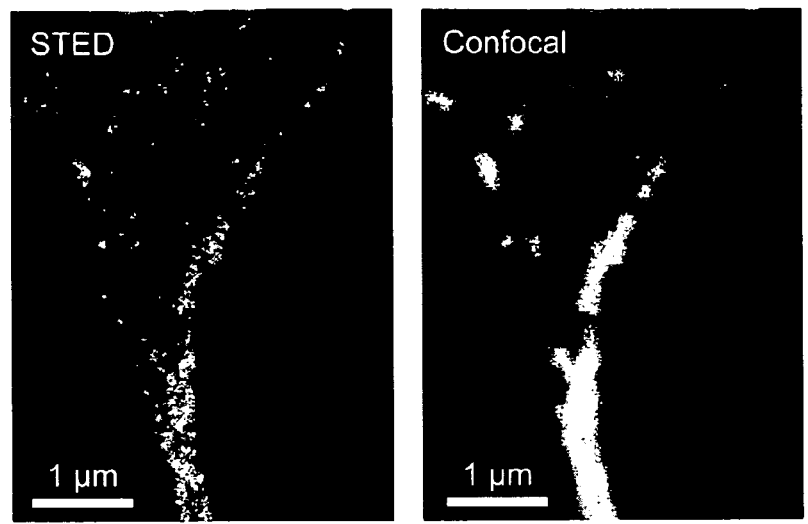

FIG. 8. STED and confocal images of Doublecortin in neurons labelled with compound 46-H—$CH_2$ $CF_3$—H-5'-CONHS (secondary antibody: anti-rabbit IgG). The resolution of the STED-image clearly outmatches the confocal resolution.

Figure 9:
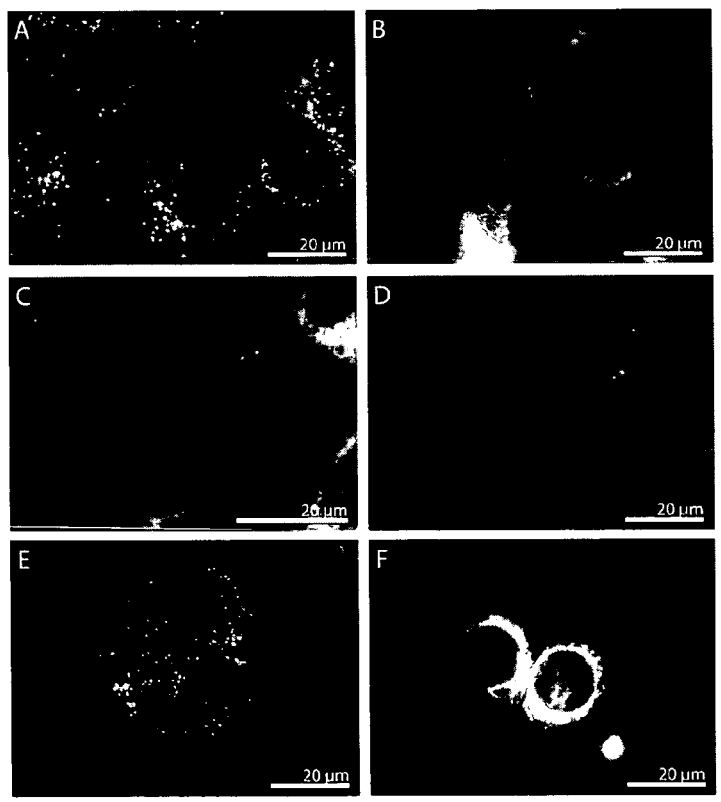

FIG. 9. Membrane-permeation experiments of the presented dyes. Living mammalian cells (PtK2) were incubated for 15 minutes with a 50 µg dye/ml solution. The subcellular localization of the dye was imaged in an epifluorescence microscope. A: 46-H—$CH_2$ $CF_3$—H—H (16); B: 42-COOH (15); C: 23; D: 37-Me-Me-H (27); E: 42-H (14)-methylester; F: 33-H—H (18).

Figure 10:
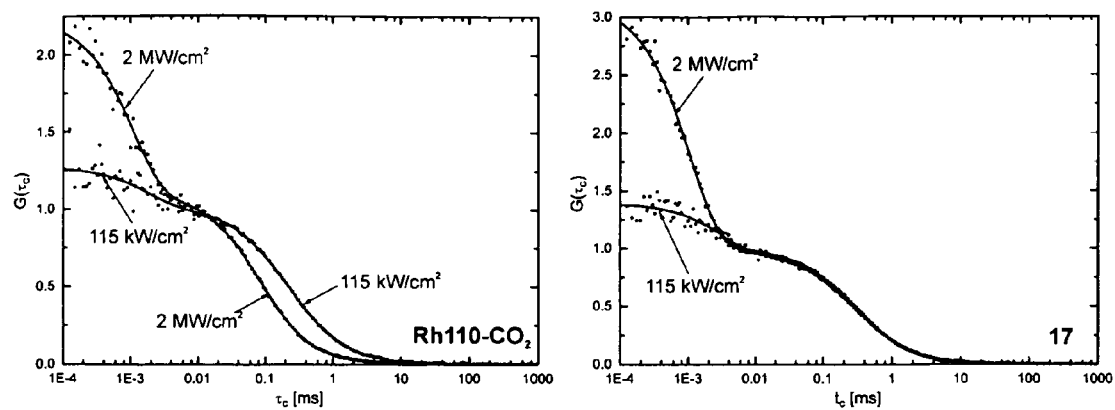

FIG. 10. FCS curves obtained from Rh110-$CO_2$ (left plot) and compound 17 (right plot), at low (0.1 MW/cm$^2$) and high (2 MW/cm$^2$) excitation intensity (dots: experimental data; lines: best fits).

INSTRUMENTS AND GENERAL PARAMETERS OF THE DETECTION METHODS USED

NMR spectra were recorded at ambient temperature with Varian MERCURY 300 spectrometer at 300 ($^1$H) and 75.5 MHz ($^{13}$C and APT). All spectra are referenced to tetramethylsilane as an internal standard (δ=0 ppm) using the signals of the residual protons of $CHCl_3$ (7.26 ppm) in $CDCl_3$, $CHD_2OD$ (3.31 ppm) in $CD_3OD$, HOD (4.79 ppm) in $D_2O$, or [$D_5$]DMSO (2.50 ppm) in [$D_6$]DMSO. Multiplicities of signals are described as follows: s=singlet, br. s=broad singlet, d=doublet, t=triplet, q=quartet, quint.=quintet, m=multiplet, br. m=broad multiplet. Coupling constants (J) are given in Hz. Multiplicities in the $^{13}$C NMR spectra were determined by APT (Attached Proton Test). EI-MS were recorded with MAT 95 (70 eV) and ESI-MS—with LCQ spectrometers (Fa. Finnigan), as well as with ESI-TOF spectrometer microTOF (Fa. Bruker) equipped with the "Apollo" ion source. HPLC-System (Knauer): Smartline pump 1000 (2×), UV-detector 2500, column thermostat 4000, mixing chamber, injection valve with 20 and 100 µL loop for the analytical and preparative columns, respectively; 6-port-3-channel switching valve; analytical column: Eurosphere-100 C18, 5 µm, 250×4 mm, flow 1.1 mL/min; preparative column: Eurosphere-100 C18, 5 µm, 250×8 mm, flow 3.8 mL/min; solvent A: MeCN+0.1% v/v TFA, solvent B: $H_2O$+0.1% v/v TFA; temperature 25° C. Analytical TLC was performed on MERCK ready-to-use plates with silica gel 60 ($F_{254}$) and developed by molybdatophosphoric acid solution (5% in EtOH), ninhydrin or anisaldehyde reagents. High performance silica gel precoated thin-layer plates (HPTLC Kieselgel 60, 10×10 cm) were purchased from MERCK (Darmstadt, Germany). Flash chromatography: MERCK silica gel, grade 60 (normal phase), 0.04-0.063 mm; Polygoprep 60-50, C18 from MACHERY-NAGEL (Düren, Germany; reversed-phase). Elemental analyses were carried out at Mikroanalytisches Laboratorium des Instituts für Organische und Biomolekulare Chemie der Georg-August-Universität Göttingen. THF was dried with Na-benzophenone. Organic solutions were dried over $MgSO_4$ or $Na_2SO_4$. All reactions were carried out with magnetic stirring under positive argon or nitrogen pressure using the standard technique with vacuum-inert gas manifold, unless stated otherwise. Abbrevations: HPLC, high pressure liquid chromatography; HPTLC, high performance thin layer chromatography; THF, tetrahydrofuran; DMF, dimethylformamide; HATU,O-(7-azabenzotriazol-1-yl)-N,N,N',N'-tetramethyluronium hexafluorophosphate; TSTU, N,N,N',N'-tetramethyl-O-(N-succinimidyl)uronium tetrafluoroborate.

EXAMPLE 1

Synthesis of nitro compounds 31-$NO_2$, 32-$NO_2$—H and 32-$NO_2$-Me

2-Fluoro-N,N-dimethyl-5-nitroaniline (31-$NO_2$):

N,N-Dimethylation of 2-fluoro-5-nitroaniline was performed according to a general method described by A. G. Giumanini et al., *Synthesis* 1980, 743-746. Specifically, 2-fluoro-5-nitroaniline (ALFA AESAR, 98%, 3.33 g, 21.3 mmol) and finely crushed $NaBH_4$ (4.73 g, 125 mmol) were suspended in THF (50 mL) and this slurry was added in small portions to a stirred solution of 3 M aq. $H_2SO_4$ (5.5 mL, 16.5 mmol) and 35% aq. formaldehyde (6.5 ml, 8.6 mmol) in THF (50 mL). After the first half of the mixture was added, the reaction mixture was acidified with 3 M aq. $H_2SO_4$ (5.50 mL, 16.5 mmol), and the addition was continued. Then 1 M aq. KOH was added to the reaction mixture until it became strongly basic. The organic phase was separated, and the aqueous phase was extracted with ether (2×50 mL). Combined organic solutions were washed with brine (2×100 mL), and dried with $Na_2SO_4$. After the solvents were evaporated in vacuo, the title compound was isolated by chromatography on $SiO_2$ with hexane/EtOAc mixture (4:1) as an eluent; yield—2.19 g (56%) of yellowish oil. $^1$H NMR ($CDCl_3$, 300 MHz, ppm): δ=2.92 (d, $^5J_{HF}$=1.2, 6 H, $CH_3$), 7.02-7.10 (m, 1H, H-3), 7.65-7.72 (m, 2H, H-4/6); $^{13}$C NMR ($CDCl_3$, 75.5 MHz, ppm): δ=42.3 (d, $^4J_{CF}$=4.9, $CH_3$), 112.9 (d, $^3J_{CF}$=6.2, C-4/6), 115.6 (d, $^3J_{CF}$=9.3, C-6/4), 116.4 (d, $^2J_{CF}$=24.2, C-3), 141.2 (d, $^2J_{CF}$=10.0, C-1), 144.7 (s, C-5), 157.8 (d, $J_{CF}$=256, C-2); EI-MS: m/z (rel. int., %)=184 (100) [M], 183 (46) [M−H], 138 (67) [M-$NO_2$], 137 (76) [M-$NO_2$—H], 123 (46) [M-$NO_2$—$CH_3$].

2-Fluoro-5-nitro-N-trifluoroacetylaniline (32-$NO_2$—H):

2-Fluoro-5-nitroaniline (7.0 g, 45 mmol) was dissolved in $CH_2Cl_2$ (200 mL) and $Et_3N$ (7.0 mL, 49 mmol) was added. Then ($CF_3CO$)$_2O$ (7.5 mL, 11.3 g, 54 mmol) in 25 mL of $CH_2Cl_2$ was added dropwise at 0° C., and the mixture was stirred for 24 h at room temperature. The reaction mixture was washed with water (3×300 mL) and saturated aq. $NaHCO_3$ (300 mL). The organic layer was separated, and an aqueous layer was extracted with $CH_2Cl_2$ (2×100 mL). Combined organic solutions were dried over $Na_2SO_4$, evaporated, and the title compound was isolated as a light beige solid with m.p. 112-113° C.; yield—10.5 g (93%). $^1$H NMR ($CDCl_3$, 300 MHz, ppm): δ=7.35 (t, $J_{HH}$=$^3J_{HF}$=9.2, 1H, H-3), 8.14 (ddd, $^4J_{HH}$=2.8, $^4J_{HF}$=4.2, 3$J_{HH}$=9.2, 1H, H-4), 8.22 (br s, NH), 9.18 (dd, $^3J_{HH}$=2.9, $^4J_{HF}$=6.4, 1H, H-6); $^{13}$C NMR ($CDCl_3$, 75.5 MHz, ppm): δ=115.1 (q, $^1J_{CF}$=289, $CF_3$), 116.1 (d, $^2J_{CF}$=22, C-3), 117.8 (d, $^3J_{CF}$=2.3, C-4/6), 122.3 (d, $^3J_{CF}$=9.5, C-6/4), 124.6 (d, $^2J_{CF}$=12.7, C-1), 144.5 (C-5), 154.4 (q, $^2J_{CF}$=42, CO), 155.8 (d, $^1J_{CF}$=256, C-2); EI-MS: m/z (rel. int., %)=223 (100) [M—HCO]$^+$, 154 (21), 126 (18), 99 (17).

2-Fluoro-N-methyl-N-trifluoroacetyl-5-nitroaniline (32-$NO_2$-Me):

To a solution of compound 32-$NO_2$—H (13.9 g, 55.2 mmol) and MeI (14.8 g, 0.104 mol) in DMF (80 mL), $K_2CO_3$ (12.5 g, 90.6 mmol) was added. After vigorous stirring for 24 h at 90° C., volatile materials were evaporated in vacuum. The residue was diluted with water (200 mL), the organic layer was separated, and the aqueous layer was extracted with ether (3×100 mL). Combined organic solutions were dried, and the solvent was evaporated at an ambient pressure (bath temperature 50° C.). The title compound was isolated by chromatography on $SiO_2$ (600 g) with hexane/EtOAc mixture (1:0→1:1) as an eluent; yellowish oil (13.6 g, purity ca. 90%, yield 83%). $^1H$ NMR ($CDCl_3$, 300 MHz, ppm): δ=3.36 (s, 3 H, $CH_3$), 7.39 (t, $^3J_{HH}=J_{HF}=8.8$, 1H, H-3), 8.25 (dd, $^4J_{HH}=2.6$, $^4J_{HF}=6.5$, 1H, H-6), 8.32-8.38 (m, 1H, H-4); EI-MS: m/z (rel. int., %)=266 (100) [M], 197 (57) [M-$CF_3$], 184 (32), 170 (23), 123 (37), 110 (18).

EXAMPLE 2

Reduction of Nitro Compounds 31-$NO_2$, 32-$NO_2$—H and 32-$NO_2$-Me into Anilines 31-$NH_2$, 32-$NH_2$—H and 32-$NH_2$-Me (General Method (1))

5-Amino-2-fluoro-N-(trifluoroacetyl)aniline (32-$NH_2$—H):

A Schlenk-flask (250 mL) was evacuated and flushed with argon two times. Then 10% Pd/C (0.74 g, VWR International, oxidized form) and EtOAc (30 mL) were placed into it, and the flask was closed with a septum. The mixture was flushed with hydrogen and stirred vigorously to activate the catalyst. Then $^3$2-$NO_2$—H (5.14 g, 20.4 mmol) in 20 mL of EtOAc was added by syringe through a septum. (Addition was accompanied by the exothermic reaction). The solution was hydrogenated for 4 h at 20° C. Then hydrogen was replaced by argon and the mixture was filtered through Celite®. The filter-cake was washed with EtOAc (2×50 mL) and the solvent was evaporated in vacuo to yield the title compound as a brownish solid with m.p. 116-118° C.; yield—4.35 g (96%). $^1H$ NMR ($CDCl_3$, 300 MHz, ppm): δ=3.30 (br. s, 3H, $NH_2$), 6.44 (ddd, $3J_{HH}=8.8$, $4J_{HF}=4.1$, $^3J_{HH}=2.8$, 1H, H-4), 6.92 (dd, $3J_{HH}=8.9$, $3J_{HF}=10.4$, 1H, H-3), 7.63 (dd, $^4J_{HH}=2.8$, $^4J_{HF}=6.4$, 1H, H-6), 8.01 (s, 1H, NH); $^{13}C$ NMR (75 MHz, $CDCl_3$): δ=107.8 (s, C-4/6), 112.2 (d, $^3J_{CF}=7.1$, C-6/4), 115.4 (q, $^1J_{CF}=289$, $CF_3$), 115.5 (d, $^2J_{CF}=28$, C-3), 124.0 (d, $^2J_{CF}=11.2$, C-1), 143.3 (s, C-5), 144.6 (d, $^1J_{CF}=236$, C-2), 154.5 (q, $^2J_{CF}=37.5$, CO); ESI-MS, negative mode: m/z (rel. int., %)=221 (100) [M–H]$^-$; elemental analysis (%): C, 43.16; H, 2.85; N, 12.86 (found); C, 43.25; H, 2.72; N, 12.61 (calc.)

5-Amino-2-fluoro-N-methyl-N-trifluoroacetylaniline (32-$NH_2$—H) was obtained as oil from compound 32-$NO_2$—$NH_2$—H (13.4 g, 50.4 mmol) according to general method 1, yield—10.65 g (96%). $^1H$ NMR ($CDCl_3$, 300 MHz, ppm): δ=3.27 (s, 3H, $CH_3$), 3.65 (br. s, 2H, $NH_2$), 6.53 (dd, $^4J_{HH}=2.8$, $^4J_{HF}=6.2$, 1H, H-6), 6.60-6.68 (m, 1H, H-4), 6.93 (t, $^3J_{HH}=^3J_{HF}=9.1$, 1H, H3); $^{13}C$ NMR ($CDCl_3$, 75.5 MHz, ppm) δ=38.4 (s, $CH_3$), 115.2 (s, C-4/6), 116.2 (q, $^1J_{CF}=289$, $CF_3$), 116.8 (d, $^3J_{CF}=6.9$, C-6/4), 116.9 (d, $^2J_{CF}=21$, C-3), 128.3 (d, $^2J_{CF}=14.5$, C-1), 143.2 (s, C-5), 151.2 (d, $^1J_{CF}=242$, C-2), 157.2 (q, $^2J_{CF}=36$, CO); EI-MS: m/z (rel. int., %)=236 (100) [M], 152 (46) [M-$CF_3$—$CH_3$], 139 (25) [M-$COCF_3$], 110 (85) [M-$NCH_3$—$COCF_3$]; elemental analysis (%): C, 46.03; H, 3.65; N, 12.04 (found); C, 45.77; H, 3.41; N, 11.86 (calc.).

5-Amino-2-fluoro-N,N-dimethylaniline (32-$NH_2$) was obtained from compound 32-$NO_2$ (1.60 g, 87 mmol) according to general method (1); yield—1.23 g (92%) of a brownish oil. $^1H$ NMR ($CDCl_3$, 300 MHz, ppm): δ=2.78 (s, 6H, $CH_3$), 3.43 (br. s, 2H, $NH_2$), 6.13 (dt, $^4J_{HH}=3.1$, $3J_{HF}=4$ $J_{HF}=8.5$, 1H, H-4), 6.20 (dd, $^4J_{HH}=2.7$, $^4J_{HF}=7.6$, 1H, H-6), 6.77 (dd, $^3J_{HH}=8.5$, $^3J_{HF}=12.8$, 1H, H-3); $^{13}C$ NMR ($CDCl_3$, 75.5 MHz, ppm): δ=42.7 (d, $^4J_{CF}=4.1$, $CH_3$), 105.4 (d, $^3J_{CF}=2.8$, C-4/6), 106.9 (d, $^3J_{CF}=7.6$, C-4/6), 116.3 (d, $^2J_{CF}=22.3$, C-3), 141.1 (d, $^2J_{CF}=9.6$, C-1), 142.7 (d, $^4J_{CF}=2.1$, C-5) 148.9 (d, $^1J_{CF}=235$, C-2); EI-MS: m/z (rel. int., %)=154 (100) [M], 153 (67) [M–H], 138 (20) [M-$NH_2$].

EXAMPLE 3

Diazotation of Anilines 32-$NH_2$—H, 32-$NH_2$-Me, 31-$NH_2$ and Conversion into Phenols 32-OH—H, 32-OH-Me and 31-OH (General Method (2))

2-Fluoro-5-hydroxy-N-trifluoroacetylaniline (2-OH—H): Compound 32-$NH_2$—H (248 mg, 1.12 mmol) was dissolved in 35% aq. $H_2SO_4$ (2 mL) cooled to 0° C., and $NaNO_2$ (96.6 mg 1.4 mmol) in water (1 mL) was added carefully through a Teflon® tube to the bottom of the flask. An exothermic reaction was observed and the brown gas evolved. The mixture was stirred for 5 min, several crystals of urea were added to the reaction mixture, and then the reaction solution was transferred into the blue solution of $Cu(NO_3)_2$*$3H_2O$ (3.75 g, 15.5 mmol) in water (36 mL). The color of the solution changed to green. With vigorous stirring, the powder of $Cu_2O$ (132 mg, 0.920 mmol) was added, and the evolution of nitrogen was complete in several minutes. The reaction mixture was extracted with ether (3×200 mL); combined organic solutions were washed with brine (100 mL) and dried. The solvent was removed in vacuo, and the residue was filtered through $SiO_2$ (50 mL), eluting with $CH_2Cl_2$/EtOAc mixture (4:1). The title compound was isolated as a brown solid (116 mg, 52%) with m.p. 151-153° C. (ether/hexane). This procedure may be easily scaled-up. $^1H$ NMR ($CD_3OD$, 300 MHz, ppm): δ=6.70 (ddd, $^4J_{HH}=3.0$, $^4J_{HF}=3.9$, $^3J_{HH}=9.0$, 1H, H-4), 7.03 (dd, $^3J_{HH}=9.0$, $^3J_{HF}=10.1$, 1H, H-3), 7.08 (dd, $^4J_{HH}=3.0$, $^4J_{HF}=6.2$, 1H, H-6); $^{13}C$ NMR ($CD_3$ OD, δ5.5 MHz, ppm): δ=113.4 (s, C-4/6), 115.4 (d, $3J_{CF}=7.2$, C-6/4), 117.2 (d, $^2J_{CF}=21.3$, C-3), 117.4 (q, $^1J_{CF}=298$, $CF_3$), 124.4 (d, $^2J_{CF}=13.8$, C-1), 150.5 (d, $^1J_{CF}=239$, C-2), 154.8 (s, C-5), 157.1 (q, $^2J_{CF}=37.7$, CO); EI-MS: m/z (rel. int., %)=223 (100) [M], 154 (21), 126(22), 99 (22); elemental analysis (%): C, 42.92; H, 2.44; N, 6.54 (found); C, 43.07; H, 2.26; N, 6.28 (calc.).

2-Fluoro-5-hydroxy-N-Methyl-N-trifluoroacetylaniline (2-OH-Me) was prepared from compound $^3$2-$NH_2$-Me (10.5 g, 44.5 mmol), $NaNO_2$ (3.84 g, 55.6 mmol), $Cu(NO_3)_2$*$3H_2O$ (167 g, 0.69 mol) and $Cu_2O$ (5.90 g, 41.0 mmol) according to general method 2. The title compound was separated from the impurities with higher $R_f$ by chromatography on $SiO_2$, eluent —$CH_2Cl_2$/MeOH (50:1). Recrystallization from $CHCl_3$/hexane mixture afforded 5.7 g (54%) of a brown solid with m.p. 130-132° C. $^1H$ NMR ($CDCl_3$/[$D_6$]DMSO, 300 MHz, ppm): δ=3.22 (s, 3H, $CH_3$), 6.71 (dd, $^4J_{HH}=2.8$, $^4J_{HF}=6.2$, 1H, H-6), 6.74-6.82 (m, 1H, H-4), 6.96 (t, $^3J_{HF}=9.2$, 1H, H-3), 9.38 (s, 1H, OH); $^{13}C$ NMR ($CDCl_3$/[$D_6$]DMSO, 75.5 MHz, ppm): δ=38.1 (s, $CH_3$), 114.5 (s, C-6), 114.8 (q, $^1J_{CF}=288$, $CF_3$), 115.1 (d, $^2J_{CF}=21$, C-3). 116.1 (d, $3J_{CF}=7.1$, C-4), 126.3 (d, $^2J_{CF}=14.9$, C-1), 149.8 (d, $^1J_{CF}=240$, C-2), 152.6 (s, C-5), 155.1 (q, $^2J_{CF}=35.7$, CO); EI-MS: m/z (rel. int., %)=237 (100) [M], 168 (10) [M-$CF_3$], 153 (10) [M-$CF_3$—$CH_3$], 139 (18) [M-$COCF_3$], 111 (52) [M-$NCH_3$—$COCF_3$]; elemental analysis (%): C, 45.24; H, 3.03; N, 6.13 (found); C, 45.58; H, 2.98; N, 5.91 (calc.).

2-Fluoro-5-hydroxy-N,N-dimethylaniline (32-OH) was prepared from compound 32-$NH_2$ (1.23 g, 7.99 mmol), $NaNO_2$ (0.69 g, 10.0 mmol), $Cu(NO_3)_2$*$3H_2O$ (30.0 g, 0.12 mol) and $Cu_2O$ (1.05 g, 7.34 mmol) according to general method 2. The title compound was isolated by chromatography on $SiO_2$ with hexane/EtOAc mixture (4:1) as an eluent; yield—0.581 g (47%) of a light brown solid with m.p. 129-130° C. $^1H$ NMR ($CD_3$ OD, 300 MHz, ppm): δ=2.74 (d, $^5J_{HF}$=0.7, 6H, CH$_3$), 6.24-6.31 (m, 1H, H-4), 6.40 (dd, $^4J_{HH}$=2.9, $^4J_{HF}$=7.5, 1H, H-6), 6.80 (dd, $^3J_{HH}$=8.7, $^3J_{HF}$=12.8, 1H, H-3); $^{13}$C NMR (CD$_3$OD, 76 MHz, ppm): δ=43.2 (d, $^4J_{CF}$=4.2, CH$_3$), 106.7 (d, $^3J_{CF}$=2.9, C-4/6), 108.3 (d, $^3J_{CF}$=7.6, C-6/4), 117.0 (d, $^2J_{CF}$=22.6, C-3), 142.3 (d, $^2J_{CF}$=10.3, C-1), 149.0 (s, C-5), 153.5 (d, $^1J_{CF}$=213, C-2); EI-MS: m/z (rel. int., %)=155 (75) [M], 154 (100) [M−H], 139 (20) [M-CH$_3$—H].

EXAMPLE 4

Preparation of Anilines 33-H, 33-Me and 40 by Reduction of Amides 32-OH—H, 32-OH-Me and 39 with BH$_3$*THF Complex (General Method (3))

2-Fluoro-5-hydroxy-N-(2,2,2-trifluoroethyl)aniline (33-H):

To a solution of amide 32-OH—H (17.8 g, 79.8 mmol) in dry THF (50 mL), 1 M solution of BH$_3$*THF complex in THF (160 mL) was added at 0° C., and the mixture was heated with reflux overnight. Excess of BH$_3$ was carefully destroyed at 0° C. by adding MeOH (20 mL) followed by 1 M aq. NaOH (100 mL). After stirring at room temperature for 20 min, the mixture was diluted with ether (300 mL), and the organic layer was separated. The aqueous layer was extracted with ether (3×100 mL); combined organic solutions were washed with sat. aq. NaHCO$_3$ (100 mL), brine (100 mL), dried and the solvent was evaporated in vacuo. To remove an impurity with lower R$_f$, the title compound was purified by chromatography on SiO$_2$ (200 g) with hexane/EtOAc mixture (2:1). An analytical sample was sublimed in vacuo (5-10 mbar). Yield—1.83 g (78%) of white solid with m.p. 106-107° C. $^1$H NMR (CD$_3$OD, 300 MHz, ppm): δ=3.80 (q, $^3J_{HF}$=9, 2 H, CH$_2$CF$_3$), 6.05 (ddd, $^4J_{HH}$=2.9, $^4J_{HF}$=3.3, $^3J_{HH}$=8.6, 1H, H-4), 6.27 (dd, $^4J_{HH}$=2.7, $^4J_{HF}$=7.5, 1 H, H-6), 6.76 (dd, $^3J_{HH}$=8.7, 3J$_{HF}$=11.5, 1H, H-3); $^{13}$C NMR (CDCl$_3$/[D6]DMSO, 75.5 MHz, ppm): δ=44.3 (q, $^2J_{CF}$=33.5, CH$_2$CF$_3$), 99.0 (s, C-4/6), 102.7 (d, $^3J_{CF}$=6.8, C-6/4), 113.9 (d, $^2J_{CF}$=19.8, C-3), 124.3 (q, $^1J_{CF}$=280, CF$_3$), 134.7 (d, $^2J_{CF}$=12.6, C-1), 144.5 (d, $^1J_{CF}$=229, C-2), 153.2 (d, $^4J_{CF}$=1.7, C-1). EI-MS: m/z (rel. int., %)=210 (5) [M+H], 209 (90) [M], 140 (100) [M-CF$_3$]; elemental analysis (%): C, 46.09; H, 3.64; N, 6.62 (found), C, 45.94; H, 3.37; N, 6.70 (calc.).

2-Fluoro-5-hydroxy-N-methyl-N-(2,2,2-trifluoroethyl) aniline (33-Me) was prepared from compound 32-OH-Me (2.52 g, 10.6 mmol) and 1 M solution of BH$_3$*THF in THF (32 mL) according to general method 3. The title product was purified from the impurities with lower R$_f$ by chromatography on SiO$_2$ (200 g) with hexane/EtOAc (5:1) mixture as an eluent; yield—2.28 g (96%) of a brown oil. $^1$H NMR (CDCl$_3$, 300 MHz, ppm): δ=2.96 (s, 3H, CH$_3$), 3.82 (q, $^3J_{HF}$=9.1, 2 H, CH$_2$CF$_3$), 5.04 (br. s, 1H, OH), 6.30 (ddd, $^4J_{HF}$=$^4J_{HH}$=3.1, $^3J_{HH}$=8.7, 1H, H-4), 6.44 (dd, $^4J_{HH}$=3.0, $^4J_{HF}$=7.4, 1H, H-6), 6.84 (dd, $^3J_{HH}$=8.7, $^3J_{HF}$=12.9, 1H, H-3); $^{13}$C NMR (CDCl$_3$, 75.5 MHz, ppm): δ=40.6 (s, CH$_3$), 55.1 (qd, J=9.6 and 31.4, C, CH$_2$CF$_3$), 106.8 (d, $^3J_{CF}$=3.0, C-6), 107.5 (d, $^4J_{CF}$=7.9, C-4), 116.6 (d, $^2J_{CF}$=23.3, C-3), 125.6 (q, J$_{CF}$=284.5, CF$_3$), 138.3 (d, $^2J_{CF}$=9.7, C-1), 149.1 (d, $^1J_{CF}$=236, C-2), 151.9 (s, C-5); EI-MS: m/z (rel. int., %)=223 (12) [M], 154 (100) [M-CF$_3$], 139 (10) [M-CF$_3$—CH$_3$].

N-(2,2,2-Trifluoroethyl)-m-methoxyaniline (39):

$^1$H NMR (250 MHz, CDCl$_3$): δ=3.76/3.77 (2×t, $^3J_{H,F}$=7 Hz), 3.78 (s, E 5H), 3.97 (br. t, $^4J_{H,F}$=6.0 Hz, 1H, NH), 6.24 (t, $^4J_{H,H}$=2.3 Hz, 1H), 6.30 (dd, $^3J_{H,H}$=8 Hz, $^4J_{H,H}$=2 Hz, 1H), 6.37 (dd, $^3J_{H,H}$=7.8 Hz, $^4J_{H,H}$=2.4 Hz, 1H), 7.12 ppm (t, $^3J_{H,H}$=7.8 Hz, 1H). $^{13}$C NMR (62.9 MHz, CDCl$_3$): δ 45.9 (q, 2J$_{C,F}$=33 Hz), 55.1, 99.4 (CH), 104.0 (CH), 106.0 (CH), 125.0 (q, $^2J_{C,F}$=280 Hz), 130.2 (CH), 147.6 (C), 160.8 (C) ppm. MS (EI): m/z (%)=205 (80) [M], 136 (100) [M-CF$_3$]$_j$

EXAMPLE 5

Synthesis of Anilines 36-H and 36-Me by Alkaline Hydrolysis of the Trifluoroacetamides 32-OH—H and 32-OH-Me (General Method (4))

2-Fluoro-5-hydroxyaniline (36-H) was obtained by heating the solution of trifluoroacetamide 32-OH—H (3.50 g, 15.7 mmol) in MeOH (25 mL) with 30% aq. NaOH (5.5 mL, 30 mmol) at 90° C. The mixture was refluxed overnight and, after cooling down to room temperature, neutralized with 3 M aq. HCl. The title compound was extracted with ether (2×100 mL); the solvent was evaporated in vacuo, and the residue was purified on SiO$_2$ (100 g) with CH$_2$Cl$_2$/methanol mixture (50:1) as an eluent. Yield—1.85 g (93%), m.p. 141-143° C. (lit.: 142-144° C.; WO97/39064). $^1$H NMR ([D$_6$]DMSO/CDCl$_3$, 300 MHz, ppm): δ=4.42 (br. s, 2H, NH), 5.97 (ddd, $^4J_{HH}$=3.0, $^4J_{HF}$=3.5, $^3J_{HH}$=8.7, 1H, H-4), 6.21 (dd, $^3J_{HH}$=2.9, $^4J_{HF}$=7.7, 1H-6), 6.64 (dd, $^3J_{HH}$=8.7, 3J$_{HF}$=11.0, 1H, H-3), 8.36 (br. s, 1H, OH); $^{13}$C NMR ([D$_6$]DMSO/CDCl$_3$, 75.5 MHz, ppm): S=103.3 (d, $^4J_{HF}$=3.3, C-4/6), 103.5 (d, $^3J_{HF}$=6.6, C-4/6), 114.5 (d, $^2J_{CF}$=19.8, C-3), 135.0 (d, $^2J_{CF}$=14.3, C-1), 145.1 (d, $^1J_{CF}$=228.2, C-2), 153.4 (d, $^4J_{CF}$=1.7, C-5); EI-MS: m/z (rel. int., %)=127 (100) [M]; elemental analysis (%): C, 55.44; H, 4.67; N, 10.54 (found); C, 56.69; H, 4.76; N, 11.02 (calc.).

2-Fluoro-5-hydroxy-N-methylaniline (36-Me) was prepared from compound 32-OH-Me (2.70 g, 11.4 mmol) dissolved in CH$_3$OH (11 mL) by saponification with 30% NaOH (4 mL) at 90° C. Work-up and isolation were performed according to the general method (4). A brown solid (1.78 g) was isolated and recrystallized from hexane to give 1.27 g (79%) of the title compound as a beige solid with m.p. 68-69° C. $^1$H NMR (CDCl$_3$, 300 MHz, ppm): S=2.78 (s, 3H, CH$_3$), 4.62 (br. s, 2H, NH, OH), 6.02 (ddd, $^4J_{HH}$=$^4J_{HF}$=3.2, 3J$_{HH}$=8.6, 1H, H-4), 6.16 (dd, J=2.9, 7.2, 1H, H-6), 6.78 (dd, $^3J_{HH}$=8.6, $^3J_{HF}$=11.3, 1H, H-3); $^{13}$C NMR (CDCl$_3$, 75.5 MHz, ppm): S=30.2 (s, CH$_3$), 99.33 (d, $^3J_{CF}$=3.1, C-6), 101.93 (d, $^3J_{CF}$=7.1, C-4), 114.32 (d, $^2J_{CF}$=20.0, C-3), 138.44 (d, $^2J_{CF}$=13.37, C-1), 146.42 (d, $^1J_{CF}$=231, C-2), 151.32 (s, C-5); EI-MS: m/z (rel. int., %)=141 (100) [M], 140 (97) [M−H].

Demethylation of amine 40: N-(2,2,2-trifluoroethyl)-m-hydroxyaniline (41):

Starting amine 40 (17.5 g, 86 mmol) was dissolved in glacial AcOH (50 mL), 48% aq. HBr (60 mL) was added, and the mixture was refluxed for 7 h under argon (TLC of the neutralized probe indicated the full conversion of the starting amine). The reaction mixture was cooled with ice, CHCl$_3$ (100 mL) was added, and the mixture was carefully neutralized to pH~5-6 with 30% aq. NaOH (keeping the internal temperature in the range of 5-10° C.). Organic phase was separated, and an aqueous phase was extracted with CHCl$_3$ (3×150 mL). Combined organic solutions were washed carefully with sat. aq. solution of NaHCO$_3$ (3×150 mL), dried and evaporated. The residue was dissolved in small amount of CHCl$_3$ and filtered through SiO$_2$ (150 g), in order to remove impurities with very high and very low R$_f$ (eluent—CHCl$_3$/MeOH [50:1] or hexane/EtOAc [2:1]); yield—10.7 g (65%) of red oil, which at 0° C. very slowly crystallized into an orange solid with m.p. 38° C.; $^1$H NMR (300 MHz, CDCl$_3$): δ=3.67 (t, $^3J_{H,F}$=9 Hz), ~5 (br. s, 1H, NH), 6.24 (t, $^4J_{H,H}$=2.3 Hz, 1H), 6.27 (m, 2H), 7.05 ppm (t, $^3J_{H,H}$=8.1 Hz, 1H); $^{19}$F NMR (282.4 MHz, acetone-d$_6$): δ=−72.3 (t, $^3J_{H,H}$=8.3 Hz)

ppm; $^{13}$C NMR (75.6 MHz, CDCl$_3$): δ=45.3 (q, $^3J_{C,F}$=26 Hz), 100.3 (CH), 106.0 (C), 106.1 (CH), 124.9 (q, $^2J_{C,F}$=280 Hz), 130.5 (CH), 147.9 (C), 156.5 (C) ppm; EI-MS: m/z=191 (76) [M$^+$], 122 (100) [M-CF$_3$]$^+$; HRMS (C$_8$H$_8$NOF$_3$): 192.06306 (found M+H), 192.06307 (calc.).

EXAMPLE 6

Condensation of 2-Fluoro-5-Hydroxyanilines 34-H, 34-Me, 36-H, 36-Me, 31-OH with Phthalic- and Trimellitic Anhydrides: Preparation of 2,7-Difluorinated Rhodamines 33-H—H, 33-H—COOH/35-H—COOH, 33-Me-H, 33-Me-COOH/35-Me-COOH, 37-H—H—H—H, 73-H—H—COOH/38-H—H—COOH, 37-Me-H—H, 37-Me-H—COOH/38-Me-H—COOH, 37-Me-Me-H, 37-Me-Me-COOH/38-Me-Me-COOH (General Method (5))

2,7-Difluoro-N,N'-bis(2,2,2-trifluoroethyl)rhodamine (33-H—H):

A mixture of powdered phthalic anhydride (259 mg, 1.75 mmol) and aniline 34-H (725 mg, 3.47 mmol) was heated with stirring under argon up to 125-160° C., until it melted. Then ZnCl$_2$ (0.5-1 g) was added, and the mixture was heated at 180-200° C. for 3-4 h. After cooling to room temperature, water (10 mL) was added, and the solution was seeded with powdered title compound. After stirring at room temperature overnight, the precipitated bright orange solid (653 mg, 71%) was collected by filtration, washed with water and dried. $^1$H NMR ([D$_6$]DMSO, 300 MHz, ppm): δ=3.10-3.88 (br. m, 4H, CH$_2$CF$_3$, H$_2$O), 6.46 (d, $^3J_{HF}$=11, 2H, H-1/8), 6.93-7.04 (m, 2H, H-4/5), 7.32 (d, $^3J_{HH}$=9, 1H, H-7'), 7.70-7.84 (m, H-5'/6'), 8.03 (d, $^3J_{HH}$=7, 1H, H-4); $^{13}$C NMR ([D$_6$]DMSO, 125 MHz, ppm): δ=43.5 (q, $^2J_{CF}$=33.2, CH$_2$CF$_3$), 98.8 (s, C-4/5), 111.0 (d, $^2J_{CF}$=21.1, C-1/8), 125.2 (q, $^1J_{CF}$=281, CF$_3$), 128.2, 130.2, 130.5, 132.8, 147.6 (d, $^1J_{CF}$=237.5, C-2/7), 167.7 (s, C-2'), 168.5 (s, CO); $^{19}$F NMR ([D$_6$]DMSO, 282 MHz, ppm) δ=−139.9÷−139.6 (m, 2 F, F-3/F-6), −70.2 (s, 6 F, CF$_3$); ESI-MS, positive mode: m/z (rel. int., %)=553 (100) [M+Na]$^+$, 1083 (72) [2M+Na]$^+$; ESI-MS, negative mode: m/z (rel. int., %)=529 (100) [M−H]$^−$, 1059 (96) [2M−H]$^−$.

5' (6')-carboxy-2,7-difluoro-N,N'-bis(2,2,2-trifluoroethyl)-rhodamine (33-H—COOH/35-H—COOH):

According to the general method (5), heating of aniline 34-H (558 mg, 2.67 mmol) and trimellitic anhydride (324 mg, 1.69 mmol) in the presents of anhydrous ZnCl$_2$ afforded the title compound (600 mg, 78%) as a mixture of 5'- and 6'-isomers. 5' isomer: $^1$H NMR ([D$_6$]DMSO, 300 MHz, ppm): δ=3.96-4.19 (m, 4H, CH$_2$CF$_3$), 6.49 (d, $^3J_{HH}$=12, 2H, H-1/8), 6.19-6.61 (m, 4 H, NH), 6.88 (d, $^4J_{HF}$=7, 2 H, H-4/5), 7.42 (d, $^3J_{HH}$=7, 2H, H-7'), 8.28 (d, $^3J_{HH}$=8, 1H, H-6'), 8.37 (s, 1H, H-4'); 6' isomer: $^1$H NMR ([D$_6$]DMSO, 300 MHz, ppm): δ=3.96-4.19 (m, 4H, CH$_2$CF$_3$), 6.47 (d, $^3J_{HF}$=12, 2H, H-1/8), 6.19-6.61 (m, 2H, NH), 6.88 (d, $^4J_{HF}$=7, 2 H, H-4/5), 7.58 (s, 1H, H-7'), 8.08 (d, $^3J_{HH}$=8, 1H, H-4'/5'), 8.23 (d, $^3J_{HH}$=8, 1H, H-5'/4'). Mixture of isomers: ESI-MS, negative mode: m/z (rel. int., %)=573 (100) [M−H]$^−$, 1147 (46) [2M−H]$^−$; ESI-MS, positive mode: m/z (rel. int., %)=575 (100) [M]$^+$.

2,7-Difluoro-N,N-dimethyl-N,N-bis(2,2,2-trifluoromethyl)-rhodamine (33-Me-H): was prepared from compound 34-Me (725 mg, 3.25 mmol) and phthalic anhydride (259 mg, 1.75 mmol) according to the general method (5). The title product was purified by chromatography on SiO$_2$ (100 g) with CH$_2$Cl$_2$ as an eluent and sublimed to yield 290 g (32%) of a pale pink solid (closed form). $^1$H NMR (CDCl$_3$, 300 MHz, ppm): δ=3.06 (s, 6H, CH$_3$), 3.91 (qd, $^5J_{HF}$=8.4, $^3J_{HF}$=15.8, 4 H, CH$_2$CF$_3$), 6.36 (d, $^3J_{HF}$=13.8, 2 H, H-1/8), 6.75 (d, $^4J_{HF}$=7.7, 2H, H-4/5), 7.17 (d, $^3J_{HH}$=6, 1H, H-7'), 7.66 (m, 2H, H-5'/6'), 8.02 (d, $^3J_{HH}$=6, 1H, H-4'); $^{13}$C NMR (CDCl$_3$, 75.5 MHz, ppm): δ=40.9 (s, CH$_3$), 54.7 (dq, $^4J_{CF}$=10.7, $^2J_{CF}$=32.0, CH$_2$CF$_3$), 82.5 (s, C-9), 106.4 (d, $^3J_{CF}$=3.2, C-4/5), 110.1 (d, J=7.2, C-8a/8b), 114.5 (d, J=24.8, C-1/8), 123.9 (s, PhCOOH), 125.29 (s, PhCOOH), 125.4 (q, $^1J_{CF}$=284, CF$_3$), 126.7 (s, C-3') 130.1 (s, PhCOOH), 135.2 (s, PhCOOH), 139.9 (d, $^2J_{CF}$=9.8, C-3/6), 148.2 (s, C-4-a/4b), 150.1 (d, J=242, C-2/7), 152.2 (s, C-2'), 168.8 (s, CO); $^{19}$F NMR (CDCl$_3$, 282 MHz, ppm): δ=−67.21÷−70.90 (m, 2 F), −126.60÷−128.12 (m, 6F, CH$_2$CF$_3$); ESI-MS, positive mode: m/z (rel. int., %)=559 (12) [M+H]$^+$, 581 (100) [M+Na]$^+$, 1139 (54) [2M+Na]$^+$.

5' (6')-Carboxy-2,7-difluoro-N,N'-dimethyl-N,N-bis(2,2,2-trifluoroethyl)rhodamine (33-Me-COOH/35-Me-COOH) was obtained as a mixture of 5'- and 6'-isomers from aniline 34-Me (0.20 g, 0.90 mmol) and trimellitic anhydride (0.11 g, 0.58 mmol) according to the general method 5. The product was isolated as a bright orange solid by chromatography on SiO$_2$ (100 g) with CH$_2$Cl$_2$/methanol mixture (20:1-5:1) as an eluent; yield—67 mg, (25%). 5' isomer: $^1$H NMR ([D$_6$] DMSO, 300 MHz, ppm): δ=2.98 (s, 6H, CH$_3$), 4.10-4.25 (m, 5H, CH$_2$CF$_3$, COOH), 6.59 (d, $^3J_{HF}$=13.7, 2 H, H-1/8), 6.96 (d, $^4J_{HF}$=7.8, 2 H, H-4/5), 7.32 (d, $^3J_{HH}$=8, 1 H, H-7'), 8.30 (d, J=8.0, 1H, H-6'), 8.41 (s, 1H, H-4'). 6' isomer: $^1$H NMR (CDCl$_3$/CD$_3$OD, 300 MHz, ppm): δ=3.07 (s, 6H, CH$_3$), 3.77-3.90 (m, 4H, CH$_2$CF$_3$), 6.24 (d, $^3J_{HF}$=14.1, 2 H, H-1/8), 6.68 (d, $^4J_{HF}$=7.7, 2 H, H-4/5), 7.73 (s, 1H, H-7'), 7.97 (d, $^3J_{HH}$=7.4, 1H, H-5'), 8.21 (d, J=7, 1H, H-4'); $^{13}$C NMR (CDCl$_3$, 75.5 MHz, ppm): δ=40.6 (s, CH$_3$), 54.4 (dq, $^4J_{CF}$=10.9, $^3J_{CF}$=32.1, CH$_2$CF$_3$), 83.2 (s, C-9), 106.1 (s, C-4/5), 108.9 (s, C-8a/8b), 114.0 (d, $^2J_{CF}$=24.9, C-1/8), 124.9 (s, PhCOOH), 125.2 (s, C-3'), 125.2 (q, $^1J_{CF}$=284, CF$_3$), 129.1 (s, PhCOOH), 131.5 (s, PhCOOH), 140.0 (d, $^2J_{CF}$=9.6, C-3/6), 147.9 (s, C-4a/4b), 149.9 (d, J$_{CF}$=242, C-2/7), 152.0 (s, C-2'), 168.5 (s, CO); $^{19}$F NMR (CDCl$_3$, 282 MHz, ppm): δ=−69.17÷−70.18 (m, 2F), −126.93÷−127.90 (m, 6F, CH$_2$CF$_3$). Mixture of isomers: ESI-MS, positive mode: m/z (rel. int., %)=603 (100) [M+H]$^+$; ESI-MS, negative mode: m/z (rel. int., %)=601 (100) [M−H]$^−$, 1203 (30) [2M−H]$^−$.

2,7-Difluororhodamine (37-H—H—H) was prepared from aniline 36-H (191 mg, 1.50 mmol) and phthalic anhydride (148 mg, 1.00 mmol) according to the general method 5 and isolated by chromatography on SiO$_2$ with CH$_2$Cl$_2$/methanol mixture (10:1) as an eluent; Yield—60 mg (22%) of bright red solid. HPLC-area: 93%, t$_R$=10.1 min (A/B:30/70-50/50 in 25 min, 254 nm). $^1$H NMR ([D$_6$]DMSO, 300 MHz, ppm): δ=5.65 (s, 4H, NH$_2$), 6.18 (d, 3J$_{HF}$=11.6, 2 H, H1/8), 6.59 (d, $^4J_{HF}$=7.8, 2 H, H-4/5), 7.23 (d, $^3J_{HH}$=7.0, 1H, H-7'), 7.64-7.79 (m, 2H, H-5'/6'), 7.93 (d, $^3J_{HH}$=7.4, 1 H, H-4'); $^{13}$C NMR ([D$_6$]DMSO, 75.5 MHz, ppm): δ=101.5 (d, $^3J_{CF}$=4.4, CH, C-4/5), 104.4 (d, $^3J_{CF}$=6.1, C-8a/8b), 112.2 (d, $^2J_{CF}$=20.7, C-1/8), 123.8 (s, PhCOOH), 124.7 (s, PhCOOH), 126.4 (s, C-3'), 130.0 (s, PhCOOH), 135.4 (s, PhCOOH), 139.4 (d, $^2J_{CF}$=15.0, C-3/6), 146.9 (d, $^1J_{CF}$=234, C-2/7), 148.1 (s, C-4a/4b), 151.5 (s, C-2'), 168.3 (s, CO); $^{19}$F NMR (DMSO, 282 MHz, ppm): δ=−139.1 (s, 2 F); ESI-MS, positive mode: m/z (rel. int., %)=367 (100) [M+H]$^+$.

5'(6')-Carboxy-2,7-difluororhodamine (37-H—H—COOH/38-H—H—COOH) was obtained as a mixture of two diastereomers from aniline 36-Me (0.19 g, 1.5 mmol) and trimellitic anhydride (0.19 g, 1.00 mmol) according to the general method 5. The title compounds were isolated as bright red solid by chromatography on SiO$_2$ with CH$_2$Cl$_2$/methanol mixture (13:3→4:1) as an eluent; yield—43 mg (14%). The diastereomers were separated by chromatography on RP-18 (VWR) with water/methanol (5:1) mixture as an eluent. 5'-isomer: $^1$H NMR ([D$_6$]DMSO, 300 MHz, ppm): δ=5.63 (s, 4H, NH), 6.23 (d, $^3J_{HF}$=11.6, 2 H, H-1/8), 6.65 (d, $^4J_{HF}$=7.8, 2 H, H-4/5), 7.15 (d, 3J$_{HH}$=7.9, 1H, H-7'), 8.30 (d, J=7.9, 1H, H-6'), 8.38 (s, 1H, H-4'); $^{13}$C NMR ([D$_6$]DMSO, 75.5 MHz, ppm): δ=83.4 (s, C-9), 101.5 (d, J=4.4, C4/5), 104.7 (d, $^3J_{CF}$=6.2, C-8a/8b), 112.0 (d, $^2J_{CF}$=20.8, C-1/8), 122.3 (s, PhCOOH), 124.5 (s, PhCOOH), 125.7 (s, C-3'), 136.0 (s, PhCOOH), 139.1 (d, $^2J_{CF}$=15.0, C-3/6), 142.9 (s, C-5'), 146.9 (d, $^1J_{CF}$=236, C-2/7), 147.9 (s, C-4a/4b), 151.8 (s, C-2'), 167.5 (s, CO), 168.5 (s, CO); $^{19}$F NMR ([D$_6$] DMSO, 282 MHz, ppm): δ=−139.09÷−139.24 (m, 2 F); ESI-MS, negative mode: m/z (rel. int., %)=409 (100) [M−H]$^−$; ESI-MS, positive mode: m/z (rel. int., %)=411 (100) [M+H]$^+$, 455 (10) [M+2Na−H]$^+$. 6'-isomer: $^1$H NMR ([D$_6$]DMSO, 300 MHz, ppm): δ=5.62 (s, 4H, NH), 6.22 (d, $^3J_{HF}$=11.6, 2 H, H-1/8), 6.65 (d, $^4J_{HF}$=7.8, 2 H, H-4/5), 7.59 (s, 1H, H-7'), 7.85 (d, $^3J_{HH}$=7.8, 1H, H-5'), 8.18 (d, $^3J_{HH}$=7.7, 1H, H-4'); $^{13}$C NMR ([D$_6$]DMSO, 75.5 MHz, ppm): δ=83.5 (s, C-9), 101.5 (d, $^3J_{CF}$=4.4, C-4/5), 104.6 (d, $^3J_{CF}$=6.1, C-8a/8b), 112.0 (d, $^2J_{CF}$=20.8, C-1/8), 123.4 (d, J=8.2, PhCOOH), 126.0 (s, C-3'), 128.7 (s, PhCOOH), 130.6 (s, PhCOOH), 139.1 (d, $^2J_{CF}$=15.0, C-3/6), 145.3 (s, C-5'), 147.9 (s, C-4a/4b), 149.9 (d, $^1J_{CF}$=227.3, C-2/7), 153.2 (s, C-2'), 167.7 (s, CO), 168.4 (s, CO).

2,7-Difluoro-N,N'-dimethylrhodamine (37-Me-H—H) was prepared from compound 36-Me (372 mg, 2.64 mmol) and phthalic anhydride (259 mg, 1.75 mmol) according to the general method (5). The title compound was purified by chromatography on SiO$_2$ with CH$_2$Cl$_2$/methanol mixture (20:1-1:1) as an eluent followed by reversed-phase chromatography on RP-18 with H$_2$O/methanol mixture (2:1). Yield—156 mg (30%) of a bright pink solid. HPLC-area: 90%, t$_R$=10.1 min, impurities with t$_R$=8.9 and t$_R$=13.2 min (A/B:70/30-100/0 in 25 min, detection at 254 nm). $^1$H NMR ([D$_6$]DMSO, 300 MHz, ppm): δ=2.78 (d, $^5J_{HF}$=2.8, 6 H, CH$_3$), 6.09 (d, $^4J_{HF}$=3.15, 2H, NH), 6.25 (d, $^3J_{HF}$=12.1, 2 H, H-1/8), 6.47 (d, $^4J_{HF}$=7.7, 2H, H-4/5), 7.25 (d, $^3J_{HF}$=7.6, 1H, H-7'), 7.68-7.82 (m, 2H, H-5'/6'), 7.98 (d, $^3J_{HH}$=7.5, 1H, H-4'); $^{13}$C NMR ([D$_6$]DMSO, 75.5 MHz, ppm): δ=29.2 (s, CH), 84QA$_1$ (S, C-9), 97.4 (d, $^3J_{CF}$=4.2, C-4/5), 103.0 (d, $^3J_{CF}$=6.4, C-8a/8b), 111.2 (d, $^2J_{CF}$=20.5, C-1/8), 123.7 (s, PhCOOH), 124.6 (s, PhCOOH), 126.4 (s, C-3'), 130.0 (s, PhCOOH), 135.3 (s, PhCOOH), 140.3 (d, $^2J_{CF}$=14.2, C-3/6), 147.1 (d, $^1J_{CF}$=237, C-2/7), 148.5 (s, C-4a/4b), 151.7 (s, C-2'), 168.3 (s, CO); $^{19}$F NMR ([D$_6$]DMSO, 282 MHz, ppm): δ=−139.4 (ddd, J$_{HF}$=1.7, 7.7, 11.9); ESI-MS, positive mode: m/z (rel. int., %)=395 (100) [M+H]$^+$, 417 (15) [M+Na]$^+$.

5'(6')-Carboxy-2,7-difluoro-N,N'-dimethylrhodamine (37-Me-H—COOH/38-Me-H—COOH) was prepared as a mixture of 2 diastereomers from aniline 36-Me (0.26 g, 1.84 mmol) and trimellitic anhydride (0.22 g, 1.15 mmol) according to the general method 5. Total yield of a red-brown solid— 154 mg (38%). The pure 6'-isomer (5 mg) was isolated by column chromatography on RP-18 (VWR) with methanol/water mixture (1:1) as an eluent. 5' isomer: $^1$H NMR ([D$_6$] DMSO, 300 MHz, ppm): δ=2.78 (s, 6H, NCH$_3$), 3.97 (br. s, 3H, NH, COOH), 6.38 (d, $^3J_{HF}$=12, 2 H, H-1/8), 6.50 (d, $^4J_{HF}$=8, 2 H, H-4/5), 7.64 (s, 1H, H-7'), 8.03 (d, $^3J_{HH}$=8, 1H, H-5'), 8.08 (d, $^3J_{HH}$=8, 1H, H-4'). 6' isomer: $^1$H NMR ([D$_6$] DMSO, 300 MHz, ppm): δ=2.48 (s, 6H, NCH$_3$), 3.67 (br.s, 4H, NH, COOH), 6.72 (d, $^3J_{HF}$=12, 2H, H-1/8), 6.77-6.86 (m, 2H, H-4/5), 7.48 (d, $^3J_{HH}$=8, 1H, H-7'), 8.23 (d, J=8, 1H, H-6'), 8.58 (s, 1H, H-4'); $^{19}$F NMR ([D$_6$]DMSO, 282 MHz, ppm): δ=−139.4 (m). Mixture of isomers: ESI-MS, positive mode: m/z (rel. int., %)=439 (100) [M+H]$^+$, 440 (20) [M+2H]$^+$; ESI-MS, negative mode: m/z (rel. int., %)=437 (100) [M−H]$^−$, 875 (86) [2M−H]$^−$.

2,7-Difluoro-N,N,N',N'-tetramethylrhodamine (37-Me-Me-H) was prepared from aniline 31-OH (256 mg, 1.65 mmol) and phthalic anhydride (178 mg, 1.20 mmol) according to the general method (5). The title compound was isolated by chromatography on SiO$_2$ with CH$_2$Cl$_2$/methanol mixture (20:1) as an eluent to yield 143 mg (41%) of a dark purple solid. $^1$H NMR (CDCl$_3$, 300 MHz, ppm): δ=2.88 (d, $^5J_{HF}$=0.9, 12 H, CH$_3$), 6.31 (d, 3J$_{HF}$=13.4, 2 H, H-1/8), 6.63 (d, $^4J_{HF}$=7.7, 2 H, H-4/5), 7.16 (d, $^3J_{HH}$=6.9, 1H, H-7), 7.57-7.71 (m, 2H, H-5'/6'), 8.01 (d, J=6.7, 1H, H-4'); $^{13}$C NMR (CDCl$_3$, 75.5 MHz, ppm): δ=42.3 (d, $^4J_{CF}$=5.2, CH$_3$), 83.4 (s, C-9), 104.9 (d, $^3J_{CF}$=3.9, C-4/5), 108.4 (d, $^3J_{CF}$=7.3, C-8a/8b), 113.9 (d, $^2J_{CF}$=24.2, C-1/8), 123.9 (s, PhCOOH), 125.1 (s, PhCOOH), 126.8 (s, C-1'), 129.9 (s, PhCOOH), 135.1 (s, PhCOOH), 142.9 (d, $^2J_{CF}$=10.3, C-3/6), 148.2 (d, $^4J_{CF}$=1.5, C-4a/4b), 150.5 (d, $^1J_{CF}$=242, C-2/7), 152.3 (s, C-2'), 169.1 (s, CO); ESI-MS, positive mode: m/z (rel. int., %)=423 (100) [M+H]$^+$.

2,7-Difluoro-5'(6')-methoxycarbonyl-N,N,N',N'-tetramethyl-rhodamine (37-Me-Me-COOH/38-Me-Me-COOH) was obtained as a mixture of two diastereomers from aniline 31-OH (214 mg, 1.38 mmol) and trimellitic anhydride (200 mg, 1.04 mmol) according to the general method (5). The title product was isolated by chromatography on SiO$_2$ (100 g) with CH$_2$Cl$_2$/methanol mixture (20:1) as an eluent; yield—80 mg (24%) of a dark purple solid. Esterification of the intermediate 5'(6')-carboxy-2,7-difluoro-N,N,N',N'-tetramethyl-rhodamine with methanol occurred on SiO$_2$. 5' isomer: $^1$H NMR ([D$_6$]DMSO, 300 MHz, ppm): δ=2.93 (d, $^5J_{HF}$=1, 12H, CH$_3$), 3.97 (s, 3H, OCH$_3$), 6.51 (d, 3J$_{HF}$=13.8, 2 H, H-1/8), 6.76 (d, $^4J_{HF}$=7.9, 2 H, H-4/5), 7.46 (dd, $^5J_{HH}$=0.7, $^3J_{HH}$=8, 1H, H-7'), 8.39 (dd, $^4J_{HH}$=1.53, $^3J_{HH}$=8.05, 1H, H-6'), 8.51 (dd, $^5J_{HH}$=0.75, $^4J_{HH}$=1.53, 1H, H-4'). 6' isomer: $^1$H NMR ([D$_6$]DMSO, 300 MHz, ppm): δ=2.93 (d, $^5J_{HF}$=1, 12 H, CH$_3$), 6.53 (d, $^3J_{HF}$=13.8, 2 H, H-1/8), 6.74 (d, $^4J_{HF}$=7.9, 2 H, H-4/5), 7.81-7.84 (m, 1H, H-7'), 8.12 (dd, $^5J_{HH}$=0.76, $^3J_{HH}$=8, 1H, H-4'), 8.33 (dd, $^4J_{HH}$=1.34, $^3J_{HH}$=8, 1H, H-5'); ESI-MS, positive mode: m/z (rel. int., %)=481 (100) [M]$^+$.

EXAMPLE 7

Condensation of 5-Hydroxy-N-(2,2,2-Trifluoroethyl) Aniline 41 with Phthalic- and Trimellitic Anhydrides: Preparation of Rhodamines 42-H, 42-COH and 43-COOH (General Method (6))

N,N-Bis(2,2,2-trifluoroethyl)rhodamine 42-H:

A mixture of powdered phthalic anhydride (1.23 g, 8.31 mmol) and compound 41 (1.08 g, 5.65 mmol) was heated with stirring under Ar at 160-170° C. for 3 h. Then the second portion of aniline 41 (0.86 g, 4.51 mmol) and 5 mL of 85% H$_3$PO$_4$ were added, and the heating at 160-170° C. was continued for 3 h more. After cooling to room temperature, MeOH (10 mL) and water (2 mL) were added, the solution was seeded with powdered title compound, and the mixture was stirred at room temperature overnight. The red solid was collected on a glass filter and recrystallized from MeOH to yield 732 mg (30%) of a bright red solid. HPLC-area: 95%, t$_R$=9.4 min (A/B: 60/40-0/100 in 25 min, 1 mL/min, 254 nm). $^1$H NMR ([D$_6$]acetone, 300 MHz, ppm): δ=3.97 (br. s, 2H, NH), 4.37 (q, $^3J_{HF}$=9.1 Hz, 4H, CH$_2$ CF$_3$), 7.23 (s, 6H [in [D$_6$]DMSO: 6.94 s (4H, H-1/8+H-2/7) and 7.11 s (2H, H-4/5)]), 7.50 (dd, $^3J_{HH}$=7.4, $^4J_{HH}$=1.5, 1H, H-7'), 7.83 (t, $^3J_{HH}$=7.4, 1H, H-5'/6'), 7.90 (t, $^3J_{HH}$=7.4, 1H, H-6'/5'), 8.32 (dd, $^3J_{HH}$=7.7, $^4J_{H,H}$=1.6, 1H, H-4'); $^{13}$C NMR ([D$_6$]DMSO, 75.5 MHz, ppm): δ=43.7 (q, $^2J_{C,F}$=33 Hz, CH$_2$ CF$_3$), 48.5 (s), 97.9 (s, C-4/5), 107.2 (s, C-8a/8b), 109.9 (s, C-1/8), 123.9 (s, PhCOOH), 124.3 (s, PhCOOH), 125.5 (q, $^2J_{CF}$=281 Hz, CF$_3$), 126.4 (s, C-3'), 128.3 (s, C-2/7), 129.7 (s, PhCOOH), 135.1 (s, PhCOOH), 149.62 (s, C-3/6 or C-4a/4b), 151.97 (s, C-4a/4b or C-3/6), 152.11 (s, C-2'), 166.9 (s, CO); $^{19}$F NMR ([D$_6$]DMSO, 282.4 MHz, ppm): δ=−70.1 (t, J=9.0 Hz); HRMS (C$_{24}$H$_{16}$N$_2$O$_3$F$_6$): 495.11374 (found M+H), 495.11379 (calc.).

5'-Carboxy-N,N'-bis(2,2,2-trifluoroethyl)rhodamine (42-COOH) and 6'-carboxy-N,N'-bis(2,2,2-trifluoroethyl)rhodamine (43-COOH) were obtained as orange solids from compound 41 (1.90 g, 9.94 mmol; added in two portions) and trimellitic anhydride (1.27 g, 6.61 mmol) as described above for compound 42-H. The 5'-isomer (0.32 g, 24%) was isolated by several recrystallizations from H$_2$O/iPrOH mixture. HPLC-area: 91%, $t_R$=10.3 min; 4% of the second diastereomer (6') with $t_R$=9.6 min (A/B: 30/70-90/10 in 25 min, 488 nm). 6'-Isomer was isolated from the mother liquids by chromatography on RP-18 (VWR) eluting with water/methanol mixture (4:1). HPLC-area: 96%, $t_R$=9.6 min (A/B: 30/70-90/10 in 25 min, 488 nm). 5' isomer: $^1$H NMR ([D$_6$]DMSO, 300 MHz, ppm): δ=3.87 (q, $^3J_{HF}$=9.5, 4 H, CH$_2$ CF$_3$), 4.08 (br. s, 3H, NH, COOH), 6.45 (s, 4H, H-1/8+H-2/7), 6.58 (s, 2H, H-4/5), 7.30 (d, $^3J_{HH}$=8, 1H, H-7'), 8.27 (dd, $^4J_{HH}$=1.5, 3J$_{HH}$=8.0, 1H, H-6'), 8.41 (d, $^4J_{HH}$=0.7, 1H, H-4'). $^{13}$C NMR ([D$_6$]DMSO/CD$_3$OD, 75.5 MHz, ppm): δ=44.3 (q, $^2J_{CF}$=33.0, CH$_2$ CF$_3$), 98.5 (s, C-4/5), 107.4 (s, C-8a/8b), 110.3 (s, C-1/8), 124.7 (s, PhCOOH), 125.9 (s, PhCOOH), 127.7 (s, C-3'), 128.8 (s, C-2/7), 133.2 (s, C-9), 136.1 (s, PhCOOH), 150.2 (s, C-3/6 or C-4a/4b), 152.7 (s, C-4a/4b or C-3/6), 156.3 (s, C-2'), 166.4 (s, CO), 168.4 (s, CO). ESI-MS, negative mode: m/z (rel. int., %)=537 (100) [M−H]$^-$, 1075 (22) [2M−H]$^-$. ESI-MS, positive mode: m/z (rel. int., %)=539 (100) [M+H]$^+$. 6' isomer: $^1$H NMR ([D$_6$]DMSO, 300 MHz, ppm): δ=3.90-4.04 (m, 4H, CH$_2$ CF$_3$), 6.42 (d, $^3J_{HH}$=8.7, 2 H, H-1/8), 6.48 (dd, $^4J_{HH}$=1.8, $^3J_{HH}$=8.7, 2 H, H-2/7), 6.64 (d, J=1.9, 2 H, H-5/4), 6.73 (t, $^4J_{HH}$=6.8, 2 H, NH), 7.54 (s, 1H, H-7'), 7.84 (d, $^3J_{HH}$=7.9, 1H, H-4'/5'), 8.14 (d, $^3J_{HH}$=7.9, 1H, H-5'/4'). $^{13}$C NMR ([D$_6$]DMSO, 75.5 MHz, ppm): δ=43.8 (d, $^2J_{CF}$=32.5, CH$_2$CF$_3$), 83.7 (s, C-9), 98.0 (s, C-4/5), 107.5 (s, C-8a/8b), 109.9 (s, C-1/8), 123.2 (s, PhCOOH), 123.7 (s, PhCOOH), 125.7 (q, $^1J_{CF}$=281, CF$_3$), 126.2 (s, C-3'), 128.4 (s, C-2/7), 130.4 (s, PhCOOH), 149.7 (s, C-3/6 or C-4a/4b), 152.0 (s, C-4a/4b or C-3/6), 152.3 (s, C-2'), 167.6 (s, CO), 168.9 (s, CO). ESI-MS, negative mode: m/z (rel. int., %)=537 (100) [M−H]$^-$, 538 (22) [M]$^-$, 1075 (16) [2M−H]$^-$.

Methyl Ester 22 (Formula II):

The powdered 4-methoxycarbonyl phthalic anhydride (0.520 g, 2.52 mmol) and compound 41 (0.209 g, 1.0 mmol) were dissolved in 1,2-dichlorobenzene (3.2 mL), and the mixture was heated with stirring under N$_2$ at 190° C. for 5 min. Then the second portion of aniline (0.254 g, 1.22 mmol) was added, and the mixture was heated overnight. The solvent was evaporated in vacuo, the residue was applied on SiO$_2$ (200 mL), and the title compound was eluted with CH$_2$Cl$_2$/MeOH mixture (10:1-2:1) and isolated as a mixture of 2 diastereomers; yield—0.524 g, 85%.

5' Isomer: $^1$H NMR (CD$_3$OD, 300 MHz, ppm): δ=3.82-3.87 (m, 1H, NH), 3.91 (s, 3H, CH$_3$), 4.21 (q, 3J$_{HF}$=9, 4 H, CH$_2$ CF$_3$), 6.95 (d, $^3J_{HH}$=9, 2 H, H-1/8), 7.10 (d, $^4J_{HH}$=2, 2 H, H-4/5), 7.14 (d, $^3J_{HH}$=9, 2 H, H-2/7), 7.52 (d, $^3J_{HH}$=9, 1H, H-7'), 8.39 (d, 3J$_{HH}$=8, 1H, H-6'), 8.87 (dt, $^4J_{HH}$=2, $^5J_{HH}$=0.9, 1H, H-4').

6' Isomer: $^1$H NMR (CD$_3$OD, 300 MHz, ppm): δ=3.95-3.98 (m, 1H, NH), 4.01 (s, 3H, CH$_3$), 4.21 (q, 3J$_{HF}$=9, 4 H, CH$_2$ CF$_3$), 6.97 (d, $^3J_{HH}$=9, 2 H, H-1/8), 7.10 (d, $^4J_{HH}$=2, 2 H, H-4/5), 7.13 (d, $^3J_{HH}$=9, 2 H, H-2/7), 7.98 (t, $^4J_{HH}$=1, 1H, H-7'), 8.35-8.42 (m, 2H, H-4'/5'). ESI-MS, positive mode: m/z (rel. int., %)=553 (80) [M+H]$^+$, 575 (45) [M+Na]$^+$, 1127 (100) [2M+Na]$^+$. ESI-MS, negative mode: m/z (rel. int., %)=551 (100) [M−H]$^-$, 470 (40) [M-CH$_2$ CF$_3$—H]$^-$.

EXAMPLE 8

Sulfonation of Fluorinated Rhodamines 33-H—H, 3-H—COOH/35-H—COOH, 37-H—H—H, 37-H—H—COOH/38-H—H—COOH, 42-H, 42-COOH, 43-COOH (General Method (7))

2,7-Difluoro-N,N'-bis(2,2,2-trifluoroethyl)-4,5-disulforhodamine (46-H—CH$_2$ CF$_3$—F—H):

A solution of SO$_3$ (30% in H$_2$ SO$_4$, 0.48 g, obtained by mixing of 20% and 65% solutions of SO$_3$ in H$_2$ SO$_4$) was added at 0° C. to rhodamine 33-H—H (50 mg, 0.094 mmol). The mixture was stirred overnight (0° C.—room temperature) and then kept at 4° C. for 96 h. The sulfonation reaction was controlled by HPLC or analytical RP-TLC. After the full conversion of the rhodamine into the corresponding disulfonic acid was observed, the reaction mixture was carefully mixed with ice (5-10 mL) and immediately applied on the top of the prepacked column (RP-C18, 50 g). Elution with water/methanol mixture (10:1→1:1, +0.1% v/v TFA) afforded the title compound, which was isolated after lyophilisation as a very light bright orange solid, yield—53 mg (82%). HPLC: $t_R$=8.3 min (A/B: 30/70-100/0 in 25 min, 254 nm). $^1$H NMR (CD$_3$OD, 300 MHz, ppm): δ=4.45 (q, $^3J_{HF}$=8.4, 4 H, CH$_2$CF$_3$), 6.99 (d, $^3J_{HF}$=14.2, 2 H, H-1/8), 7.52 (d, 3J$_{HH}$=7, 1H, H-7'), 7.78-7.87 (m, 2H, H-5'/6'), 8.34 (d, J=8.8, 1H, H-4'); $^{13}$C NMR (CD$_3$OD, 75 MHz, ppm): δ=46.9-47.8 (m, CH$_2$ CF$_3$), 115.3-115.8 (m, C-4/5), 116.7 (d, $^2J_{CF}$=25.2, C-1/8), 128.1 (q, $^1J_{CF}$=278, CF$_3$), 130.9, 131.6, 132.3, 134.5, 136.1, 147.4, 151.0, 153.4, 154.5, 167.9 (CO); ESI-MS, negative mode: m/z (rel. int., %)=689 (68) [M−H]$^-$, 711 (100) [M+Na-2H]$^-$.

5',(6')-Carboxy-2,7-difluoro-N,N''-bis(2,2,2-trifluoroethyl)-4,5-disulforhodamine (46-H—CH$_2$ CF$_3$—F-(5'/6')—COOH) was obtained as a bright orange solid from rhodamine 33-H—COOH/35-H—COOH (54 mg, 0.094 mmol) and 30% SO$_3$ in H$_2$ SO$_4$ (0.5 g) according to the general method (7). The reaction mixture was kept for 6 days at +4° C., yield—46 mg (67%). HPLC: $t_R$=6.0 min (A/B: 30/70-100/0 in 25 min, 254 nm). 6' isomer: $^1$H NMR ([D$_6$]DMSO, 300 MHz, ppm): δ=4.14-4.30 (m, 4H, CH$_2$ CF$_3$), 6.83 (d, $^3J_{HF}$=12, 2H, H-1/8), 7.45 (br. s, 4H, NH, OH), 7.84 (d, $^3J_{HH}$=7, 1H, H-7'), 8.15 (d, 3J$_{HH}$=7, 1H, H-4'/5'), 8.27 (d, 3J$_{HH}$=7, 1H, H-5'/4'). 5' isomer: $^1$H NMR ([D$_6$]DMSO, 300 MHz, ppm): δ=4.14-4.30 (m, 4H, CH$_2$ CF$_3$), 6.86 (d, 3J$_{HF}$=12, 2H, H-1/8), 7.45 (br.s, 4H, NH, OH), 7.56 (s, 1H, H-7'), 8.32 (d, $^3J_{HH}$=7, 1H, H-6'), 8.44 (s 1H, H-4'). Mixture of isomers: ESI-MS, negative mode: m/z (rel. int., %)=733 (100) [M−H]$^-$, 755 (21) [M+Na-2H]$^-$.

2,7-Difluoro-4,5-disulforhodamine (46-H—H—F—H): was obtained from compound 37-H—H—H (30 mg, 0.082 mmol) and 30% SO$_3$ in H$_2$ SO$_4$ (0.5 mL) according to the general method 7. The reaction mixture was kept at +4° C. for 72 h, carefully mixed with ice and then the title compound was isolated by chromatography on RP-18 (VWR) with water/methanol (5:1) mixture as an eluent, yield—14 mg (32%). HPLC: $t_R$=5.2 min (A/B: 20/80-50/50 in 25 min, 488 nm). $^1$H NMR (D$_2$O, 300 MHz, ppm): δ=6.98 (d, $^3J_{HF}$=11.0, 2 H, H-1/8), 7.29-7.34 (m, 1H, H-7'), 7.79-7.83 (m, 2H, H-5'/6'), 8.26-8.32 (m, 1H, H-4'); $^{19}$F NMR (D$_2$O, 282 MHz, ppm): δ=−127.2 (s, 1 F), −127.2 (s, 1 F); ESI-MS, negative mode: m/z (rel. int., %)=525 (100) [M−H]$^-$.

5' (6')-Carboxy-2,7-difluoro-4,5-disulforhodamine (46-H—H—F-(5'/6')—COOH) was obtained as a mixture of 2 diastereomers by sulfonation of rhodamine 37-H—H—COOH/38-H—H—COOH (25.0 mg, 0.061 mmol) with 30% $SO_3$ in $H_2SO_4$ (0.7 mL) at +4° C. for 48 h. Bright red solid (26 mg, 75%) was isolated by reversed-phase chromatography on RP-18 (75 g) with water/methanol mixture (4:1) as an eluent. 5'isomer: $^1H$ NMR ($D_2O$, 300 MHz, ppm): δ=2.76 (s, 1H, $SO_3H$), 7.09 (d, $^3J_{HF}$=11.0, 2 H, H-1/8), 7.61 (d, $^3J_{HH}$=8.0, 1H, H-7'), 8.48 (dd, $^4J_{HH}$=1.8, $^3J_{HH}$=8.0, 1H, H-6'), 8.93 (d, J=1.6, 1H, H-4'). Signals of the second isomer are too weak. $^{19}F$ NMR ($D_2O$, 282 MHz, ppm): δ=−126.88 (s, 3 F, $CH_2CF_3$), −126.85 (s, 3 F, $CH_2CF_3H$), −126.78÷−126.80 (m, 1 F), −126.75 (s, 1 F); ESI-MS, negative mode: m/z=569 [M−H]$^−$, 591 [M+Na-2H]$^−$.

4,5-Disulfo-N,N'-bis(2,2,2-trifluoroethyl)rhodamine (46-H—$CH_2CF_3$—H—H) was obtained according to the general method 7 as a bright orange solid by sulfonation of rhodamine 42-H (158 mg, 0.32 mmol) with 30% $SO_3$ in $H_2SO_4$ (1.52 g). The reaction mixture was kept at +4° C. for 48 h, and, after the reaction was complete (HPLC-control), the reaction solution was transferred onto frozen 1,4-dioxane (10 mL, −20° C.), mixed with it, and then cold dry ether (20 mL) was added. After stirring at 0° C. for 30 min, the organic solution was decanted from the lower layer, and the latter was carefully mixed with ice (10 g). The title compound was isolated by chromatography on the RP-18 eluting with water/methanol mixture (4:1); yield—36 mg (17%). $^1H$ NMR ($CD_3OD$, 300 MHz, ppm): δ=4.29 (q, $^3J_{HF}$=8.8, 4 H, $CH_2CF_3$), 7.21-7.30 (m, 4H, H-1/8/+H-2/7), 7.37-7.42 (m, 1H, H-3'), 7.77 (pd, J=1.6, 7.5, 2 H, H-5'/6'), 8.30-8.26 (m, 1H, H-4'); $^{13}C$ NMR ($CD_3OD$, 75.5 MHz, ppm): δ=45.1 (q, $^2J_{CF}$=34, $CH_2CF_3$), 114.2 (s, C-4/5), 115.9 (s, C-8a/8b), 115.9 (s, C-1/8), 125.7 (q, $^1J_{CF}$=279, $CF_3$), 131.4 (s, PhCOOH), 132.0 (s, PhCOOH), 132.0 (s, C-3'), 132.7 (s, PhCOOH), 134.2 (s, PhCOOH), 134.5 (s, C-9), 155.9 (s, C-3/6 or C-4a/4b), 156.6 (s, C-3/6 or C-4a/4b), 165.8 (s, C-2'), 167.8 (s, CO); ESI-MS, negative mode: m/z (rel. int., %)=653 (24) [M−H]$^−$, 675 (100) [M+Na-2H]$^−$.

5'-Carboxy-4,5-disulfo-N,N'-bis(2,2,2-trifluoroethyl)-rhodamine (46-H—H—F-(5')—COOH) and 6'-Carboxy-4,5-disulfo-N,N-bis(2,2,2-trifluoroethyl) rhodamine (46-H—H—F—(6')—COOH) were obtained as bright orange solids by sulfonation of rhodamine 42-COOH (157 mg, 0.292 mmol) and 43-COOH (35.0 mg, 0.065 mmol) with 30% $SO_3$ in $H_2SO_4$ (2.40 and 1.40 g, respectively) according to the general method 7. The reaction mixtures were kept at +4° C. for 48 h, and after the reactions were complete (HPLC-control), carefully mixed with ice. The title compounds were isolated by chromatography on the RP-18 with water/methanol mixtures (4:1) as an eluent and the lyophilized. HPLC-area for the sum of both isomers: 100%, $t_R$=11.3 min, (ACN/$H_2O$: 20/80-50/50 in 25 min, 498 nm); yield of 5' isomer—126 mg (62%); yield of 6' isomer—29 mg (60%). 5' isomer: $^1H$ NMR ([$D_6$]DMSO, 300 MHz, ppm): δ=4.40 (br. q, $^3J_{HF}$=9.1, 9H, $CH_2CF_3$, NH, COOH, $SO_3H$), 7.04 (d, $3J_{HH}$=9.0, 2 H; H-1/8), 7.13 (d, $^3J_{HH}$=9.0, 2 H, H-2/7), 7.58 (d, $^3J_{HH}$=8.0, 1H, H-7'), 8.34 (dd, $^4J_{HH}$=1.6, $^3J_{HH}$=8.0, 1H, H-6'), 8.63 (br. s, 1H, H-4'). $^{13}C$ NMR (DMSO-$d_6$, 75.5 MHz, ppm): δ=43.5 (q, $^2J_{CF}$=33.2, $CH_2CF_3$), 112.6 (s), 125.0 (q, $J_{CF}$=280, $CF_3$), 131.7 (s), 133.0 (s), 166.0 (s, CO), 166.2 (s, CO). ESI-MS, negative mode: m/z (rel. int., %)=697 (7) [M−H]$^−$, 719 (100) [M+Na-2H]$^−$. 6' isomer: $^1H$ NMR ($CD_3OD$, 300 MHz, ppm): δ=4.40 (q, $^3J_{HF}$=8.9, 4 H, $CH_2CF_3$), 7.31-7.40 (m, 4H, H-1/8+H-2/7), 8.08 (d, $^4J_{HH}$=0.9, 1H, H-7'), 8.40-8.49 (m, 2H, H-4'/5').

Methyl ester 44-Me:
Rhodamine 42-H (1.70 g, 3.44 mmol) was suspended in 1,2-dichloroethane (30 mL), and $POCl_3$ (5 mL, 0.05 mol) was added in one portion. The mixture was refluxed at 110° C. for 2 h. Then the solvent and the excess of $POCl_3$ were evaporated in vacuo, dry $CH_3CN$ (110 mL) was added followed by 1.43 g (14 mmol) of $CH_3NH(CH_2)_2CO_2CH_3$ and $Et_3N$ (0.6 mL, 4.2 mmol). The solution was stirred at room temperature for 20 h. Then the solvent and excess of $Et_3N$ were evaporated in vacuo (ca. 1 mbar), $CH_2Cl_2$ (16 mL) was added to the residue, and the mixture was filtered through $SiO_2$ (100 g) eluting with $CH_2Cl_2$/MeOH mixture (50:1→10:1). The title compound was isolated as a bright red solid (1.41 g, 65%) and recrystallized from MeOH/water mixture. HPLC-area: 90%, $t_R$=10.0 min (A/B: 40/60-100/0 in 25 min, 254 nm). $^1H$ NMR ([$D_6$]DMSO, 300 MHz, ppm): δ=1.99 (t, $^3J_{HH}$=8, 2 H, $CH_2CO_2CH_3$), 2.81 (s, 3H, $NCH_3$), 3.26-3.37 (m, 2H, $NCH_2$), 3.43 (s, 3H, $OCH_3$), 4.45 (q, $^3J_{HF}$=9.4, 4 H, $CH_2CF_3$), 7.14-7.33 (m, 6H, H-1/8+H-2/7+H-4/5), 7.51-7.55 (m, 1H, H-7'), 7.62-7.68 (m, 1H, H-4'), 7.70-7.78 (m, 2H, H-5'/6'), 9.28 (s, 2H, NH). $^{13}C$ NMR ([$D_6$]DMSO, 75.5 MHz, ppm): δ=30.5 (s, $CH_2N$), 37.2 (s, $NCH_3$), 43.3 (q, $^2J_{CF}$=33.4, $CH_2CF_3$), 50.9 (s, $OCH_3$), 114.2 (s, C-8a/8b), 124.7 (q, $^1J_{CF}$=281, $CF_3$), 127.1 (s,), 129.20 (s,), 129.6 (s, C-3'), 129.9 (s), 129.9 (s), 131.8 (s), 135.8 (s), 157.6-157.8 (m), 157.9 (s, C-2'), 158.2 (s, C-4a/4b), 167.4 (s, CO), 171.0 (s, CO). ESI-MS, positive mode: m/z (rel. int., %)=594 (100) [M, $C_{29}H_{26}F_6N_3O_4^+$].

Carboxylic acid 44-H:
Methyl ester 44-Me (26.0 mg, 0.041 mmol) was suspended in MeOH (2 mL) and THF (1 mL), and 1 M aq. NaOH (0.7 mL, 0.7 mmol) was added dropwise at 0° C. After stirring for 2 h at room temperature, HPLC indicated the full conversion into a new compound, which was isolated by chromatography on RP-18 with water/methanol mixture (1:4+0.05% TFA) as an eluent; yield—16 mg (68%). HPLC: $t_R$=11.5 min (A/B: 30/70-100/0 in 25 min, 254 nm). $^1H$ NMR ([$D_6$]DMSO, 300 MHz, ppm): δ=1.91 (t, $^3J_{HH}$=8, 2 H, $CH_2$ COO), 2.83 (s, 3H, $NCH_3$), 3.22-3.27 (m, 2H, $NCH_2$), 4.37-4.49 (br. m, 4H, $CH_2CF_3$), 7.18-7.25 (m, 4H, H-1/8+H-2/7), 7.28 (s, 2H, H-4/5), 7.51-7.54 (m, 1H, H-7'), 7.62-7.67 (m, 1H, H-4'), 7.71-7.76 (m, 2H, H-5'/6'). ESI-MS ($C_{28}H_{23}N_3F_6O_4$), positive mode: m/z (rel. int., %)=580 (100) [M+H]$^+$.

Rhodaminic Alcohol 46:
The title compound was obtained as a bright red solid from rhodamine 42-H (308 mg, 0.62 mmol), $POCl_3$ (0.6 mL) and 0.5 g (6.7 mmol) of $CH_3NHCH_2CH_2OH$ at 70-90° C. (at the second step) as described above for methyl ester 44-Me. The residue after evaporation of $CH_2Cl_2$ was dissolved in iPrOH and placed onto column with silica gel (100 mL). The title compound was eluted with $CH_2Cl_2$/methanol (4:1) mixture. HPLC-area: 95%, $t_R$=7.38 min (ACN/$H_2O$: 40/60-100/0 in 25 min, 254 nm); yield—283 mg (78%). $^1H$ NMR ($CD_3OD$, 300 MHz, ppm): δ=2.68/3.32 (s, 3H, $NCH_3$), 3.15-3.27 (m, 4H, $NCH_2$, $CH_2OH$), 4.24 (t, $^3J_{HF}$=9, 4 H, $CH_2CF_3$), 7.06 (d, $^3J_{HH}$=9, 2 H, H-2/7), 7.17 (s, 2H, H-4/5), 7.33-7.40 (m, 2H, H-1/8), 7.49-7.52 (m, 1H, H-7'), 7.53-7.57 (m, 1H, H-4'), 6.71-6.79 (m, 2H, H-5'/6'). ESI-MS, positive mode ($C_{27}H_{24}N_3O_3F_6^+$): m/z (rel. int., %)=552 (100) [M$^+$]. ESI-MS, negative mode: m/z (rel. int., %)=550 (100) [M$^+$-2H]$^−$, 586 (80) [M+Cl$^-$H]$^-$ Disulfonic Acid 45-OH:
The title compound was obtained as a bright orange solid by sulfonation of the carboxylic acid 44-H (14 mg, 0.024 mmol) with 30% $SO_3$ in $H_2SO_4$ (0.95 g) according to the general method 7. The reaction mixture was kept at +4° C. for 48 h, and after the reaction was complete (HPLC-control), frozen 1,4-dioxane (5 mL) was very carefully added to it at 0°

C. with stirring. Then dry ether (15 mL) was added carefully, and the mixture was stirred at 0° C. for 30 min. The upper layer was decanted, and the title compound was isolated from the residue by chromatography on RP-18 with water/methanol mixture (4:1→2:1) as an eluent; yield—5 mg (28%). $^1$H NMR (CD$_3$OD, 300 MHz, ppm): δ=2.10 (t, $^3J_{HH}$=8, 2H, CH$_2$ COOH), 2.94 (s, 3H, NCH$_3$), 3.42 (t, $^3J_{HH}$=8, 2H, NCH$_2$), 4.41 (q, $^3J_{HF}$=9, 4H, CH$_2$ CF$_3$), 7.35 (d, $^3J_{HH}$=9, 2 H, H-2/7), 7.46 (d, $^3J_{HH}$=9, 2 H, H-1/8), 7.51-7.54 (m, 1H, H-7'), 7.64-7.68 (m, 1H, H-4'), 7.73-7.80 (m, 2H, H-5'/6'). ESI-MS, positive mode (C$_{28}$H$_{23}$F$_6$N$_3$O$_{10}$S$_2$): m/z (rel. int., %)=762 (12) [M+Na]$^+$, 784 (100) [M+2Na—H]$^+$, 810 (56) [M+3Na-2H]$^+$.

NHS Ester 43-CONHS:

Rhodamine 43-COOH (6' isomer, 23 mg, 43 µmol) was dissolved in DMF (0.4 mL) and 23 mg (198 µmol) of N-hydroxysuccinimide followed by Et$_3$ N (2.0 µL) were added at 0° C. After several minutes, 41 mg (0.108 mmol) of O-(7-azabenzotriazol-1-yl)-N,N,N,N'-tetramethyluronium (HATU) were added to the reaction mixture, and it was stirred at room temperature for 24 h. The solvent was evaporated in vacuo, and the title compound was isolated by preparative HPLC (A/B: 30/70-100/0 in 25 min, preparative column, 4 mL/min, detection at 488 nm).

NHS Ester 46-H—CH$_2$ CF$_3$—H-(5'-)CONHS was obtained from rhodamine 46-H—CH$_2$ CF$_3$—H-(5')COOH (14 mg, 0.020 mmol), N-hydroxysuccinimide (11.6 mg 0.101 mmol), and HATU (14 mg, 0.037 mmol) as described above. After the reaction was complete, the solvent was evaporated in vacuo, and the title compound was isolated by preparative HPLC; t$_R$=12.9 min (A/B: 20/80-50/50 in 25 min, 490 nm); yield—4 mg (25%); HPLC-area: 90%.

NHS Ester 45-NHS was obtained from rhodamine 45-OH (15 mg, 0.020 mmol), N-hydroxysuccinimide (38 mg, 0.330 mmol), and HATU (53 mg, 0.139 mmol) as described above.

NHS Ester 44-NHS:

Rhodamine 44-H (15 mg, 0.026 mmol) was dissolved in DMF (0.07 mL), then 30 mg (0.104 mmol) of N,N,N,N'-tetramethyl-O— (N-succinimidyl)uromium BF$_4$— (TSTU) and 0.06 mL of Et$_3$ N were added at 0° C. The reaction mixture was stirred at room temperature for 24 h. The solvent was removed in vacuo, and the title compound was isolated by preparative HPLC; t$_R$=12 min (A/B: 30/70-90/10 in 25 min, analytical column, 488 nm); yield—5 mg (28%).

EXAMPLE 9

Conjugation with Antibodies

The amino reactive derivatives of the dyes presented here can be easily attached to the antibodies (AB) used in standard immunostaining procedures, in cell biology. The labeling of the AB with an organic (fluorescent) dye involves the dissolution of both components (e.g. in PBS buffer at pH 8.5) followed by the reaction for 1-2 hours at room temperature. Poor solubility of a dye in aqueous solutions may result either in a low labeling efficiency (few dye molecules attached to each AB, in average) and/or in the precipitation of the labeled antibodies. Another problem which may arise is a decrease in the fluorescent properties of a dye after coupling with an AB. Lipophilic fluorescent dyes often turn out to be less bright in polar environments (e.g. after coupling with proteins). The dyes of the present invention are suitable for conjugation with commercial antibodies, yielding highly fluorescent adducts with only minor alterations of the spectral properties. For instance, the absorption and emission spectra of the dye 17 and its adduct with an AB are shown in FIG. 3. The spectra are very similar, except for the strong absorption band observed for 17-AB at 280 nm, which is typical for proteins. Moreover, the dye retained about 75% of its emission efficiency after coupling with the AB.

From FIG. 3, an average labeling efficiency of 4.6 molecules of the fluorescent dye 17 per antibody is calculated. For immunoglobulin G, the optimal labeling is achieved with rhodamine dyes with 3-7 moles of dye per mol of antibody. Immunostained samples with AB labeled with our compounds were very bright and stable, and gave excellent images in standard fluorescent microscopy, as well as in modern superresolution techniques. These results are given and discussed in the following Example 10.

EXAMPLE 10

Stimulated Emission Depletion Studies and Immunostainings with the New Fluorescent Dyes Fluorescent probes for high-resolution microscopy techniques, such as STED (Stimulated Emission Depletion Microscopy) must be resistant to high light intensities, both for excitation and for depletion of the fluorescent signal. Photofatigue resistance is a crucial parameter for gaining a good resolution enhancement, as the achievable resolution strongly depends on the irradiation power applied in the depletion process. The depletion of the fluorescence signal obtained for compounds 12, 14a, 15-17 is presented in FIG. 4, for variable STED powers applied at around 600 nm. In combination with their high photoresistance, these results confirm that the new dyes are very promising candidates for STED microscopy. Optimal wavelengths are 488-532 nm for the excitation processes, and around 600 nm for the depletion.

Figure 4:
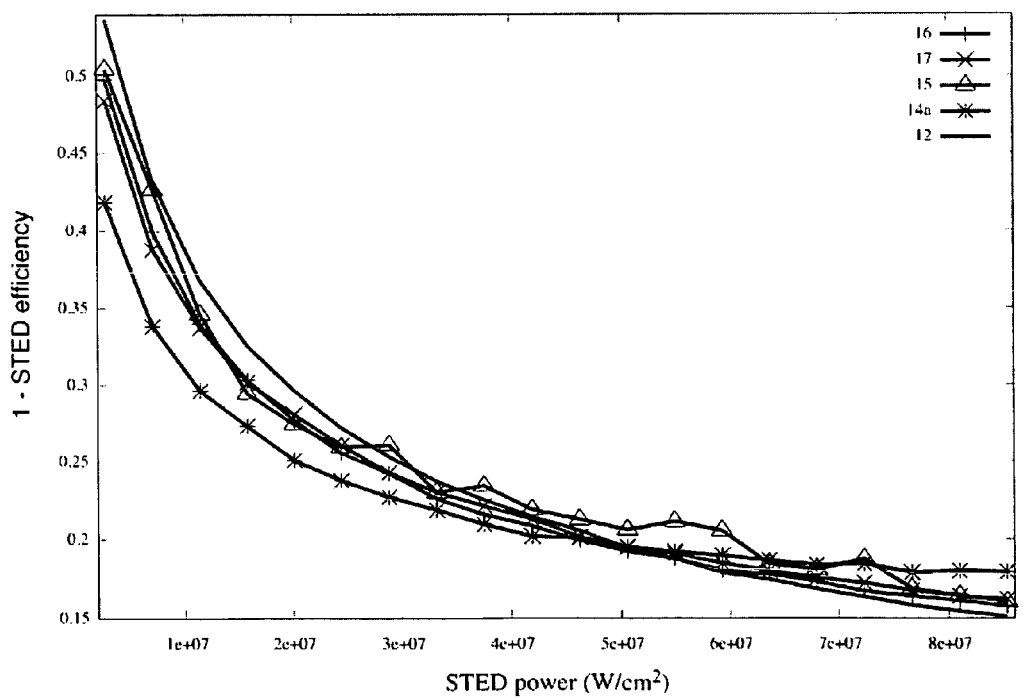
Figure 5A:
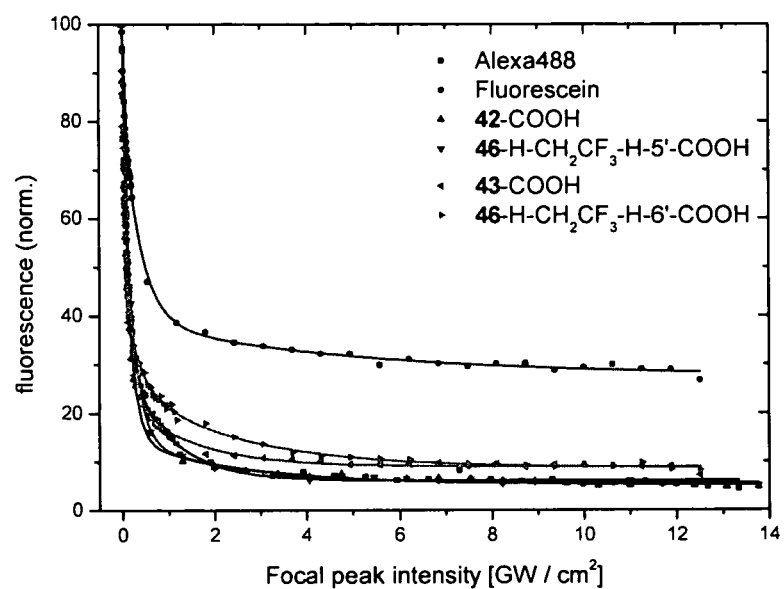
Figure 5B:
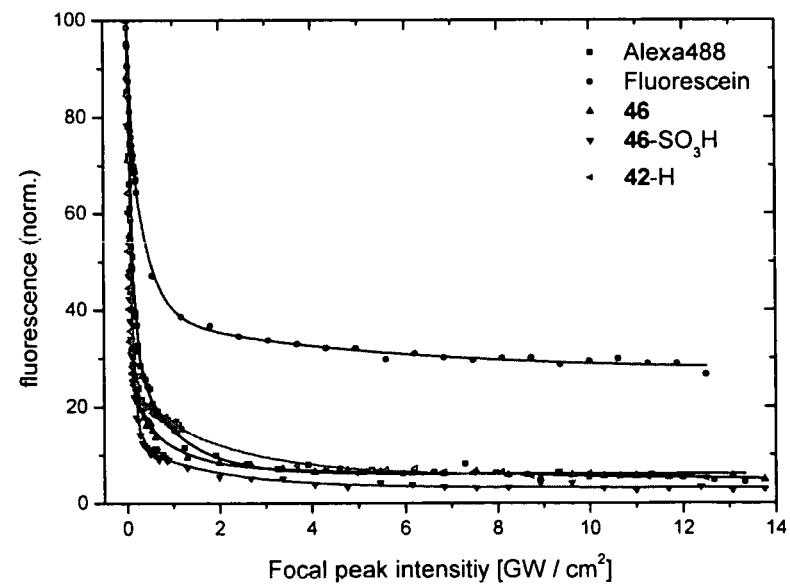

The fluorescence depletion curves in FIG. 4 have been recorded using CW-lasers with moderate focal peak intensities. However, the dyes also show excellent compatibility with STED under pulsed excitation. FIG. 5 displays the depletion curves of different derivatives of substances 42, 43 and 46 using 593 nm—STED light at a repetition rate of 250 kHz. Increasing the STED power to very high focal peak intensities almost completely depletes the fluorescent signal. For comparison the depletion behavior of Alexa Fluor 488® and Fluorescein are also shown.

In one experiment, PtK2 cells were immunostained with the AB labeled with the NHS esters of the dyes introduced in the present invention, and imaged in a STED microscope yielding excellent images with sub-diffraction resolution (for a general description of a STED microscope see e.g.: Opt. Expr. 2008, 16, 4154-4162).

In FIG. 6, examples of the images obtained from the samples stained with compounds 15 and 17 are given. High quality pictures were recorded both in the standard (confocal) imaging mode and in the STED mode, and in different stained structures (tubulin and vimentin, in the examples of FIG. 6). Note that the dye 15 is not a derivative of the sulfonated rhodamine. Nevertheless, it does not produce any background (no aggregation visible), and the images are bright. Excitation was performed at 488 nm with intensity in the focus of 1-5 kW/cm$^2$, and STED at 600 nm with 80 MW/cm$^2$. Some features are only resolved in the high-resolution technique. Thus, a clear resolution enhancement is obtained in the STED mode, as compared with the standard counterpart. The compounds presented here can be used as fluorescent probes in standard and in STED microscopy. Readily available light sources can be used: excitation can be performed at 488 nm and 514 nm, and depletion can be performed with high efficiency in the 580-620 nm range. The optimal values depend on the selected dye.

As further demonstrations of the excellent optical properties of the new dyes, FIGS. 7 and 8 present STED and confocal images of the microtubule-associated protein Doublecortin immunostained with anti-Doublecortin rabbit IgG conjugated with the compound 46-H—CH$_2$ CF$_3$—H-5'-CONHS. The STED images have been recorded in pulsed mode (f=250 kHz, $\lambda_{STED}$=593 nm) thus allowing for high focal peak intensities (~2.1 GW/cm$^2$) and therefore strong resolution enhancement. Clearly, the undefined blobs in the confocal image are well-resolved in STED-mode revealing small spots with full-width-half-maxima (FWHM) of approximately 35-40 nm. The signal-to-noise ratio remains high even under STED conditions which again reflects the dye's good resistance against photobleaching.

EXAMPLE 11

Fluorescence Correlation Spectroscopy (FCS) Studies of the New Fluorescent Dyes

In combination with modern highly sensitive detection technologies recently developed, the observation of a single or a few molecules has become readily available. Several techniques based on these measurements [such as the fluorescence fluctuation spectroscopy and fluorescence correlation spectroscopy (FCS)] advantageously reveal molecular properties otherwise hidden by averaging the ensemble. A common requirement for experiments involving a few or single molecules is the use of fluorescent dyes with high photostability especially at high excitation intensities of >100 kW/cm$^2$. For biological applications the use of water as a solvent is almost imperative. Low solubility in water is often associated with a high bleaching ratio, or lower fluorescence quantum yield in aqueous medium compared with that in organic solvents. A new series of probes described here is very stable in aqueous media under the excitation conditions required for single molecules.

FIG. 10 shows the results of the FCS experiments performed in aqueous solutions with compound 17, and the carboxy rhodamine 110 (Rh110-CO$_2$), taken as a reference. The excitation intensity of 115 kW/cm$^2$ (a value normally used in routinely FCS measurements) and at an excitation intensity of about an order of magnitude higher (2 MW/cm$^2$) have been used. At lower excitation intensity only diffusion in the focal volume with a characteristic time in the 0.1-1 ms range, and a small amount of triplet buildup, evidenced by an extra relaxation contribution on the microsecond time range, have been observed for both dyes. At higher intensity a shortening of the apparent diffusion characteristic time of Rh110-CO$_2$ due to a bleaching contribution that effectively reduced the average observation time of a molecule within the focal spot is observed. An increase in the fraction of molecules in the triplet state can also be detected. On the contrary, compound 17 showed no significant change in the diffusion time over the studied intensity range (0.1-2.0 MW/cm$^2$), which indicates that even under these severe excitation conditions no bleaching is observed for this compound. All the other compounds are also very photostable and suitable as FCS probes, with a photo-fatigue resistance similar to that of the reference dye Rh110-CO$_2$. Compound 17 turned out to be the most stable one and represents a considerable improvement over a commonly used probe (Rh110-CO$_2$).

EXAMPLE 12

Studies on the Intracellular Availability of the New Fluorescent Dyes

Microscopic imaging of protein dynamics and distributions in living cells is one of the most important tasks in cell biology. For imaging of specifically labeled proteins in living cells, typically genetically created chimeric proteins consisting of a host protein and a reporter protein are used. In addition to the widely used fluorescent fusion proteins, several strategies were established over the last years to label proteins specifically with organic fluorophores (H. M. O'Hare, K. Johnsson, A. Gautier, *Curr. Opin. Struct. Biol.* 2007, 17, 488-494).

In a typical approach, a modified cellular enzyme is used for covalent addition of a dye. Currently only a limited number of dyes is available for these labeling strategies.

The most important prerequisite for fluorophores used in these labeling strategies is that sufficient amounts of it need to pass cellular membrane(s) to reach the target protein. In order to asses the permeability of the cell membrane to the fluorescent dyes described in the presented invention, living mammalian cells (PtK2) previously grown overnight on cover slips, were first subjected to either 500 μg dye/ml or 50 μg dye/ml in growth medium for 15 minutes. (The amount of dye used for labeling of SNAP-fusion proteins is below 5 μg dye/ml.) Then, the cells were washed with growth medium (without dye) for 15 minutes, and imaged using an epifluorescence microscope.

Upon treatment with a 500 μg dye/ml solution, all the dyes were able to permeate the cellular membrane(s) of living mammalian cells (Table 3), with the exception of two compounds (46-H—H—F-5'/6'-COOH (13) and 46-H—H—F—H (12)). Only 15 minutes of incubation was enough to achieve the necessary amount of dye to label intracellular structures like protein aggregates (visible as dots), vesicles or mitochondria non-specifically. Therefore, this amount is expected to be sufficient to label proteins specifically, combined with labeling strategies such as SNAP-, CLIP- or Halo-tag-.

The dyes still reached the interior of living cells (Table 4, FIG. 9) upon treatment with a 50 μg dye/ml solution. However, the unspecifically labeled structures were dimmer, accounting for the lower concentration of the dye inside the cells.

TABLE 3

Structures stained in living cells after subjection to 500 μg dye/ml

| Dye | Structures stained in living cells |
|---|---|
| 22 | Bright background staining visible. Mitochondria stained. |
| 28 | Red cytoplasmatic and mitochondrial stain visible. |
| 33/35-Me—COOH (26) | Cellular stain visible; bright background. |
| 33/35-Me—COOMe (26, 5'/6'-Methylester) | Dim cellular stain visible. |
| 33-Me—H (25) | Only dim stain visible. |
| 37/38-H—H—COOH (11) | Dye exclusion! No dye within cell visible. |
| 37/38-Me—H—COOH (12) | Cellular stain visible; bright background. |
| 37-H—H—H (10) | High background staining visible. |
| 37-Me—H—H (22) | Mitochondrial stain visible. Bright background. |
| 37-Me—Me—H (27) | Red cytoplasmatic and mitochondrial stain visible. |
| 42-COOH (15) | Bright cytoplasmatic stain visible. |
| 42-H (14) | Nearly no stain visible. |
| 42-H (14)-Methylester | Mitochondria or Vesicles stained brightly. |
| 43-COOH (15) | Nearly no stain visible. |
| 44-H (14a) | Mitochondrial stain visible. |
| 44-Me | Cytoplasmatic stain visible. |

TABLE 3-continued

Structures stained in living cells after subjection to 500 μg dye/ml

| Dye | Structures stained in living cells |
|---|---|
| 45-OH (16a) | Cellular stain visible; bright background |
| 46-H—CH$_2$CF$_3$—F-5'/6'-COOH (21) | Cytoplasmatic and mitochondrial stain visible. |
| 46-H—CH$_2$CF$_3$—F—H (20) | Nearly no stain visible. |
| 46-H—CH$_2$CF$_3$—H—5'-COOH (17) | Bright background staining visible. |
| 46-H—CH$_2$CF$_3$—H—H (16) | Dim cellular stain with brightly stained mitochondia visible. |
| 46-H—H—F-5'/6'-COOH (13) | Nearly no stain visible. |
| 46-H—H—F—H (12) | Nearly no stain visible. |

TABLE 4

Structures stained in living cells after subjection to 50 μg dye/ml

| Dye | Structures stained in living cells |
|---|---|
| 22 | Vesicles visible. |
| 28 | Dim red cytoplasmatic stain with green dots visible. |
| 33/35-H—COOH (19) | Dim cellular stain with dots visible. |
| 33-H—H (18) | Dim cytoplasmatic stain with bright vesicles visible. |
| 37-Me—H—H (22) | Dim cytoplasmatic stain with dots visible. |
| 37-Me—Me—H (27) | Dim cytoplasmatic stain with dots visible. Green to Red conversion visible. |
| 42-COOH (15) | Dim cytoplasmatic stain with dots visible. |
| 42-H (14)-Methylester | Mitochondria or vesicles visible. |
| 46-H—CH$_2$CF$_3$—F-5'/6'-COOH (21) | Dim cytoplasmatic stain with dots visible. |
| 46-H—CH$_2$CF$_3$—F—H (20) | Dim cytoplasmatic stain with dots visible. |
| 46-H—CH$_2$CF$_3$—H—5'-COOH (17) | Dim cytoplasmatic stain with dots visible. |
| 46-H—CH$_2$CF$_3$—H—H (16) | Dim cytoplasmatic stain with bright vesicles visible. |
| 46-H—H—F-5'/6'-COOH (13) | Dim cytoplasmatic stain with dots visible. |

In summary, the new dyes are able to cross the cellular membrane(s) and reach the interior of living cells. They are a useful addition to the currently available gallery of dyes for labeling strategies within living cells (e.g. N,N,N',N'-tetramethylrhodamine [TMR]).

EXAMPLE 13

Ground State Depletion Studies of the New Fluorinated Rhodamines

The claimed compounds were found to possess properties, which make them useful for the super-resolution far-field microscopy based on ground-state depletion, such as GSDIM (ground-state depletion followed by individual molecule return) (J. Fölling et. al, *Nature Meth.* 2008, 5, 943-945). In this method, "off" and "on" switching of the fluorescence is achieved by transiently shelving the fluorophores into a metastable dark state. Upon the return of only a few isolated single molecules to the fluorescent singlet state, positions of these single light emitting spots can be imaged on a camera and localized with high precision. Upon repeating this procedure and acquiring many pictures, a super-resolution image can be reconstructed from the localized positions. A prerequisite of this method is that >70% of the ensemble of the applied fluorescent dyes can be shelved into a dark state at a time (to ensure the detection of isolated fluorescent spots at a time in a densely labeled sample) and that the fluorophores are bright enough, i.e., that they emit enough photons while being in the singlet on-state (to ensure high precision of localization).

It was found that at laser intensities I=6-10 kW/cm$^2$ of continuous-wave (CW) 488 nm laser light 70-92% of all fluorophores of the compounds in poly(vinyl alcohol) matrix can be switched-off at a time. Switching off of the laser leads to a recovery of the fluorescence ensemble within a characteristic recovery time of 150-450 ms (Table 5), indicating the shelving into a metastable dark state. The measurements were performed in a pump-probe mode, i.e., the residual level of fluorescence was probed with I<100 W/cm$^2$ for 0.5 ms after strong irradiation for 10 ms with the given laser intensity in Table 5.

Furthermore, recovery of the fluorescence can be accelerated by addition of UV light, which leads to an optically-induced depopulation of the dark states. Already 2-3 kW/cm$^2$ of 375 nm light recovers the fluorescence within an irradiation period of 0.5 ms. This works well for all dyes except compound 17 (46-H—CH2CF3-H-5'-COOH). The accelerated recovery is important for samples with low density of labels, where the addition of UV light and thus acceleration of the return from a dark state helps to accelerate image acquisition. Photostabilities of the studied fluorescent dyes under the GSDIM conditions are different: 15-50 pump-probe cycles with a pump intensity of 14-110 kW/cm$^2$ bleach 30-95% of the whole ensemble.

TABLE 5

Ground state depletion parameters of the fluorescent dyes 12, 17, 44-Me and 16a in PVA matrix

| Compound | $\lambda_{ex}/\lambda_{em}$ (nm) | $R_{fl, t=0}$ (%)[a] | I[b] (kW/cm$^2$) | UV[c] | $\Gamma_{fl}$[d] (%) | $\tau_{fl}$[e] (ms) |
|---|---|---|---|---|---|---|
| 12 (46-H—H—F—H) | 488/512 | 8 | 110 | + | 20 | 450 |
| 17 (46-H—CH$_2$CF$_3$—H-5'-COOH) | 501/524 | 25 | 20 | (+) | 40 | 250 |
| 44-Me | 512/534 | 8 | 18 | + | 90 | 260 |
| 20 (46-H—CH$_2$CF$_3$—F—H) | 506/531 | 25 | 14 | + | 50 | 225 |
| 16a (45-OH) | 512/530 | 25 | 14 | + | 35 | 150 |

Notes:
[a]residual fluorescence after the pump-pulse;
[b]power density of the pump-pulse;
[c]enhanced recovery of the fluorescence by "tickling" with UV-light (see text for details);
[d]remaining fluorescence after 5 measurement cycles (with the given power density) at one spot helps to evaluate the photoresistance of a dye under the given GSDIM conditions;
[e]recovery time.

Summarizing, new photostable rhodamine dyes derived from the general formula I (represented by the exemplary compounds 10-28, 14a and 16a) are disclosed herein as efficient fluorescent markers with unique combination of structural features. Two fluorine atoms were introduced into the positions 2' and 7' of the 3',6'-diaminoxanthene fragment. Unlike rhodamines with monoalkylated nitrogen atoms, N',N-bis(2,2,2-trifluoroethyl) derivatives were found to undergo sulfonation of the xanthene fragment at the positions 4' and 5'. New fluorescent dyes presented here may readily be excited with 488 or 514 nm light; most of them emit light at 512-554 nm (two of them at 586-589 nm) and have high fluorescence quantum yields in solution (up to 98%), relatively long excited state lifetimes (>3 ns) and are resistant against photobleaching in the presence of air-oxygen. Sulfonation of the lipophilic fluorescent dyes of formula I ($R^{21}$=H, $R^{22}$=H or $CH_2 CF_3$, $X_1$=H, $Y_1$, $Y_{22}$=H or F, $X_3$=H, COOR, Z=OH, $N(Alk)(CH_2)_n COOH$) affords the hydrophilic derivatives of formula I with $X_1$=$X_2$=$SO_3H$. After attaching amino (or thiol) reactive sites, the modified derivatives may be used as fluorescent markers in (bio)conjugation procedures. The new rhodamine derivatives may be also used as labels for biomolecules in light microscopy using conventional (confocal) and reversible saturable optically linear fluorescent transition (RESOLFT) techniques (e.g. STED microscopy), as well as fluorescence correlation spectroscopy and ground state depletion and single molecule return method, where very high light intensities are used and the highest possible photoresistance is required for resolving the light emitting objects, whose separation distance is below the diffraction limit (~200 nm in the visible range). The presence of the fluorine atoms at the positions 2' and 7' of the 3,6-diaminoxanthene fragment and/or N',N-bis(2,2,2-trifluoroethyl) groups facilitates the ability of the dye to pass the cellular membrane(s) and reach the interior of living cells.

The invention claimed is:

1. A fluorinated 3,6-diaminoxanthene compound represented by the following structural formulae Ib, Ie, Ig or Ij

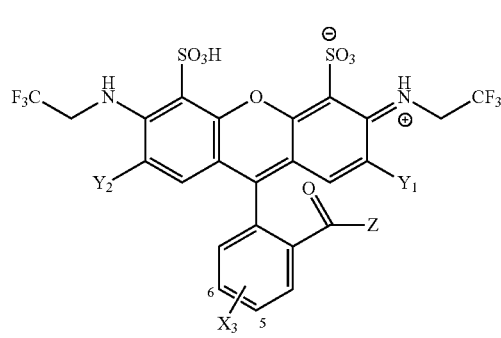

Ib

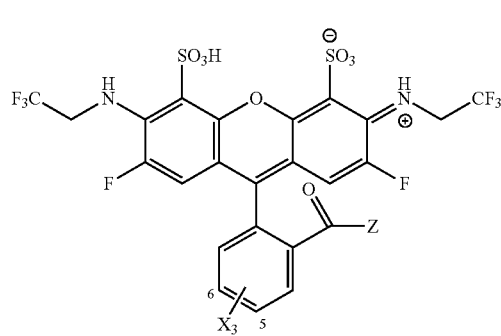

Ie

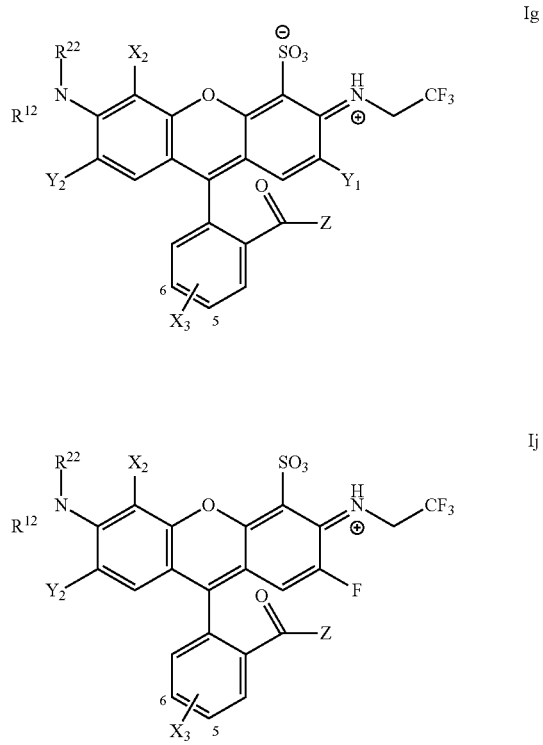

Ig

Ij and wherein in each of formulae Ib, Ie, Ig and Ij $X_3$=5-COOH or 6-COOH or an ester thereof, and substituents $R^{12}$, $R^{22}$, $X_2$, $Y_1$, $Y_2$, alone or two substituents taken together, is (are) hydrogen atoms or any alkyl, cycloalkyl, heterocycloalkyl, aryl, heterocyclic aryl groups, or any functionally substituted alkyl, cycloalkyl, aryl, heterocyclic aryl groups, or any combination of the said groups; and wherein in each of formulae Ib, Ie, Ig and Ij Z=$OR^3$ or $NR^4R^5$, where $R^3$, $R^4$ and $R^5$ is (are) hydrogen atom(s), any alkyl, cycloalkyl, heterocycloalkyl, aryl, heterocyclic aryl group(s), or any functionally substituted alkyl, cycloalkyl, aryl, heterocyclic aryl group(s), or any combination of the said groups.

2. The compound according to claim 1, having the basic formula II

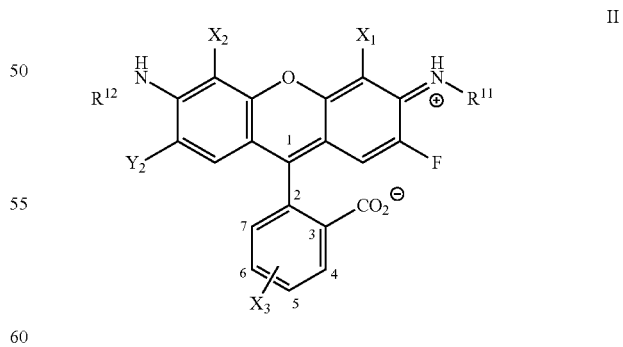

II and being selected from the group of compounds 17 and 21 with the following substitution patterns:

17: $Y_1$=$Y_2$=H; $X_1$=$X_2$=$SO_3H$; $R_{11}$=$R_{12}$=$CH_2CF_3$; $X_3$=COOH

21: $Y_1$=$Y_2$=F; $X_1$=$X_2$=$SO_3H$; $R_{11}$=$R_{12}$=$CH_2CF_3$; $X_3$=COOH.

3. A method for preparing 4,5-disulfono-3,6-bis[N,N-(2,2,2-trifluoroethyl)amino]xanthenes Ib,e or 4-sulfono-6-amino-3-[N'-(2,2,2-trifluoroethyl)amino]xanthene derivatives Ig,j by direct sulfonation of a corresponding unsulfonated N[,N'-bis](2,2,2-trifluoroethyl)-substituted 3,6-diaminoxanthene derivative at positions 4 and 5 in the course of a one-step procedure by reacting with a sulfonating agent.

4. A conjugate of a compound according to claim 1 and a biomolecule selected from the group consisting of peptides, proteins, lipids, carbohydrates, nucleic acids and toxins.

* * * * *